(12) United States Patent
Iwasawa et al.

(10) Patent No.: US 7,709,475 B2
(45) Date of Patent: May 4, 2010

(54) SELECTIVE INHIBITORS AGAINST CDK4 AND CDK6 HAVING AMINOTHIAZOLE SKELETON

(75) Inventors: Yoshikazu Iwasawa, Tsukuba (JP); Jun Shibata, Tsukuba (JP); Tadashi Shimamura, Tsukuba (JP); Hideki Kurihara, Tsukuba (JP); Takashi Mita, Tsukuba (JP); Nobuhiko Kawanishi, Moriya (JP); Takashi Hashihayata, Tsukuba (JP); Mikako Kawamura, Tsukuba (JP); Takeshi Sagara, Tsukuba (JP); Sachie Arai, Tsukuba (JP); Hiroshi Hirai, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 792 days.

(21) Appl. No.: 11/596,735

(22) PCT Filed: May 19, 2005

(86) PCT No.: PCT/JP2005/009593

§ 371 (c)(1),
(2), (4) Date: Nov. 17, 2006

(87) PCT Pub. No.: WO2006/008874

PCT Pub. Date: Jan. 26, 2006

(65) Prior Publication Data

US 2008/0081811 A1 Apr. 3, 2008

(30) Foreign Application Priority Data

May 21, 2004 (JP) ............................. 2004-178974

(51) Int. Cl.
*C07D 417/12* (2006.01)
*A61K 31/506* (2006.01)
*C07D 417/14* (2006.01)
*C07D 491/08* (2006.01)

(52) U.S. Cl. ............ 514/230.5; 514/235.8; 514/252.11; 514/252.14; 514/252.19; 514/274; 514/275; 544/105; 544/122; 544/295; 544/316; 544/331

(58) Field of Classification Search ................. 544/105, 544/122, 295, 316, 331; 514/230.5, 235.8, 514/252.11, 252.14, 252.19, 274, 275
See application file for complete search history.

(56) References Cited

U.S. PATENT DOCUMENTS

2005/0176719 A1 8/2005 Hayama et al.
2006/0019959 A1 1/2006 Hirai et al.
2007/0027147 A1 2/2007 Hayama et al.

FOREIGN PATENT DOCUMENTS

WO WO 01/17995 3/2001
WO WO 01/72745 10/2001

OTHER PUBLICATIONS

Banker et al., Prodrugs, Modern Pharmaceutics, Third Edition, Revised and Expanded, pp. 451 and 596.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Lu Valle et al., Cell Cycle Control in Growth Plate Chondrocytes, Frontiers in Biosciences 5, d493-503, May 2000.*
Traxler, Protein tyrosine kinase inhibitors in cancer treatment, Expert Opinion on Therapeutic Patents, 7(6), pp. 571-588, 1997.*
Simone, Oncology: Introduction, Cecil Textbook of Medicine, 20th Edition, vol. 1, pp. 1004-1010, 1996.*
Blain et al., Differential Interaction of the Cyclin-dependent Kinase (Cdk) Inhibitor p27Kip1 with Cyclin A-Cdk2 and Cyclin D2-Cdk4, The Journal of Biological Chemistry, vol. 272, No. 41, pp. 25863-25872, 1997.*

* cited by examiner

*Primary Examiner*—Deepak Rao
(74) *Attorney, Agent, or Firm*—David A. Muthard

(57) ABSTRACT

The present invention relates to a compound represented by Formula [I]:

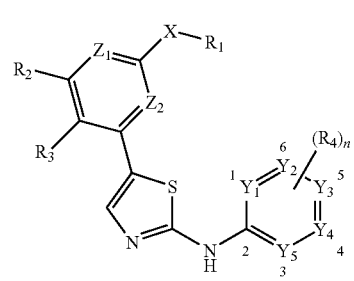

wherein
X is O, S, NH or $CH_2$;
$Y_1, Y_2, Y_3, Y_4$ and $Y_5$, which may be identical or different, are each CH or N; however, at least one of $Y_1, Y_2, Y_3, Y_4$ and $Y_5$ is N;
$Z_1$ and $Z_2$, which may be identical or different, are each CH or N;
n is an integer from 1 to 3;
$R_1$ is a $C_3$-$C_8$ cycloalkyl group, a $C_6$-$C_{10}$ aryl group, an aliphatic heterocyclic ring or an aromatic heterocyclic ring, or a bicyclic aliphatic saturated hydrocarbon group;
$R_2$ and $R_3$, which may be identical or different, are each a hydrogen atom, a lower alkyl group, a lower alkenyl group, a $C_3$-$C_8$ cycloalkyl group, a $C_6$-$C_{10}$ aryl group, an aromatic heterocyclic ring, or the like; and
$R_4$ is a hydrogen atom, a lower alkyl group, a $C_3$-$C_6$ cycloalkyl group or the like,
or a pharmaceutically acceptable salt or ester thereof, and a selective inhibitor against Cdk4 and/or Cdk6 or an anticancer agent containing the compound or a pharmaceutically acceptable salt or ester thereof.

11 Claims, No Drawings

SELECTIVE INHIBITORS AGAINST CDK4 AND CDK6 HAVING AMINOTHIAZOLE SKELETON

PRIORITY CLAIM

This application is a §371 application of PCT/JP2005/009593 that was filed on May 19, 2005, which claims priority from the Japanese Patent Application JP2004-178974, filed on May 21, 2004, now expired.

TECHNICAL FIELD

The present invention relates to a novel derivative having an aminothiazole skeleton, which is useful in the field of medicine, and more particularly, to a novel derivative having an aminothiazole skeleton which inhibits proliferation of tumor cells, thereby exhibiting an anticancer effect, and a selective inhibitor against Cdk4 and/or Cdk6 containing the derivative.

BACKGROUND ART

Proliferation of normal cells involves orderly occurrence of cell division and its pause which proceed along the cell cycle, whereas proliferation of cancer cells is characterized by its disorderliness. Therefore, it is presumed that abnormality in the cell cycle control mechanism is directly related to oncogenesis or malignant alteration of cancer. The cell cycle of mammal cells is controlled by serine/threonine kinases that are generically called the cyclin dependent kinases (hereinafter, referred to as "Cdk") family, and in order for a Cdk to express the enzyme activity, the Cdk is required to form a complex with a regulatory subunit called cyclin. Cyclins also constitute a family, and it is believed that each Cdk molecule regulates the progression of certain phases in the cell cycle by forming a complex with a limited type of cyclin molecule which is specifically expressed at the corresponding phase of the cell cycle. For example, D-type cyclins bind with Cdk4 or Cdk6 to regulate the progression of G1 phase; cyclin E-Cdk2 regulates the G1/S boundary; cyclin A-Cdk2 regulates the progression of S phase; and cyclin B-cdc2 regulates the progression of G2/M. In addition, D-type cyclins are known to have three subtypes of D1, D2 and D3, and the activity of Cdk is believed to be controlled not only by the binding with cyclins, but also by phosphorylation/dephosphorylation of Cdk molecules, decomposition of cyclin molecules, and binding with Cdk inhibitory proteins [Advance Cancer Res., Vol. 66, 181-212 (1995); Current Opin. Cell Biol., Vol. 7, 773-780 (1995); and Nature, Vol. 374, 131-134 (1995)].

The Cdk inhibitory proteins found in mammal cells are classified into two major classes of Cip/Kip family and INK4 family, on the basis of the differences in structure and nature. The former widely inhibits cyclin-Cdk complexes, whereas the latter binds with Cdk4 and Cdk6 to specifically inhibit them [Nature, Vol. 366, 704-707 (1993); Mol. Cell. Biol., Vol. 15, 2627-2681 (1995); and Genes Dev., Vol. 9, 1149-1163 (1995)].

A representative example of the former may be p21 (Sdi1/Cip1/Waf1), whose RNA transcription is induced by p53, a product of tumor suppressor gene [Genes Dev., Vol. 9, 935-944 (1995)].

On the other hand, for example, p16(INK4a/MTS1/CDK4I/CDKN2) is one of the Cdk inhibitory proteins belonging to the latter family. p16 gene is found at human chromosome region 9p21, which is very frequently found with anomalies in human cancer cells, and in fact, deletion of p16 gene has been reported in a number of cases in the clinical practice. It has been also reported that the frequency of cancer occurrence is high in p16-knockout mice [Nature Genet., Vol. 8, 27-32 (1994); Trends Genet., Vol. 11, 136-140 (1995); and Cell, Vol. 85, 27-37 (1996)].

Each Cdk controls the progression of cell cycle by phosphorylating a target protein found at a specific phase of the cell cycle, but among such target proteins, retinoblastoma (RB) protein is considered to be one of the most important target proteins. The RB protein is a key protein in the progression from G1 phase to S phase, and is rapidly phosphorylated during the term from late G1 phase to initial S phase. This phosphorylation is believed to be carried out by cyclin D-Cdk4/Cdk6 complex and then by cyclin E-Cdk2 complex, which are associated with the progression of cell cycle. When RB protein is hyperphosphorylated, a complex that has been formed by a hypophosphorylated form of RB and a transcription factor E2F until that time point at early G1 phase, dissociates. As a result, E2F becomes a transcriptional activator, and at the same time, the suppression of the promoter activity by the RB-E2F complex is removed, thereby E2F-dependent transcription being activated. Currently, a Cdk-RB pathway involving E2F and its inhibitor RB protein, and Cdk4/Cdk6 regulating the function of RB protein in a suppressive manner, Cdk inhibitory protein regulating the kinase activity thereof, and D-type cyclins, is construed as an important mechanism controlling the progression from G1 phase to S phase [Cell, Vol. 58, 1097-1105 (1989); Cell, Vol. 65, 1053-1061 (1991); Oncogene, Vol. 7, 1067-1074 (1992); Current Opin. Cell Biol., Vol. 8, 805-814 (1996); and Mol. Cell. Biol., Vol. 18, 753-761 (1998)]. In fact, the E2F-binding DNA sequence is, for example, located in the upstream of many cell proliferation-related genes that are important in S phase, and it is reported that in a plurality of such genes among them, transcription is activated in an E2F-dependent manner over a period spanning from late G1 phase to early S phase [EMBO J., Vol. 9, 2179-2184 (1990); and Mol. Cell. Biol., Vol. 13, 1610-1618 (1993)].

Abnormalities in several factors constituting the Cdk-RB pathway, for example, deletion of functional p16, high expression of cyclin D1 or high expression of Cdk4, deletion of functional RB protein, or the like, have been very frequently detected in human cancer [Science, Vol. 254, 1138-1146 (1991); Cancer Res., Vol. 53, 5535-5541 (1993); and Current Opin. Cell Biol., Vol. 8, 805-814 (1996)]. These are all abnormalities in the direction of promoting the progression from G1 phase to S phase, and it is obvious that this pathway is playing an important role in canceration or abnormal proliferation of cancer cells.

The Applicant of the present invention created unique compounds having a Cdk inhibitory effect in the past, and have filed patent applications concerning novel biaryl urea derivatives (WO 01/07411), novel pyrazinone derivatives (WO 02/002550), and novel quinoxalinone derivatives (WO 04/039809).

However, reports on aminothiazole derivatives having excellent selective inhibitory effects against Cdk4 and/or Cdk6 cannot be found so far (WO 01/72745). A compound having an excellent selective inhibitory effect against Cdk4 and/or Cdk6 in contrast to other Cdks, is expected to serve as an anticancer agent with a greater margin of safety.

Furthermore, since Cdk4 and Cdk6 are factors generally related to the control of cell cycle and cell proliferation, a selective inhibitor thereof is expected to be beneficial for the treatment of diseases inducing abnormalities in the cell cycle and cell proliferation, which include for example, but are not limited to, arthritis, arteriosclerosis, pulmonary fibrosis and cerebral infarction.

In these cases, it is anticipated that suppression of cell cycle and cell proliferation through Cdk inhibition will be effective, based on the following technical expertise.

In the case of rheumatoid arthritis, over-proliferation of synovial tissue in the affected area is well known. Proliferation of cells from this tissue is relevant to the level of expression of Cdk inhibitory proteins, p21 and p16, and it is reported that when p16 is introduced onto the affected areas of rheumatoid arthritis-model animals, there is an improvement in the symptoms [Nat. Med., Vol. 5, 760-767 (1999)].

In the case of arteriosclerosis, over-proliferation of smooth muscle cells in the endothelial lining of arterial walls is important, but it is known that suppression of Cdk expression by antisense oligonucleotides in an experimental plaque model using a balloon catheter, and forced expression of p21 and p27 by adenovirus vectors, inhibit neointima formation [Int. J. Mol. Med., Vol. 2, 81-89 (1998)].

It is also reported that expression of cell cycle inhibitory protein p21 induced by adenovirus vectors is effective in pulmonary fibrosis-model mice [Am. J. Physiol. Lung. Cell Mol. Physiol., Vol. 286, L727-L733 (2004)].

In a rat cerebral infarction model, it is known that neuronal death due to localized ischemia enhances the cyclin D1/Cdk4 level, and it is reported that neuronal death is suppressed by administration of a non-selective Cdk inhibitor, flavopyridol [Proc. Natl. Acad. Sci. USA, Vol. 97, 10254-10259 (2000)].

DISCLOSURE OF THE INVENTION

It is an object of the present invention to provide a novel aminothiazole derivative which is structurally different as compared with the aminothiazole derivatives disclosed in the aforementioned patent applications, and which has an excellent selective inhibitory effect against Cdk4 and/or Cdk6.

In order to solve the object, the inventors of the present invention synthesized a wide range of aminothiazole derivatives, and discovered that a compound represented by Formula [1] exhibits an excellent selective inhibitory effect against Cdk4 and/or Cdk6, thus completing the invention.

Thus, the invention relates to a compound represented by Formula [I] or a pharmaceutically acceptable salt or ester thereof:

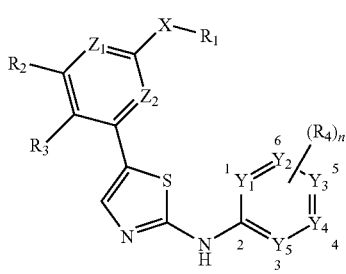

wherein
X is O, S, NH or $CH_2$;
$Y_1, Y_2, Y_3, Y_4$ and $Y_5$, which may be identical or different, are each CH or N; however, at least one of $Y_1, Y_2, Y_3, Y_4$ and $Y_5$ is N;
$Z_1$ and $Z_2$, which may be identical or different, are each CH or N;

n is an integer from 1 to 3;
$R_1$ is a $C_3$-$C_8$ cycloalkyl group, a $C_6$-$C_{10}$ aryl group, an aliphatic heterocyclic group or an aromatic heterocyclic group selected from "Substituent Group $\alpha_1$", or a bicyclic aliphatic saturated hydrocarbon group selected from "Substituent Group $\alpha_2$", wherein the cycloalkyl group, aryl group, aliphatic heterocyclic group or aromatic heterocyclic group, or bicyclic aliphatic saturated hydrocarbon group may be substituted with one or more of identical or different substituents selected from the following 1) to 3):
 1) a lower alkyl group,
 2) a substituent selected from "Substituent Group β", and
 3) a lower alkyl group substituted with a substituent selected from "Substituent Group β";

$R_2$ and $R_3$, which may be identical or different, are each a hydrogen atom, a lower alkyl group, a lower alkenyl group, a $C_3$-$C_8$ cycloalkyl group, a $C_6$-$C_{10}$ aryl group, an aromatic heterocyclic group selected from "Substituent Group $\alpha_3$", or a substituent selected from "Substituent Group β", wherein the lower alkyl group, lower alkenyl group, cycloalkyl group, aryl group or aromatic heterocyclic group may be substituted with one or more of identical or different substituents selected from "Substituent Group β";

$R_4$ is a hydrogen atom, a lower alkyl group, a $C_3$-$C_6$ cycloalkyl group, a substituent selected from "Substituent Group β", or —$W_1$—$W_2$, wherein:
$W_1$ is any one selected from the following:

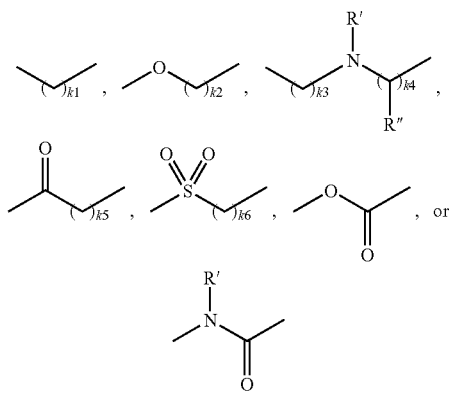

wherein $k_1$ is an integer from 0 to 5; $k_2, k_4, k_5$ and $k_6$, which may be identical or different, are each an integer from 0 to 4; $k_3$ is an integer of 0 or 1; and R' and R", which may be identical or different, are each a hydrogen atom or a lower alkyl group, $W_2$ is a hydrogen atom, a lower alkyl group, a $C_3$-$C_8$ cycloalkyl group, a substituent selected from "Substituent Group β", a $C_6$-$C_{10}$ aryl group, an aliphatic heterocyclic group selected from "Substituent Group $\gamma_1$", or an aromatic heterocyclic group selected from "Substituent Group $\gamma_2$", wherein the lower alkyl group, cycloalkyl group, aryl group, aliphatic heterocyclic group or aromatic heterocyclic group may be substituted with one or more of identical or different substituents selected from the following 1) to 6):
 1) a lower alkyl group,
 2) a $C_3$-$C_6$ cycloalkyl group,
 3) a substituent selected from "Substituent Group β",
 4) a lower alkyl group substituted with a substituent selected from "Substituent Group β",
 5) a substituent selected from "Substituent Group δ", and 6) a lower alkyl group substituted with a substituent selected from "Substituent Group δ", and if $W_2$ is a lower alkyl group, any of the carbon atoms in the alkyl group may form a spiro-heterocyclic ring; and
  if $W_1$ is

and $k_1$ is 0, $W_2$ is not a substituent selected from "Substituent Group β"; the "Substituent Group $α_1$", "Substituent Group $α_2$", "Substituent Group $α_3$", "Substituent Group β", "Substituent Group $γ_1$", "Substituent Group $γ_2$" and "Substituent Group δ" being defined as follows:

"Substituent Group $α_1$":

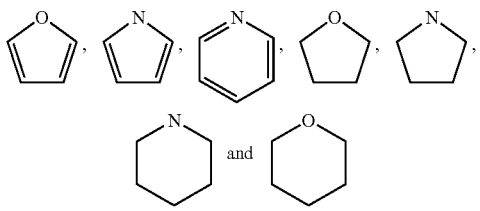

"Substituent Group $α_2$":

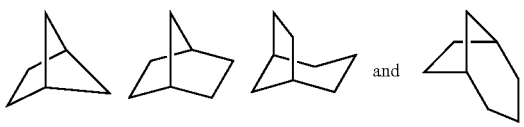

"Substituent Group $α_3$":

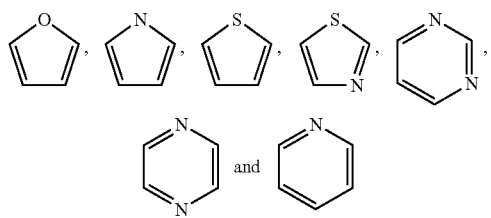

"Substituent Group β":

A halogen atom, OH, OR, $CF_3$, CN, $NH_2$, NHR, $NR_aR_b$, NHCOR, $NR_aCOR_b$, $NHCO_2R$, $NR_aCO_2R_b$, NHCONHR, $NHSO_2R$, $CONH_2$, CONHR, $CONR_aR_b$, COR, $COCF_3$, $CO_2R$, OCOR, $OCO_2R$, $OCONR_aR_b$, $SO_3R$, $SO_2NH_2$, $SO_2NHR$, and $SO_2NR_aR_b$, wherein R, $R_a$ and $R_b$, which may be identical or different, are each a lower alkyl group;

"Substituent Group $γ_1$":

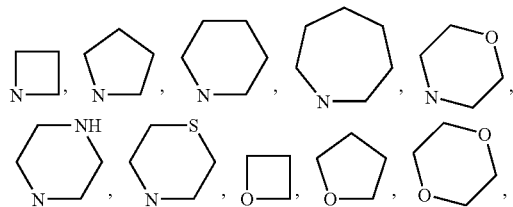

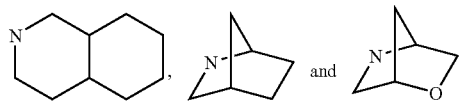

wherein the two hydrogen atoms binding to the same carbon atom constituting an aliphatic heterocyclic group may together form an oxo group;

"Substituent Group $γ_2$"

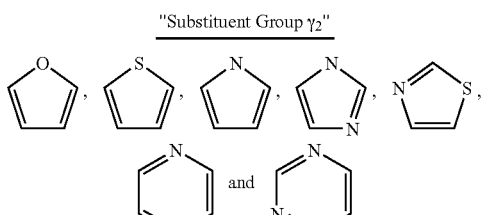

"Substituent Group δ"

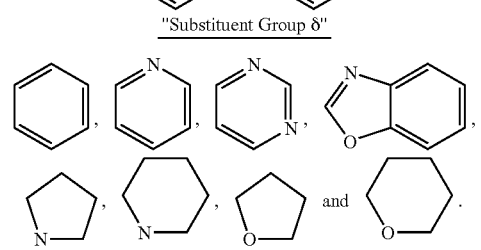

Hereinafter, the symbols and terms described in the present specification will be explained.

The "lower alkyl group" in the Formula (I) refers to a straight-chained or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a pentyl group, a hexyl group and the like. Among these, for example, a methyl group, an ethyl group, a propyl group, an isopropyl group, a tert-butyl group and a pentyl group are preferred, and particularly for $R_2$ and/or $R_3$, a methyl group is preferred.

The "lower alkenyl group" in the Formula (I) refers to a straight-chained or branched alkenyl group having 2 to 6 carbon atoms, and examples thereof include a vinyl group, a 1-propenyl group, an allyl group, an isopropenyl group, a 1-butenyl group, a 3-butenyl group, a 1,3-butanedienyl group, a 2-pentenyl group, a 4-pentenyl group, a 1-hexenyl group, a 3-hexenyl group, a 5-hexenyl group and the like.

The "$C_3$-$C_8$ cycloalkyl group" in the Formula (I) refers to a cyclopropyl group, a cyclobutyl group, a cyclopentyl group, a cyclohexyl group, a cycloheptyl group and a cyclooctyl group, and among these, a cyclohexyl group or a cyclopentyl group are preferred, with the cyclohexyl group being particularly preferred. Also, the "$C_3$-$C_6$ cycloalkyl group" refers to a cyclopropyl group, a cyclobutyl group, a cyclopentyl group or a cyclohexyl group, and among these, a cyclohexyl group is preferred.

The "$C_6$-$C_{10}$ aryl group" in the Formula (I) may be exemplified by a phenyl group, a naphthyl group or the like, and is preferably a phenyl group or a substituted phenyl group.

The "aliphatic heterocyclic group" in the Formula (I) refers in general to a saturated or unsaturated aliphatic heterocyclic group containing at least one atom selected from a nitrogen atom, an oxygen atom and a sulfur atom in addition to carbon atoms, and having a monocyclic ring or a bicyclic or tricyclic fused ring. Examples thereof include an azetidyl group, a pyrrolidinyl group, a piperidinyl group, a piperazinyl group, a morpholino group, a tetrahydrofuranyl group, an imidazolidinyl group, a thiomorpholino group, a tetrahydroquinolyl group, a tetrahydroisoquinolyl group and the like. However, a preferred "aliphatic heterocyclic group" in the Formula (I) is the "aliphatic heterocyclic group" shown in the "Substituent Group $\alpha_1$" or "Substituent Group $\gamma_1$" as described below.

The "aromatic heterocyclic group" in the Formula (I) refers in general to an aromatic heterocyclic group containing at least one heteroatom such as a nitrogen atom, an oxygen atom or the like, and examples thereof include a 5- to 7-membered monocyclic heterocyclic group, a fused-ring heterocyclic group formed by fusion of a 3- to 8-membered ring to the monocyclic heterocyclic group, and the like. Specifically, a thienyl group, a pyrrolyl group, a furyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzimidazolyl group, a benzofuranyl group and the like may be mentioned. However, a preferred "aromatic heterocyclic group" in the Formula (I) is the "aromatic heterocyclic group" shown in the "Substituent Group $\alpha_1$", "Substituent Group $\alpha_3$" and "Substituent Group $\gamma_2$" as described below.

That is, examples of the preferred "aliphatic heterocyclic group or aromatic heterocyclic group" in the Formula (I) (for $R_1$) are as follows:

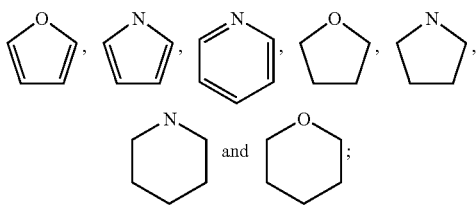

examples of the preferred "aromatic heterocyclic group" in the Formula (I) (for $R_2$ and $R_3$) are as follows:

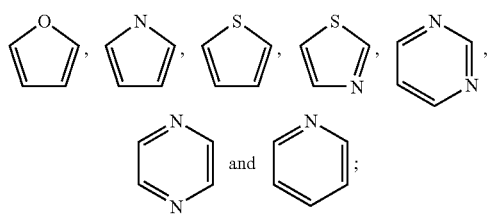

examples of the preferred "aliphatic heterocyclic group" in the Formula (I) (for $W_2$) are as follows:

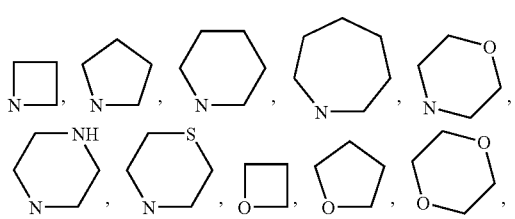

and examples of the preferred "aromatic heterocyclic group" in the Formula (I) (for $W_2$) are as follows:

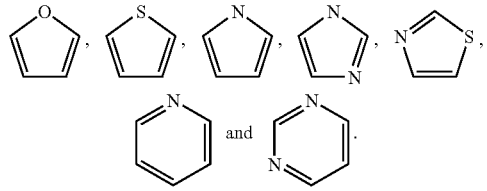

The "bicyclic aliphatic saturated hydrocarbon group" in the Formula (I) refers to an alicyclic saturated hydrocarbon group having two rings which have two or more atoms in common, and examples of the "bicylcic aliphatic saturated hydrocarbon group" in the Formula (I) include the following:

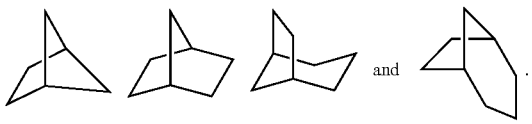

The "halogen atom" in the Formula (I) may be exemplified by a fluorine atom, a chlorine atom, a bromine atom, an iodine atom or the like, and among these, for example, a fluorine atom, a chlorine atom and a bromine atom are preferred, with the chlorine atom being more preferred.

The term "Cdk" indicates a cyclin-dependent kinase such as Cdk2, Cdc2 (=Cdk1), Cdk4, Cdk5, Cdk6, Cdk7, Cdk9 or the like. Here, Cdk2 is cyclin-dependent kinase 2; Cdc2 is a cell division cycle 2; Cdk1 is cyclin-dependent kinase 1; Cdk4 is cyclin-dependent kinase 4; Cdk5 is cyclin-dependent kinase 5; Cdk 6 is cyclin-dependent kinase 6; Cdk7 is cyclin-dependent kinase 7; and Cdk9 is cyclin-dependent kinase 9.

The term "Cdk inhibitor" is an inhibitor of cylcin-dependent kinase such as Cdk2, Cdc2, Cdk4, Cdk5, Cdk6, Cdk7, Cdk9, or the like.

The term "selective inhibitor against Cdk4 and/or Cdk6" refers to a compound exhibiting a selective inhibitory activity against Cdk4 and/or Cdk6 rather than Cdc2, Cdk5, Cdk7 or Cdk9, or a composition containing the compound.

The terms "pharmaceutically acceptable salt or ester" and "pharmaceutically acceptable carrier or diluent" will be explained later.

Embodiments of the compound represented by the Formula (I) will be described in more detail.

X is O, S, NH or $CH_2$, and preferably O, S or NH.

$Y_1, Y_2, Y_3, Y_4$ and $Y_5$, which may be identical or different, are each CH or N; however, at least one of $Y_1, Y_2, Y_3, Y_4$ and $Y_5$ is N. Preferably, $Y_1$ is N; $Y_2, Y_3$ and $Y_5$ are each CH; and $Y_4$ is CH or N.

$Z_1$ and $Z_2$, which may be identical or different, are each CH or N, and preferably, $Z_1$ and $Z_2$ are all N.

n is an integer from 1 to 3, and preferably 1.

$R_1$ is a $C_3$-$C_8$ cycloalkyl group, a $C_6$-$C_{10}$ aryl group, an aliphatic heterocyclic group or aromatic heterocyclic group selected from the group consisting of:

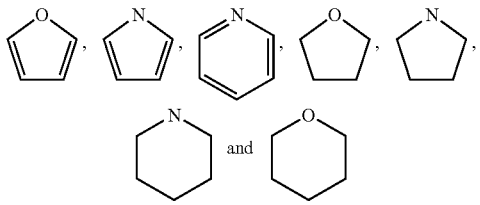

(hereinafter, this group is referred to as "Substituent Group $\alpha_1$"), or a bicyclic aliphatic saturated hydrocarbon group selected from the group consisting of:

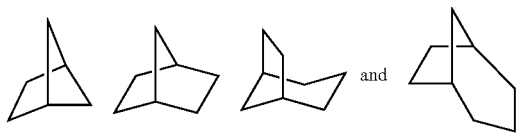

(hereinafter, this group is referred to as "Substituent Group $\alpha_2$"), wherein the cycloalkyl group, aryl group, aliphatic heterocyclic group or aromatic heterocyclic group, or bicyclic aliphatic saturated hydrocarbon group may be substituted with one or more of identical or different substituents selected from the following 1) to 3):

1) a lower alkyl group, 2) a substituent selected from the group consisting of a halogen atom, OH, OR, $CF_3$, CN, $NH_2$, NHR, $NR_aR_b$, NHCOR, $NR_aCOR_b$, $NHCO_2R$, $NR_aCO_2R_b$, NHCONHR, $NHSO_2R$, $CONH_2$, CONHR, $CONR_aR_b$, COR, $COCF_3$, $CO_2R$, OCOR, $OCO_2R$, $OCONR_aR_b$, $SO_3R$, $SO_2NH_2$, $SO_2NHR$, and $SO_2NR_aR_b$, wherein R, $R_a$ and $R_b$, which may be identical or different, are each a lower alkyl group (hereinafter, this group is referred to as "Substituent Group β"), and 3) a lower alkyl group substituted with a substituent selected from the "Substituent Group β".

Here, when $R_1$ is an aliphatic heterocyclic group or aromatic heterocyclic group selected from the "Substituent Group $\alpha_1$", $R_1$ is bound to the adjacent X through an atom capable of binding (a carbon atom or a nitrogen atom) in the aliphatic heterocyclic group or in the aromatic heterocyclic group. When a carbon atom in the aliphatic heterocyclic group or aromatic heterocyclic group is bound to X, the nitrogen atom in the corresponding ring may appropriately represent NH. Examples of the bonding forms in the aliphatic heterocyclic group or aromatic heterocyclic group selected from the "Substituent Group $\alpha_1$" include the following, but are not limited thereto.

Examples of bonding forms of "Substituent Group $\alpha_1$":

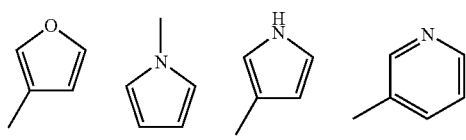
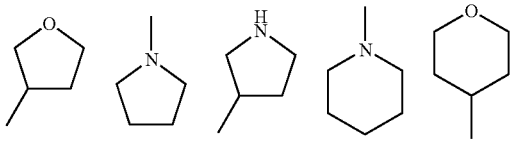

Furthermore, examples of the bonding forms of the bicyclic aliphatic saturated hydrocarbon group selected from the "Substituent Group $\alpha_2$" include the following, but are not limited thereto.

Examples of bonding forms of "Substituent Group $\alpha_2$":

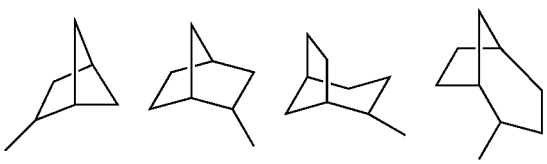

$R_1$ is preferably a $C_5$-$C_6$ cycloalkyl group, a phenyl group or an aliphatic heterocyclic group selected from the group consisting of:

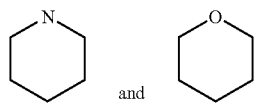

(hereinafter, this group is referred to as "Substituent Group $\alpha_{1A}$").

$R_1$ is more preferably a cyclohexyl group, a cyclopentyl group, or a 2-chlorophenyl group.

$R_2$ and $R_3$, which may be identical or different, are each a hydrogen atom, a lower alkyl group, a lower alkenyl group, a $C_3$-$C_8$ cycloalkyl group, a $C_6$-$C_{10}$ aryl group, an aromatic heterocyclic group selected from the group consisting of:

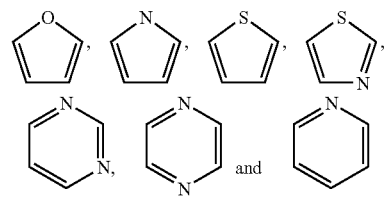

(hereinafter, this group is referred to as "Substituent Group $\alpha_3$"), or a substituent selected from the "Substituent Group β", wherein the lower alkyl group, lower alkenyl group, cycloalkyl group, aryl group or aromatic heterocyclic group may be substituted with one or more of identical or different substituents selected from the substituents selected from the "Substituent Group β".

Here, when $R_2$ and/or $R_3$, which may be identical or different, is an aromatic heterocyclic group selected from the "Substituent Group $\alpha_3$", $R_2$ and/or $R_3$ is bound to the adjacent ring through an atom capable of binding (a carbon atom or a nitrogen atom) in the aromatic heterocyclic group. When a carbon atom in the aromatic heterocyclic group is bound to the adjacent ring, the nitrogen atom in the aromatic heterocyclic group may appropriately represent NH. Examples of the bonding forms of the aromatic heterocyclic group selected from the "Substituent Group α₃" include the following, but are not limited thereto.

Examples of bonding forms of "Substituent Group α₃":

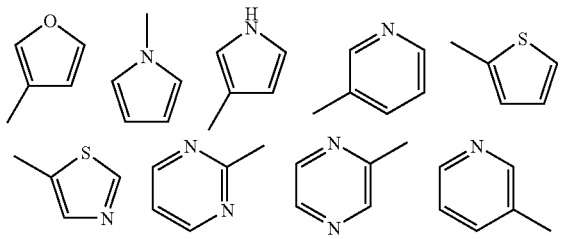

R₂ and R₃, which may be identical or different, are each preferably a hydrogen atom or a methyl group, provided that at least one of R₂ and R₃ is a methyl group. It is particularly preferable if any one between R₂ and R₃ is a hydrogen atom, while the other is a methyl group, in the aspect of selective inhibitory activity against Cdk4 and/or Cdk6.

R₄ is a hydrogen atom, a lower alkyl group, a $C_{3-6}$ cycloalkyl group, a substituent selected from the "Substituent Group β", or —W₁—W₂, wherein:

W₁ is any one selected from the following:

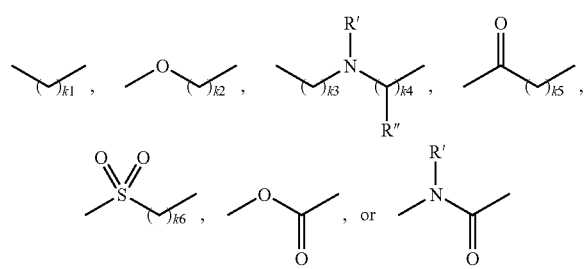

wherein k₁ is an integer from 0 to 5; k₂, k₄, k₅ and k₆, which may be identical or different, are each an integer from 0 to 4; k₃ is an integer of 0 or 1; and R' and R", which may be identical or different", are each a hydrogen atom or a lower alkyl group;

W₂ is a hydrogen atom, a lower alkyl group, a $C_3$-$C_8$ cycloalkyl group, a substituent selected from the "Substituent Group β", a $C_6$-$C_{10}$ aryl group, an aliphatic heterocyclic group selected from the group consisting of:

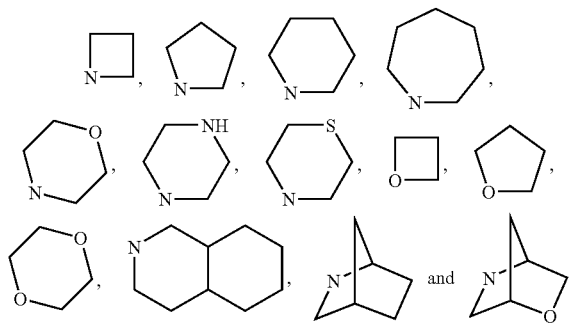

(hereinafter, this group is referred to as "Substituent Group γ₁"), or an aromatic heterocyclic group selected from the group consisting of:

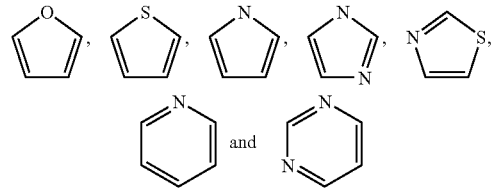

(hereinafter, this group is referred to as "Substituent Group γ₂"), wherein the lower alkyl group, cycloalkyl group, aryl group, aliphatic heterocyclic group or aromatic heterocyclic group may be substituted with one or more of identical or different substituents selected from the following 1) to 6):

1) a lower alkyl group,
2) a $C_3$-$C_6$ cycloalkyl group,
3) a substituent selected from the "Substituent Group β",
4) a lower alkyl group substituted with a substituent selected from the "Substituent Group β",
5) a substituent selected from the group consisting of:

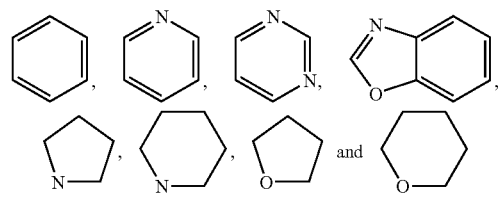

(hereinafter, this group is referred to as "Substituent Group δ"), and 6) a lower alkyl group substituted with a substituent selected from the "Substituent Group δ", and if W₂ is a lower alkyl group, any of the carbon atoms in the alkyl group may form a spiro-heterocyclic ring; and if W₁ is

and k₁ is 0, W₂ is not a substituent selected from the "Substituent Group β".

Here, when R₄ is —W₁—W₂, and W₂ is an aliphatic heterocyclic group selected from the "Substituent Group γ₁" or an aromatic heterocyclic group selected from the "Substituent Group γ₂", W₂ is bound to the adjacent W₁ through an atom capable of binding (a carbon atom or a nitrogen atom) in the aliphatic heterocyclic group or the aromatic heterocyclic group. When a carbon atom in the aliphatic heterocyclic group or the aromatic heterocyclic group is bound to the adjacent W₁, the nitrogen atom in the corresponding ring may appropriately represent NH. It is also contemplated that the same applies to the case of "Substituent Group δ". Examples of the bonding forms of the aliphatic heterocyclic group selected from the "Substituent Group γ₁" include the following, but are not limited thereto.

Examples of bonding form of "Substituent Group $\gamma_1$":

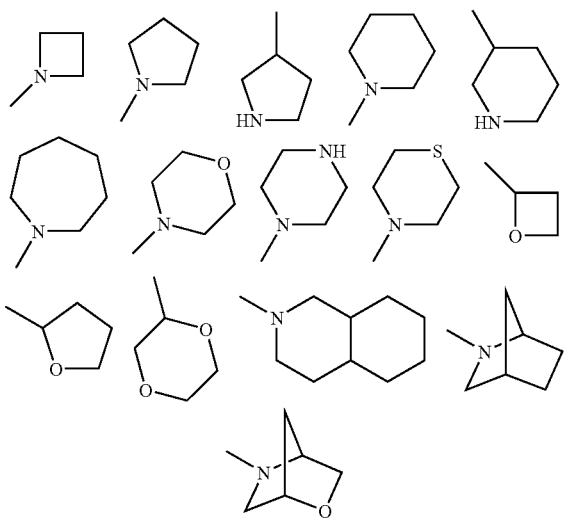

Furthermore, examples of the bonding forms of the aromatic heterocyclic group selected from the "Substituent Group $\gamma_2$" include the following, but are not limited thereto.

Examples of bonding form of "Substituent Group $\gamma_2$":

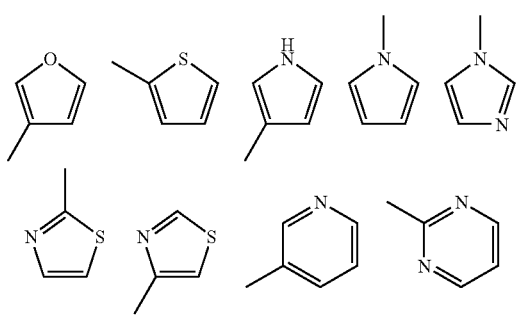

Moreover, examples of the bonding forms of the substituent selected from the "Substituent Group $\delta$" include the following, but are not limited thereto.

Examples of bonding form of "Substituent Group $\delta$":

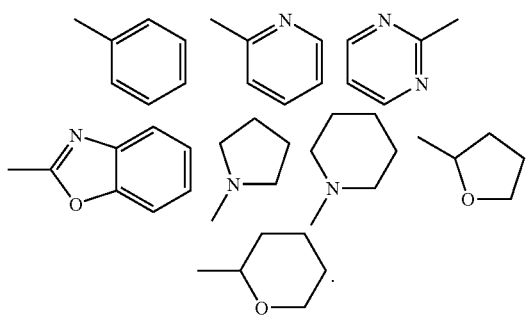

The substitution position of $R_4$ is preferably the 4-position, 5-position or 6-position, and is preferably the 4-position or 5-position.

$R_4$ is preferably a hydrogen atom; a substituent selected from the group consisting of a halogen atom, OH, $CF_3$, $NH_2$, NHR, $NR_aR_b$, NHCOR, CONHR, $CONR_aR_b$, COR and $CO_2R$, wherein R, $R_a$ and $R_b$, which may be identical or different, are each a lower alkyl group (hereinafter, this group is referred to as "Substituent Group $\beta_A$"); or $-W_1-W_2$, wherein:

$W_1$ is any one selected from the following;

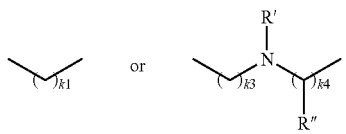

wherein $k_1$ is 0 or 1; $k_3$ is 1; $k_4$ is 0, 1 or 2; and R' and R", which may be identical or different, are each a hydrogen atom or a methyl group;

$W_2$ is a lower alkyl group, a $C_3$-$C_6$ cycloalkyl group, a substituent selected from the "Substituent Group $\beta_A$", an aliphatic heterocyclic group selected from the group consisting of:

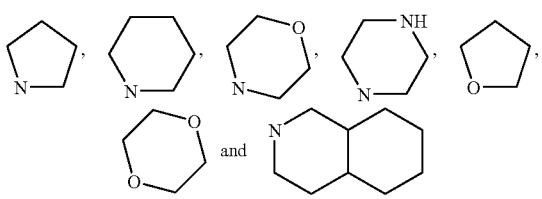

wherein two hydrogen atoms binding to the same carbon atom which constitutes the aliphatic heterocyclic group may together form an oxo group (hereinafter, this group is referred to as "Substituent Group $\gamma_{1A}$"), or an aromatic heterocyclic group selected from the group consisting of:

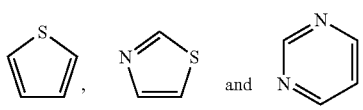

(hereinafter, this group is referred to as "Substituent Group $\gamma_{2A}$").

$R_4$ is more preferably $-W_1-W_2$ substituted at the 4-position, 5-position or 6-position wherein $W_1$ is

$k_1$ is 0 or 1; and $W_2$ is a 4-methyl-1-piperazinyl group, a 4-acetyl-1-piperazinyl group, a methylamino group, a dimethylamino group, a 1-pyrrolidinyl group, a 1-piperidinyl group, a 4-hydroxy-1-piperidinyl group, a 3-hydroxy-1-pyrrolidinyl group, a 3-dimethylamino-1-pyrrolidinyl group, a 2-hydroxymethyl-1-pyrrolidinyl group, a (2-hydroxyethyl)methylamino group, an ethylamino group, an isopropylamino group, or a hydroxyethylamino group.

The "Substituent Group α₁" preferably is:

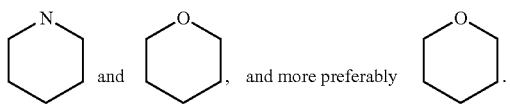

The "Substituent Group α₂" preferably is:

The "Substituent Group β" preferably is:
a halogen atom, OH, CF₃, NH₂, NHR, NR$_a$R$_b$, NHCOR, CONHR, CONR$_a$R$_b$, COR and CO₂R wherein R, R$_a$ and R$_b$, which may be identical or different, are each a lower alkyl group; more preferably OH or NR$_a$R$_b$; and particularly preferably OH or N(CH₃)₂.

The "Substituent Group γ₁" preferably is:

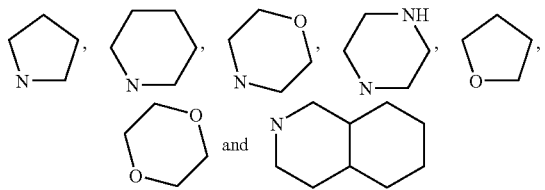

wherein two hydrogen atoms binding to the same carbon atom which constitute the aliphatic heterocyclic group may together form an oxo group; and more preferably a pyrrolidinyl group and a piperazinyl group.

The "Substituent Group γ₂" preferably is:

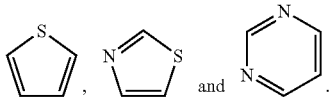

The "Substituent Group δ" preferably is:

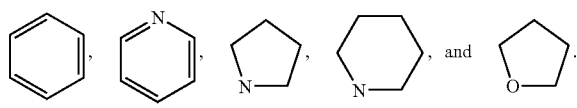

Preferred examples of X—R₁, include a cyclopentyloxy group, a cyclohexyloxy group, a cyclohexylthio group, a cyclohexylamino group, a 2-chlorophenyloxy group, and a 2-chlorophenylthio group, and more preferably, a cyclohexyloxy group, a cyclohexylamino group and a 2-chlorophenylthio group.

Preferred examples of R₄ include a (4-methyl-1-piperazinyl)methyl group, a (4-acetyl-1-piperazinyl)methyl group, an (ethylamino)methyl group, an (isopropylamino)methyl group, a (3-dimethylamino-1-pyrrolidinyl)methyl group, a (1-pyrrolidinyl)methyl group, a (2-hydroxyethylamino)methyl group, a (3-dimethylamino-1-pyrrolidinyl)methyl group, a (2-hydroxymethyl-1-pyrrolidinyl)methyl group, a (1-pyrrolidinyl)methyl group, a (3-hydroxy-1-pyrrolidinyl)methyl group, a (2-hydroxymethyl-1-pyrrolidinyl)methyl group, a [(2-hydroxyethyl)methylamino]methyl group, an (isopropylamino)methyl group, and an (ethylamino)methyl group, and more preferably, a (4-methylpiperazinyl)methyl group, a (3-hydroxy-1-pyrrolidinyl)methyl group and an (ethylamino) methyl group.

Among the compounds represented by Formula [I], preferred compounds are 5-[2-(cyclohexyloxy)-6-methyl-4-pyrimidinyl]-2-[5-(4-methyl-1-piperazinyl)methyl-2-pyrazinyl]amino-1,3-thiazole (Example 1), 5-[2-(cyclohexyloxy)-6-methyl-4-pyrimidinyl]-2-[5-(3-dimethylamino-1-pyrrolidinyl)methyl-2-pyrazinyl]amino-1,3-thiazole (Example 13), 5-[2-(cyclohexylamino)-6-methyl-4-pyrimidinyl]-2-[5-(ethylamino)methyl-2-pyrazinyl]amino-1,3-thiazole (Example 52), 5-[2-(cyclohexylamino)-6-methyl-4-pyrimidinyl]-2-[5-(4-methyl-1-piperazinyl)methyl-2-pyrazinyl]amino-1,3-thiazole (Example 55), 5-[2-(cyclohexylthio)-6-methyl-4-pyrimidinyl]-2-[5-(1-pyrrolidinyl)methyl-2-pyrazinyl]amino-1,3-thiazole (Example 93), 5-[2-(cyclohexylthio)-6-methyl-4-pyrimidinyl]-2-[5-(3-dimethylamino-1-pyrrolidinyl)methyl-2-pyrazinyl]amino-1,3-thiazole (Example 94), 5-[2-(cyclohexylthio)-6-methyl-4-pyrimidinyl]-2-[5-(isopropylamino)methyl-2-pyrazinyl]amino-1,3-thiazole (Example 96), 5-[2-(cyclohexylthio)-6-methyl-4-pyrimidinyl]-2-[5-(2-hydroxyethylamino)methyl-2-pyrazinyl]amino-1,3-thiazole (Example 99), 5-[2-(2-chlorophenylthio)-6-methyl-4-pyrimidinyl]-2-[5-(ethylamino)methyl-2-pyrazinyl]amino-1,3-thiazole (Example 105), 5-[2-(2-chlorophenylthio)-6-methyl-4-pyrimidinyl]-2-[5-(isopropylamino)methyl-2-pyrazinyl]amino-1,3-thiazole (Example 106), 5-[2-(2-chlorophenylthio)-6-methyl-4-pyrimidinyl]-2-[5-(4-methyl-1-piperazinyl)methyl-2-pyrazinyl]amino-1,3-thiazole (Example 109), (2S)-5-[2-(2-chlorophenylthio)-6-methyl-4-pyrimidinyl]-2-[5-(2-hydroxymethyl-1-pyrrolidinyl)methyl-2-pyrazinyl]amino-1,3-thiazole (Example 110), 5-[2-(2-chlorophenylthio)-6-methyl-4-pyrimidinyl]-2-[5-(1-pyrrolidinyl)methyl-2-pyrazinyl]amino-1,3-thiazole (Example 113), 5-[2-(2-chlorophenylthio)-6-methyl-4-pyrimidinyl]-2-{5-[(2-hydroxyethyl)methylamino]methyl-2-pyrazinyl}amino-1,3-thiazole (Example 114), (3R)-5-[2-(2-chlorophenylthio)-6-methyl-4-pyrimidinyl]-2-[5-(3-hydroxy-1-pyrrolidinyl)methyl-2-pyrazinyl]amino-1,3-thiazole (Example 118), 5-[2-(cyclohexyloxy)-6-methyl-4-pyrimidinyl]-2-[5-(4-acetyl-1-piperazinyl)methyl-2-pyridyl]amino-1,3-thiazole (Example 125), and (2S)-5-[2-(cyclohexylamino)-6-methyl-4-pyrimidinyl]-2-[5-(2-hydroxymethyl-1-pyrrolidinyl)methyl-2-pyridyl]amino-1,3-thiazole (Example 137).

Next, the preferred form of the present invention can be expressed as follows:

(1) A compound of Formula (I), or a pharmaceutically acceptable salt or ester thereof, wherein Y₁ is N; Y₂, Y₃ and Y₅ are each CH; Y₄ is CH or N; and Z₁ and Z₂ are each N; or (2) The compound according to (1) above, or a pharmaceutically acceptable salt or ester thereof, wherein X is O, S or NH; and R₁ is a C₅-C₆ cycloalkyl group, a phenyl group, or an aliphatic heterocyclic group selected from the "Substituent Group α₁", wherein the "Substituent Group α₁" is

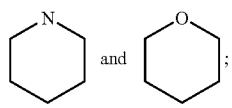

or (3) The compound according to (2) above, or a pharmaceutically acceptable salt or ester thereof, wherein $R_2$ and $R_3$, which may be identical or different, are each a hydrogen atom or a methyl group, provided that at least one of $R_2$ and $R_3$ is a methyl group; or (4) The compound according to (3) above, or a pharmaceutically acceptable salt or ester thereof, wherein the substitution position of $R_4$ is the 4-position, 5-position or 6-position; and n is 1; or (5) The compound according to (4) above, or a pharmaceutically acceptable salt or ester thereof, wherein the "Substituent Group β" is:

a halogen atom, OH, $CF_3$, $NH_2$, NHR, $NR_aR_b$, NHCOR, CONHR, $CONR_aR_b$, COR and $CO_2R$, wherein R, $R_a$ and $R_b$, which may be identical or different, are each a lower alkyl group; or (6) The compound according to (5) above, or a pharmaceutically acceptable salt or ester thereof, wherein the "Substituent Group $\gamma_1$" is:

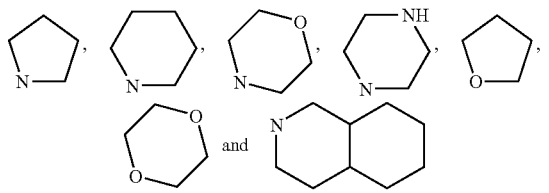

wherein two hydrogen atoms binding to the same carbon atom which constitutes the aliphatic heterocyclic group may together form an oxo group, and the "Substituent Group $\gamma_2$" is:

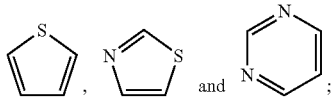

or (7) The compound according to (6) above, or a pharmaceutically acceptable salt or ester thereof, wherein $R_4$ is a hydrogen atom, a substituent selected from the "Substituent Group β", or $-W_1-W_2$ wherein:

$W_1$ is any one selected from the following:

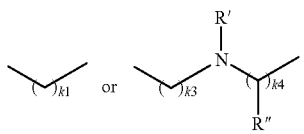

wherein $k_1$ is 0 or 1; $k_3$ is 1; $k_4$ is 0, 1 or 2; and R' and R", which may be identical or different, are each a hydrogen atom or a methyl group; and $W_2$ is a lower alkyl group, a $C_3$-$C_6$ cycloalkyl group, a substituent selected from the "Substituent Group β", an aliphatic heterocyclic group selected from the "Substituent Group $\gamma_1$", or an aromatic heterocyclic group selected from the "Substituent Group $\gamma_2$"; or (8) The compound according to (1) above, or a pharmaceutically acceptable salt or ester thereof, wherein:

X is O, S or NH;

$R_1$ is a cyclohexyl group, a cyclopentyl group, or a 2-chlorophenyl group;

one of $R_2$ and $R_3$ is a hydrogen atom, while the other is a methyl group;

$R_4$ is $-W_1-W_2$ substituted at the 4-position, 5-position or 6-position, wherein $W_1$ is:

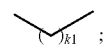

$k_1$ is 0 or 1; and $W_2$ is 4-methyl-1-piperazinyl group, 4-acetyl-1-piperazinyl group, methylamino group, dimethylamino group, 1-pyrrolidinyl group, 1-piperidinyl group, 4-hydroxy-1-piperidinyl group, 3-hydroxy-1-pyrrolidinyl group, 3-dimethylamino-1-pyrrolidinyl group, 2-hydroxymethyl-1-pyrrolidinyl group, (2-hydroxyethyl)methylamino group, ethylamino group, isopropylamino group, or hydroxyethylamino group.

Next, the processes for producing the compound of Formula (I) will be described in the following.

A process for producing the compound represented by Formula (I):

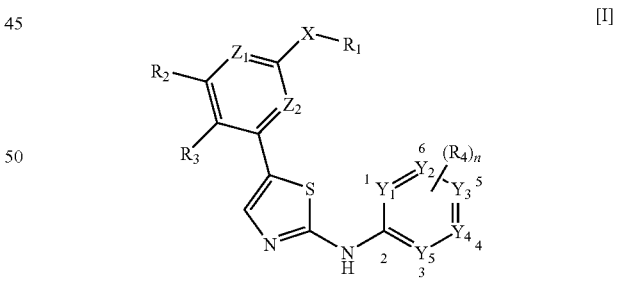

[I]

wherein X, $Y_1$ through $Y_5$, $Z_1$ and $Z_2$, n, $R_1$ through $R_4$, R, $R_a$, $R_b$, "Substituent Group $\alpha_1$", "Substituent Group $\alpha_2$", "Substituent Group $\alpha_3$", "Substituent Group β", "Substituent Group $\gamma_1$", "Substituent Group $\gamma_2$" and "Substituent Group δ" have the same meaning as defined above, will be described.

The compound represented by the above Formula (I) can be obtained by eliminating a protective group $PG_1$ from a compound represented by the following Formula (II) or Formula (III):

[II]

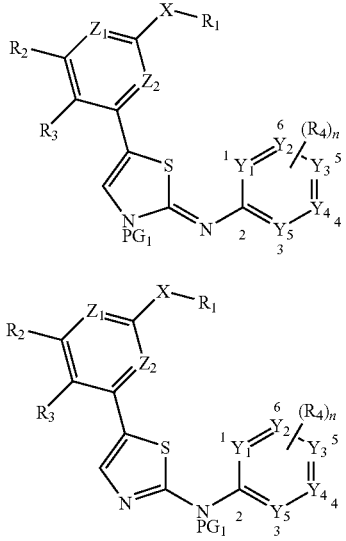

[III]

wherein X, $Y_1$ through $Y_5$, $Z_1$ and $Z_2$, n, $R_1$ through $R_4$, R, $R_a$, $R_b$, "Substituent Group $\alpha_1$", "Substituent Group $\alpha_2$", "Substituent Group $\alpha_3$", "Substituent Group $\beta$", "Substituent Group $\gamma_1$", "Substituent Group $\gamma_2$" and "Substituent Group $\beta$" have the same meaning as defined above; and $PG_1$ represents a protective group.

Here, $PG_1$ may be exemplified by a 4-methoxybenzyl group, a 2,4-dimethoxybenzyl group, a benzyl group, a t-butyl group, a methoxymethyl group, a 2-(trimethylsilylethoxy) methyl group, an acetyl group, a benzoyl group, a methanesulfonyl group or the like, and preferably, a 2-(trimethylsilylethoxy)methyl group, a methoxymethyl group or the like. Elimination of the protective group may be performed differently in accordance with the type of the protective group and stability of the compound, but can be performed by, for example, solvolysis using an acid, according to the method described in the literature [See T. W. Greene, Protective Groups in Organic Synthesis, John Wiley & Sons (1981)] or a method equivalent thereto.

Next, a process for producing the compound represented by the above Formula (II) or Formula (III) will be described. The compound represented by the Formula (II) or Formula (III), wherein X is O or S; and $R_1$ is an alkyl group, including a $C_3$-$C_8$ cycloalkyl group, can be obtained from a compound represented by the following Formula (IV) or Formula (V):

[IV]

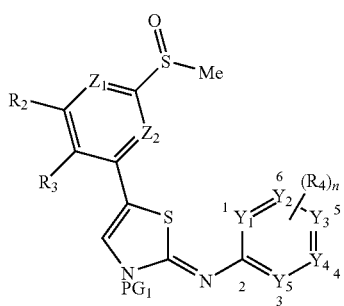

[V]

wherein $Y_1$ through $Y_5$, $Z_1$ and $Z_2$, n, $R_2$ through $R_4$, R, $R_a$, $R_b$, "Substituent Group $\alpha_3$", "Substituent Group $\beta$", "Substituent Group $\gamma_1$", "Substituent Group $\gamma_2$" and "Substituent Group $\delta$" have the same meaning as defined above; and $PG_1$ represents a protective group, by a substitution reaction with a corresponding alcohol product (X=O) or a thiol product (X=S). For example, the compound represented by the Formula (II) or Formula (III) can be synthesized by reacting the compound represented by the Formula (IV) or (V) with sodium alkoxide or sodium thiolate, in a solvent such as tetrahydrofuran, dimethylformamide, 1,4-dioxane or the like, preferably in tetrahydrofuran. In this case, the reaction temperature can be appropriately selected by those having ordinary skill in the art, in accordance with the starting compound used or the reaction solvent, but the reaction temperature is usually a temperature from 0° C. to room temperature. The reaction is usually completed in 1 to 24 hours, but the duration of the reaction can be appropriately increased or decreased.

The compound represented by the Formula (II) or Formula (III), wherein X is O or S; and $R_1$ is a $C_6$-$C_{10}$ aryl group or an aromatic heterocyclic group, can be also synthesized by a substitution reaction between the compound represented by the Formula (IV) or Formula (V) and a corresponding phenol product (X=O) or a thiophenol product (X=S). For example, the compound represented by the Formula (II) or Formula (III) can be synthesized by reacting the compound represented by the Formula (IV) or Formula (V) with a phenol product (X=O) or a thiophenol product (X=S), in a solvent such as tetrahydrofuran, dimethylformamide, 1,4-dioxane, dimethylsulfoxide or the like, preferably in dimethylformamide, and in the presence of a base such as potassium carbonate or the like. In this case, the reaction temperature can be appropriately selected by those having ordinary skill in the art in accordance with the starting compound used or the reaction solvent, but the reaction temperature is usually a temperature from 80° C. to the boiling point of the solvent, preferably at 80° C. The reaction is usually completed in 1 to 24 hours, but the duration of the reaction can be appropriately increased or decreased.

Furthermore, the compound represented by the above Formula (II) or Formula (III), wherein X is NH; and $R_1$ is an alkyl group, including a $C_3$-$C_8$ cycloalkyl group, can be obtained by a substitution reaction between the compound represented by the above Formula (IV) or Formula (V) with a corresponding amine product (X=N). For example, the compound represented by the Formula (II) or Formula (III) can be synthesized by reacting the compound represented by the Formula (IV) or Formula (V) with an amine product (X=N) in a solvent such as tetrahydrofuran, dimethylformamide, 1,4-dioxane, dimethylsulfoxide or the like, preferably in dimethylsulfoxide. In this case, the reaction temperature can be appropriately selected by those having ordinary skill in the art in accordance with the starting compound used or the reaction solvent, but the reaction temperature is usually from 80° C. to the boiling point of the solvent. The reaction is usually completed in 1 to 24 hours, but the duration of the reaction can be appropriately increased or decreased.

In addition, the compound represented by the Formula (II) or Formula (III) can be also synthesized in the same manner under the same conditions as described above, but using a compound represented by the following Formula (IV-I) or Formula (V-I):

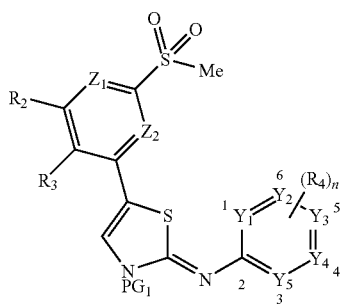

[IV-I]

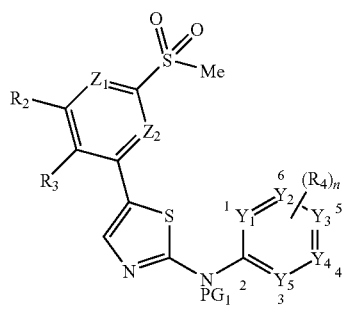

[V-1]

wherein $Y_1$ through $Y_5$, $Z_1$ and $Z_2$, n, $R_2$ through $R_4$, R, $R_a$, $R_b$, "Substituent Group $\alpha_3$", "Substituent Group $\beta$", "Substituent Group $\gamma_1$", "Substituent Group $\gamma_2$" and "Substituent Group $\delta$" have the same meaning as defined above; and $PG_1$ represents a protective group.

Next, a process for producing the compound represented by the above Formula (IV) or Formula (V) will be described.

The compound represented by the Formula (IV) or Formula (V) can be synthesized by oxidizing a compound represented by the following Formula (VI) or Formula (VII):

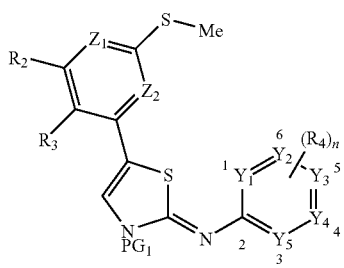

[VI]

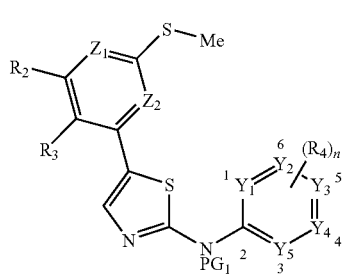

[VII]

wherein $Y_1$ through $Y_5$, $Z_1$ and $Z_2$, n, $R_2$ through $R_4$, R, $R_a$, $R_b$, "Substituent Group $\alpha_3$", "Substituent Group $\beta$", "Substituent Group $\gamma_1$", "Substituent Group $\gamma_2$" and "Substituent Group $\delta$" have the same meaning as defined above; and $PG_1$ represents a protective group, with m-chloroperbenzoic acid (mCPBA) in a solvent such as methylene chloride, chloroform or the like. In this case, the reaction temperature can be appropriately selected by those having ordinary skill in the art in accordance with the starting compound used or the reaction solvent, but the reaction temperature is usually from 0° C. to room temperature, preferably at 0° C. The reaction is usually completed in 1 to 24 hours, but the duration of the reaction can be appropriately increased or decreased.

The compound represented by the above Formula (IV-I) or Formula (V-I) can be synthesized by oxidizing the compound represented by the Formula (VI) or Formula (VII) with hydrogen peroxide and sodium tungstate (VI) dihydrate in a solvent such as methanol, ethanol, THF, 1,4-dioxane or the like. In this case, the reaction temperature can be appropriately selected by those having ordinary skill in the art in accordance with the starting compound used or the reaction solvent, but the reaction temperature is usually from 0° C. to room temperature, preferably at room temperature. The reaction is usually completed in 12 to 24 hours, but the duration of the reaction can be appropriately increased or decreased.

Next, a process for producing the compound represented by the above Formula (VI) or Formula (VII) will be described.

The compound represented by the Formula (VI) or Formula (VII) can be synthesized from a compound represented by the following Formula (VIII):

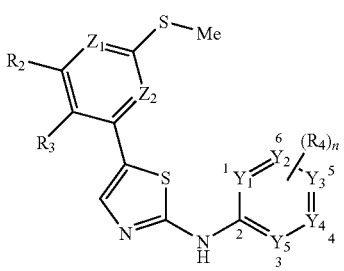

[VIII]

wherein $Y_1$ through $Y_5$, $Z_1$ and $Z_2$, n, $R_2$ through $R_4$, R, $R_a$, $R_b$, "Substituent Group $\alpha_3$", "Substituent Group $\beta$", "Substituent Group $\gamma_1$", "Substituent Group $\gamma_2$" and "Substituent Group $\delta$" have the same meaning as defined above, using chloromethyl methyl ether, chloromethyl 2-trimethylsilylethyl ether, acetyl chloride, methanesulfonyl chloride or the like, and a base such as triethylamine, diisopropylethylamine, sodium hydride or the like, in a solvent such as methylene chloride, chloroform, THF, 1,4-dioxane, DMF or the like. In this case, the reaction temperature can be appropriately selected by those having ordinary skill in the art in accordance with the starting compound used or the reaction solvent, but the reaction temperature is usually from 0° C. to room temperature. The reaction is usually completed in 1 to 12 hours, but the duration of the reaction can be appropriately increased or decreased. Here, when an organic base such as diisopropylethylamine or the like is used as the base, production of the compound of Formula (VI) occurs preferentially to the production of the compound of Formula (VII), whereas when an inorganic base such as sodium hydride or the like is used, the compound of Formula (VI) and the compound of Formula (VII) are produced in almost equal amounts.

Next, a process for producing the compound represented by the above Formula (VIII) will be described.

The compound represented by the Formula (VIII) can be synthesized from compounds represented by the following Formula (IX) and Formula (X):

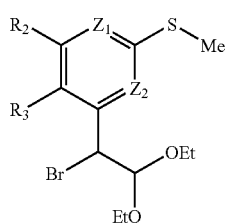

[IX]

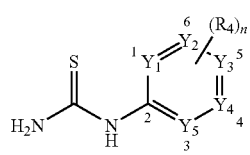

[X]

wherein $Y_1$ through $Y_5$, $Z_1$ and $Z_2$, n, $R_2$ through $R_4$, R, $R_a$, $R_b$, "Substituent Group $\alpha_3$", "Substituent Group $\beta$", "Substituent Group $\gamma_1$", "Substituent Group $\gamma_2$" and "Substituent Group $\delta$" have the same meaning as defined above, using an acid such as p-toluenesulfonic acid or the like, in a mixed solvent of water and an organic solvent such as ethanol, methanol, THF, 1,4-dioxane or the like. In this case, the reaction temperature can be appropriately selected by those having ordinary skill in the art in accordance with the starting compound used or the reaction solvent, but the reaction temperature is usually from 80° C. to the boiling point of the solvent, preferably at 90° C. The reaction is usually completed in 12 to 24 hours, but the duration of the reaction can be appropriately increased or decreased.

Next, a process for producing the compound represented by the above Formula (IX) will be described.

The compound represented by the Formula (IX) can be synthesized by reacting a compound represented by the following Formula (XI):

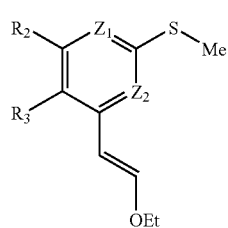

[XI]

wherein $Z_1$ and $Z_2$, $R_2$ and $R_3$, R, $R_a$, $R_b$, "Substituent Group $\alpha_3$", and "Substituent Group $\beta$" have the same meaning as defined above, with N-bromosuccinimide in ethanol. In this case, the reaction temperature can be appropriately selected by those having ordinary skill in the art in accordance with the starting compound used or the reaction solvent, but the reaction temperature is usually from 0° C. to room temperature, preferably at 0° C. The reaction is usually completed in 1 to 12 hours, but the duration of the reaction can be appropriately increased or decreased.

Next, a process for producing the compound represented by the above Formula (XI) will be described.

The compound represented by the Formula (XI) can be synthesized by reacting a compound represented by the following Formula (XII):

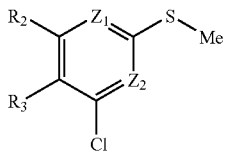

[XII]

wherein $Z_1$ and $Z_2$, $R_2$ and $R_3$, R, $R_a$, $R_b$, "Substituent Group $\alpha_3$", and "Substituent Group $\beta$" have the same meaning as defined above, with tris(2-ethoxyvinyl)boron and a base such as palladium acetate, triphenylphosphine, aqueous sodium hydroxide solution or the like, in a solvent such as THF, 1,4-dioxane, 1,2-dimethoxyethane or the like, preferably in THF. In this case, the reaction temperature can be appropriately selected by those having ordinary skill in the art in accordance with the starting compound used or the reaction solvent, but the reaction temperature is usually from room temperature to the boiling point of the solvent, preferably at room temperature. The reaction is usually completed in 1 to 24 hours, but the duration of the reaction can be appropriately increased or decreased.

Next, a process for producing the compound represented by the above Formula (XII) will be described.

The compound represented by the Formula (XII), wherein $R_2$ is not H; $R_3$ is H; and $Z_1$ and $Z_2$ are each N, can be synthesized by reacting a compound represented by the following Formula (XIII):

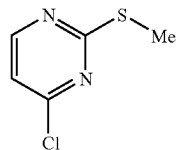

[XIII]

with a corresponding organometallic reagent (this is R$_2$M, wherein M=Li or Mgx, and X represents halogen), in a solvent such as THF, 1,4-dioxane, ether, 1,2-dimethoxyethane or the like, and then treating the resulting compound with 2,3-dichloro-5,6-dicyano-p-quinone. In this case, the reaction temperature can be appropriately selected by those having ordinary skill in the art in accordance with the starting compound used or the reaction solvent, but the reaction temperature is usually from −78° C. to room temperature, preferably at 0° C. The reaction is usually completed in 1 to 12 hours, but the duration of the reaction can be appropriately increased or decreased.

Here, the compound represented by the Formula (XIII) is commercially available.

The compound represented by the above Formula (XII), wherein Z$_1$ and Z$_2$ are each N; and R$_2$ and R$_3$, "Substituent Group α$_3$", and "Substituent Group β" have the same meaning as defined above, can be synthesized by reacting a compound represented by the following Formula (XIV):

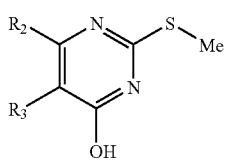

[XIV]

wherein R$_2$ and R$_3$, R, R$_a$, R$_b$, "Substituent Group α$_3$", and "Substituent Group β" have the same meaning as defined above, with phosphorus oxychloride. In this case, the reaction temperature can be appropriately selected by those having ordinary skill in the art in accordance with the starting compound used, but the reaction temperature is usually from room temperature to the boiling point of phosphorus oxychloride, preferably at the boiling point. The reaction is usually completed in 1 to 12 hours, but the duration of the reaction can be appropriately increased or decreased.

Next, a process for producing the compound represented by the above Formula (XIV) will be described.

The compound represented by the Formula (XIV) can be synthesized from a compound represented by the following Formula (XV) and a compound represented by the following Formula (XVI):

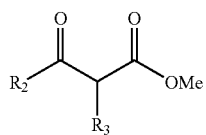

[XV]

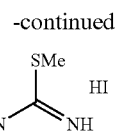

[XVI]

using a base such as aqueous sodium hydroxide solution in a solvent such as ethanol, methanol or the like. In this case, the reaction temperature can be appropriately selected by those having ordinary skill in the art in accordance with the starting compound used or the reaction solvent, but the reaction temperature is usually from room temperature to the boiling point of the solvent, preferably at the boiling point. The reaction is usually completed in 12 to 24 hours, but the duration of the reaction can be appropriately increased or decreased.

Here, the compound represented by the Formula (XV) is either a commercially available β-keto ester, or a compound that can be synthesized using the Claisen reaction of a commercial ester, or the like [See Jerry March, *Advanced Organic Chemistry*, Fourth Edition, Wiley Interscience, p. 1283]. The compound represented by the Formula (XVI) can be synthesized using a commercial thiourea and methyl iodide (J. Chem. Soc., 1937, 1699).

Next, a process for producing the compound represented by the above Formula (X) will be described.

The compound represented by the Formula (X) can be synthesized by reacting a compound represented by the following Formula (XVII):

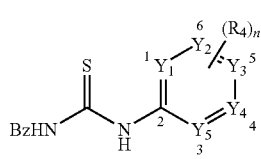

[XVII]

wherein Y$_1$ through Y$_5$, n, R$_4$, "Substituent Group β", "Substituent Group γ$_1$", "Substituent Group γ$_2$" and "Substituent Group δ" have the same meaning as defined above, and Bz is a benzoyl group, with a base such as aqueous sodium hydroxide solution, aqueous potassium carbonate solution or the like, in a solvent such as methanol, ethanol, THF, 1,4-dioxane or the like. In this case, the reaction temperature can be appropriately selected by those having ordinary skill in the art in accordance with the starting compound used or the reaction solvent, but the reaction temperature is usually from room temperature to the boiling point of the solvent. The reaction is usually completed in 1 to 24 hours, but the duration of the reaction can be appropriately increased or decreased.

Next, a process for producing the compound represented by the above Formula (XVII) will be described.

The compound represented by the Formula (XVII) can be synthesized by reacting a compound represented by the following Formula (XVIII):

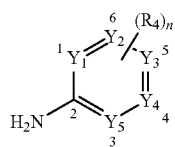

wherein Y₁ through Y₅, n, R₄, "Substituent Group β", "Substituent Group γ₁", "Substituent Group γ₂" and "Substituent Group δ" have the same meaning as defined above, with benzoyl isothiocyanate in a solvent such as THF, 1,4-dioxane or the like. In this case, the reaction temperature can be appropriately selected by those having ordinary skill in the art in accordance with the starting compound used or the reaction solvent, but the reaction temperature is usually from 0° C. to room temperature, preferably at room temperature. The reaction is usually completed in 1 to 24 hours, but the duration of the reaction can be appropriately increased or decreased.

The compound represented by the Formula (XVIII) is either commercially available, or can be synthesized using the Curtius rearrangement of a corresponding commercial carboxylic acid (J. Am. Chem. Soc., 1972, 6203) and a substitution reaction between a corresponding halogen and ammonia or an ammonia equivalent (Tetrahedron Lett., 38, 6367 (1997)), or using a reduction reaction of a corresponding nitro group.

Introduction or conversion of R₄ can be performed in several stages of the above-mentioned synthetic intermediates. Hereinafter, examples of the introduction or conversion of R in the compound represented by the Formula (II) or Formula (III) will be described. In addition, a person having ordinary skill in the art can perform the introduction or conversion of R₄ from commercially available, known compounds using appropriate known methods, and/or the method illustrated below or a method equivalent thereto.

The compound represented by the Formula (II) or Formula (III), wherein R is an alkoxycarbonyl group, can be synthesized from a corresponding compound represented by the Formula (II) or Formula (III), wherein R is a bromine atom. For example, the compound represented by the Formula (II) or Formula (III), wherein R is an alkoxycarbonyl group, can be synthesized by reacting a compound represented by the Formula (II) or Formula (III), wherein R is a bromine atom, with carbon monoxide, in a mixed solvent prepared by adding an alcohol such as methanol, ethanol or the like to a solvent such as N,N-dimethylacetamide, N-methylpyrrolidone, N,N-dimethylformamide or the like, in the presence of a ligand such as 1,1'-bis(diphenylphosphino)ferrocene or the like and a palladium catalyst such as palladium(II) acetate or the like, and a base such as sodium hydrogen carbonate, triethylamine or the like. In this case, the reaction temperature can be appropriately selected by those having ordinary skill in the art in accordance with the starting compound used or the reaction solvent, but the reaction temperature is usually from 50° C. to the boiling point of the solvent used in the reaction. The reaction is usually completed in 1 to 24 hours, but the duration of the reaction can be appropriately increased or decreased.

Furthermore, the compound represented by the Formula (I) or Formula (III), wherein R is a hydroxycarbonyl group, can be synthesized by a hydrolysis reaction of a corresponding compound represented by the Formula (II) or Formula (III), wherein R is an alkoxycarbonyl group. For example, the compound represented by the Formula (II) or Formula (III), wherein R is a hydroxycarbonyl group, can be synthesized from the compound represented by the Formula (II) or Formula (III), wherein R is an alkoxycarbonyl group, using aqueous sodium hydroxide solution or the like as a base, in a solvent such as methanol, ethanol, tetrahydrofuran or the like. In this case, the reaction temperature can be appropriately selected by those having ordinary skill in the art in accordance with the starting compound used or the reaction solvent, but the reaction temperature is usually from room temperature to the boiling point of the solvent. The reaction is usually completed in 1 to 24 hours, but the duration of the reaction can be appropriately increased or decreased.

The compound represented by the Formula (II) or Formula (III), wherein R is a hydroxymethyl group, can be also synthesized by a reduction reaction of a corresponding compound represented by the Formula (II) or Formula (III), wherein R is a hydroxycarbonyl group. For example, the compound represented by the Formula (II) or Formula (II), wherein R is a hydroxymethyl group, can be synthesized by reacting the compound represented by the Formula (II) or Formula (III), wherein R is a hydroxycarbonyl group, with N,N'-carbonyldiimidazole at room temperature for 12 to 24 hours in a solvent such as tetrahydrofuran or the like, and then reacting the resultant solution with a reducing agent such as sodium tetrahydroborate or the like. In this case, the reaction temperature can be appropriately selected by those having ordinary skill in the art in accordance with the starting compound used or the reaction solvent, but the reaction temperature is usually from 0° C. to room temperature. The reaction is usually completed in 10 minutes to 24 hours, but the duration of the reaction can be appropriately increased or decreased.

The compound represented by the Formula (II) or Formula (III), wherein R is a methanesulfonyloxymethyl group, can be obtained by reacting a compound represented by the Formula (II) or Formula (III), wherein R is a hydroxymethyl group, with methanesulfonyl chlorine in a solvent such as chloroform, methylene chloride, tetrahydrofuran, N,N-dimethylformamide, diethyl ether, ethyl acetate or the like, in the presence of an organic base such as triethylamine, diisopropylethylamine or the like. In this case, the reaction temperature can be appropriately selected by those having ordinary skill in the art in accordance with the starting compound used, but the reaction temperature is usually from 0° C. to room temperature. The reaction is usually completed in 1 to 2 hours, but the duration of the reaction can be appropriately increased or decreased.

Moreover, the compound represented by the Formula (II) or (III), wherein R is a (dialkyl)aminomethyl group or a (monoalkyl)aminomethyl group, can be synthesized by reacting a compound represented by the Formula (II) or Formula (III), wherein R is a methanesulfonyloxymethyl group, with a dialkylamine such as piperidine, morpholine, N-methylpiperazine, diethylamine or the like, or with a (monoalkyl)amine such as methylamine, isopropylamine or the like, in a solvent such as chloroform, methylene chloride, tetrahydrofuran, N,N-dimethylformamide or the like, in the presence of an inorganic base such as potassium carbonate or the like. In this case, the reaction temperature can be appropriately selected by those having ordinary skill in the art in accordance with the starting compound used or the reaction solvent, but the reaction temperature is usually from room temperature to the boiling point of the solvent used in the reaction. The reaction is usually completed in 1 to 24 hours, but the duration of the reaction can be appropriately increased or decreased.

The compound represented by the Formula (II) or Formula (III), wherein R is a dialkylamino group, can be synthesized from a corresponding compound represented by the Formula (II) or Formula (III), wherein R is a bromine atom. For example, the compound represented by the Formula (II) or Formula (III), wherein R is a dialkylamino group, can be synthesized by reacting a compound represented by the Formula (I) or Formula (III), wherein R is a bromine atom, with a dialkylamine such as N-methylpiperazine, N-Boc piperazine or the like, in a solvent such as toluene, 1,4-dioxane, N,N-dimethylformamide or the like, preferably in toluene, in the presence of a palladium catalyst such as palladium acetate or the like, a phosphine ligand such as (R)-(+)-2,2'-bis(diphenylphosphino)-1,1'-binaphthyl or the like, and a base such as sodium t-butoxide, cesium carbonate or the like. In this case, the reaction temperature can be appropriately selected by those having ordinary skill in the art in accordance with the starting compound used or the reaction solvent, but the reaction temperature is usually from room temperature to the boiling point of the solvent used in the reaction, preferably at 60° C. to 120° C. The reaction is usually completed in 1 to 24 hours, but the duration of the reaction can be appropriately increased or decreased.

Next, the Cdk inhibitory action of the compound of Formula (I) will be explained in the following.

Cdk4 Inhibitory Action (1) Purification of Cyclin D2-Cdk4

First, the cDNA of Cdk4, and the cDNA of a fusion protein of cyclin D2, an activating factor of Cdk4, and glutathione S-transferase, were integrated into a baculovirus expression vector to prepare a recombinant baculovirus. This was co-transfected into insect cell Sf9 to express an active complex of the cyclin D2/glutathione S-transferase fusion protein-Cdk4 at a high level. The cells were recovered and solubilized, then the active complex was adsorbed onto Glutathione Sepharose, and a cyclin D2-Cdk4 complex was recovered using Precision Protease and was purified by HPLC column chromatography [EMBO J., Vol. 15, 7060-7069 (1996)].

(2) Measurement of Cyclin D2-Cdk4 Activity

For the measurement of the activity of cyclin D2-Cdk4, a synthetic peptide (Arg-Pro-Pro-Thr-Leu-Ser-Pro-Ile-Pro-His-Ile-Pro-Arg) corresponding to amino acid residue No. 775-787 of RB protein was used as the substrate [EMBO J., Vol. 15, 7060-7069 (1996)].

The reaction was performed by partially modifying the method of Kitagawa et al. [Oncogene, Vol. 7, 1067-1074 (1992)]. The volume of the reaction solution was 21.1 µL, and the composition of the reaction buffer (R buffer) was 20 mM Tris-hydrochloric acid buffer (pH 7.4)/10 mM magnesium chloride/4.5 mM 2-mercaptoethanol/1 mM ethylene glycol bis(β-aminoethyl ether)-N,N,N',N'-tetraacetic acid (EGTA). To this reaction buffer, purified cyclin D2-Cdk4, 100 µM of the substrate peptide, 50 µM of non-labeled adenosine triphosphate (ATP), and 1 µCi of [γ-33P]-labeled ATP (2000 to 4000 Ci/mmole) were added to react at 30° C. for 45 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter. The [γ-33P]-labeled ATP was purchased from Daiichi Pure Chemicals Co., Ltd.

Addition of the test compound to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the cyclin D2-Cdk4 activity was determined. The results are presented in Table 1 below.

It is obvious from the results of Table 1 that the compound according to the invention has a strong inhibitory activity against cyclin D2-Cdk4.

Cdk6 Inhibitory Action (1) Purification of Cyclin D2-Cdk6

In the same manner as in the case of cyclin D2-Cdk4, the cDNA of Cdk6, and the cDNA of a fusion protein of cyclin D2, an activating factor of Cdk6, and glutathione S-transferase, were integrated into a baculovirus expression vector to prepare a recombinant baculovirus. This was co-transfected into insect cell Sf9 to express an active complex of the cyclin D2/glutathione S-transferase fusion protein-Cdk6 at a high level. The cells were recovered and solubilized, then the active complex was adsorbed onto Glutathione Sepharose, and a cyclin D2-Cdk6 complex was recovered using Precision Protease and was purified by HPLC column chromatography.

(2) Measurement of Cyclin D2-Cdk6 Activity

For the measurement of the activity of cyclin D2-Cdk6, a synthetic peptide (Arg-Pro-Pro-Thr-Leu-Ser-Pro-Ile-Pro-His-Ile-Pro-Arg) was used as the substrate.

The reaction was performed by partially modifying the method of Kitagawa et al. [Oncogene, Vol. 7, 1067-1074 (1992)]. The volume of the reaction solution was 21.1 µL, and to the R buffer, purified cyclin D2-Cdk6, 100 µM of the substrate peptide, 50 µM of non-labeled adenosine triphosphate (ATP), and 1 µCi of [γ-33P]-labeled ATP (2000 to 4000 Ci/mmole) were added to react at 30° C. for 40 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the cyclin D2-Cdk6 activity was determined. The results are presented in Table 1 below.

It is obvious from the results of Table 1 that the compound according to the invention has a strong inhibitory activity against cyclin D2-Cdk6.

Cdk2 Inhibitory Action (1) Purification of Cyclin A-Cdk2

In the same manner as in the case of cyclin D2-Cdk4, the cDNA of Cdk2, and the cDNA of a fusion protein of cyclin A, an activating factor of Cdk2, and glutathione S-transferase, were integrated into a baculovirus expression vector to prepare a recombinant baculovirus. This was co-transfected into insect cell Sf9 to express an active complex of the cyclin A/glutathione S-transferase fusion protein-Cdk2 at a high level. The cells were recovered and solubilized, then the active complex was adsorbed onto Glutathione Sepharose, and a cyclin A-Cdk2 complex was recovered using Precision Protease and was purified by HPLC column chromatography.

(2) Measurement of Cyclin A-Cdk2 Activity

For the measurement of the activity of cyclin A-Cdk2, a synthetic peptide (Ala-Lys-Ala-Lys-Lys-Thr-Pro-Lys-Lys-Ala-Lys-Lys) was used as the substrate.

The reaction was performed by partially modifying the method of Kitagawa et al. [Oncogene, Vol. 7, 1067-1074 (1992)]. The volume of the reaction solution was 21.1 µL, and to the R buffer, purified cyclin A-Cdk2, 0.01 mg/mL of the substrate peptide, 50 µM of non-labeled adenosine triphosphate (ATP), and 1 µCi of [γ-33P]-labeled ATP (2000 to 4000 Ci/mmole) were added to react at 30° C. for 30 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the cyclin A-Cdk2 activity was determined. The results are presented in Table 1 below.

Cdk1 Inhibitory Action (1) Purification of Cyclin B-Cdk1

The cDNA of Cdk1, and the cDNA of a fusion protein of cyclin B, an activating factor of Cdk1, and glutathione S-transferase, were integrated into a baculovirus expression vector to prepare a recombinant baculovirus. This was co-transfected into insect cell Sf9 to express an active complex of the cyclin B/glutathione S-transferase fusion protein-Cdk1 at a high level. The cells were recovered and solubilized, then the active complex was adsorbed onto Glutathione Sepharose, and a cyclin B-Cdk1 active complex was recovered using Precision Protease and was purified by HPLC column chromatography.

(2) Measurement of Cyclin B-Cdk1 Activity

For the measurement of the activity of cyclin B-Cdk1, a synthetic peptide (Ala-Lys-Ala-Lys-Lys-Thr-Pro-Lys-Lys-Ala-Lys-Lys) was used as the substrate.

The reaction was performed by partially modifying the method of Kitagawa et al. [Oncogene, Vol. 7, 1067-1074 (1992)]. The volume of the reaction solution was 21.1 µL, and to the R buffer, purified cyclin B-Cdk1, 100 µM of the substrate peptide, 50 µM of non-labeled adenosine triphosphate (ATP), and 1 µCi of [γ-33P]-labeled ATP (2000 to 4000 Ci/mmole) were added to react at 30° C. for 30 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the cyclin B-Cdk1 activity was determined. The results are presented in Table 1 below.

Cdk5 Inhibitory Action (1) Measurement of p35-Cdk5 Activity

For the measurement of the activity of p35-Cdk5, a human-derived recombinant p35-Cdk6 active complex, which was expressed in insect cell and purified, was purchased from PanVera Corp. A synthetic peptide (Ala-Lys-Ala-Lys-Lys-Thr-Pro-Lys-Lys-Ala-Lys-Lys) was used as the substrate.

The reaction was performed by partially modifying the method of Kitagawa et al. [Oncogene, Vol. 7, 1067-1074 (1992)]. The volume of the reaction solution was 21.1 µL, and to the R buffer, purified cyclin p35-Cdk5, 0.01 mg/mL of the substrate peptide, 50 µM of non-labeled adenosine triphosphate (ATP), and 1 µCi of [γ-33P]-labeled ATP (2000 to 4000 Cu/mmole) were added to react at 30° C. for 10 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the p35-Cdk5 activity was determined. The results are presented in Table 1 below.

Cdk7 Inhibitory Action (1) Purification of Cyclin H-Cdk7

The cDNA of Cdk7, and the cDNA of a fusion protein of cyclin H, an activating factor of Cdk7, and glutathione S-transferase, were integrated into a baculovirus expression vector to prepare a recombinant baculovirus. This was co-transfected into insect cell Sf9 to express an active complex of the cyclin H/glutathione S-transferase fusion protein-Cdk7 at a high level. The cells were recovered and solubilized, then the active complex was adsorbed onto Glutathione Sepharose, and a cyclin H-Cdk7 active complex was recovered using Precision Protease.

(2) Measurement of Cyclin H-Cdk7 Activity

For the measurement of the activity of cyclin H-Cdk7, a synthetic peptide (Tyr-Ser-Pro-Thr-Ser-Pro-Thr-Tyr-Ser-Pro-Thr-Ser-Pro-Thr-Tyr-Ser-Pro-Thr-Ser-Pro-Thr) was used as the substrate.

The reaction was performed by partially modifying the method of Kitagawa et al. [Oncogene, Vol. 7, 1067-1074 (1992)]. The volume of the reaction solution was 21.1 µL, and to the R buffer, purified cyclin H-Cdk7, 25 µM of the substrate peptide, 50 µM of non-labeled adenosine triphosphate (ATP), and 1 µCi of [γ-33P]-labeled ATP (2000 to 4000 Ci/mmole) were added to react at 30° C. for 45 minutes. Then, 10 µL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1.1 µL of the dilutions. A control was provided by adding 1.1 µL of DMSO to the reaction system.

A representative compound of the compounds according to the invention was selected, and the $IC_{50}$ value of this compound for the cyclin H-Cdk7 activity was determined. The results are presented in Table 1 below.

Cdk9 Inhibitory Action (1) Purification of Cyclin T1-Cdk9

The cDNA of Cdk9, and the cDNA of a fusion protein of cyclin T1, an activating factor of Cdk9, and glutathione S-transferase, were integrated into a baculovirus expression vector to prepare a recombinant baculovirus. This was co-transfected into insect cell Sf9 to express an active complex of the cyclin T1/glutathione S-transferase fusion protein-Cdk9 at a high level. The cells were recovered and solubilized, and the active complex was adsorbed onto Glutathione Sepharose, and then was purified by elution with 10 mM reductive glutathione. The solution containing the eluted active complex was dialyzed against B buffer (composition: 20 mM Tris-hydrochloric acid buffer (pH 7.4)/200 mM sodium chloride/0.1% Tween-20/10 mM 2-mercaptoethanol/1 mM dithiothreitol/10% glycerol) to remove the reductive glutathione.

(2) Measurement of Cyclin T1-Cdk9 Activity

For the measurement of the activity of cyclin T1-Cdk9, a synthetic peptide (Tyr-Ser-Pro-Thr-Ser-Pro-Thr-Tyr-Ser-Pro-Thr-Ser-Pro-Thr-Tyr-Ser-Pro-Thr-Ser-Pro-Thr-Tyr-Ser-Pro-Thr-Ser-Pro-Thr) was used as the substrate.

The reaction was performed by partially modifying the method of Kitagawa et al. [Oncogene, Vol. 7, 1067-1074 (1992)]. The volume of the reaction solution was 21.1 μL, and to the R buffer, purified cyclin T1-Cdk9, 25 μM of the substrate peptide, 50 μM of non-labeled adenosine triphosphate (ATP), and 0.5 μCi of [γ-33P]-labeled ATP (2000 to 4000 Ci/mmole) were added to react at 30° C. for 20 minutes. Then, 10 μL of 350 mM phosphate buffer was added to the reaction system to terminate the reaction. The substrate peptide was adsorbed onto P81 paper filter on a 96-well plate, and then washed several times with 75 mM phosphate buffer. The radioactivity of the substrate peptide was measured with a liquid scintillation counter.

Addition of the compound according to the invention to the reaction system was carried out by first preparing a dilution series of solutions of the compound in dimethylsulfoxide (DMSO), and adding 1 μL of the dilutions. A control was provided by adding 1.1 μL of DMSO to the reaction system.

A representative compound of the compounds according to the invention was selected, and the $IC_{50}$ value (nM) of this compound for the cyclin T1-Cdk9 activity was determined. The results are presented in Table 1 below.

TABLE 1

| Example No. | Cdk4 (nM) | Cdk6 (nM) | Cdc2 (nM) | Cdk2 (nM) | Cdk5 (nM) | Cdk7 (nM) | Cdk9 (nM) |
|---|---|---|---|---|---|---|---|
| 1 | 9.2 | 7.8 | 600 | 1700 | 3000 | 530 | 2500 |
| 13 | 6.0 | 13 | 620 | 850 | 2600 | 370 | 430 |
| 52 | 5.5 | — | — | — | — | 210 | 330 |
| 55 | 3.8 | 5.1 | 750 | 1900 | 3000 | 460 | 1400 |
| 93 | 4.2 | 7.3 | 870 | 480 | 2900 | 140 | 230 |
| 94 | 3.9 | 16 | 920 | 1700 | 3000 | 91 | 270 |
| 96 | 5.8 | 9.3 | 560 | 600 | 3000 | 160 | 140 |
| 99 | 6.0 | — | — | — | 2400 | 120 | 98 |
| 105 | 5.3 | — | — | — | 3000 | 370 | 180 |
| 106 | 8.4 | — | — | — | 3000 | 560 | 310 |
| 107 | 8.8 | — | — | — | 3000 | 830 | 250 |
| 109 | 5.7 | 18 | 430 | 1000 | 3000 | 280 | 640 |
| 110 | 10 | — | — | — | 3000 | 490 | 320 |
| 113 | 13 | — | — | — | 3000 | 560 | 880 |
| 114 | 13 | — | — | — | 3000 | 780 | 1600 |
| 118 | 20 | — | — | — | 3000 | 990 | 980 |
| 125 | 9.0 | 17 | 1200 | 1600 | 3000 | 370 | 650 |
| 137 | 7.2 | 21 | 1200 | 4500 | 3000 | 1200 | 1100 |

From the results of Table 1, it is clear that the compound according to the invention has an excellent selective inhibitory activity against cyclin D2-Cdk4 and cyclin D2-Cdk6 over other Cdks. The selectivity of the compounds of Example 1, Example 13 and Example 137 of Table 1 above for Cdk4 and Cdk6 was compared with the selectivity of Compound 18-4 described in page 138 of the International Publication No. WO 01/17995.

TABLE 2

| Example | K1/K4 | K2/K4 | K5/K4 | K7/K4 | K9/K4 |
|---|---|---|---|---|---|
| 1 | 65 | 185 | 326 | 58 | 272 |
| 13 | 103 | 142 | 433 | 62 | 72 |
| 137 | 167 | 625 | 417 | 167 | 153 |
| Compound 18-4 of WO 01/17995 | 5.9 | 6.0 | 3.1 | 5.9 | 2.1 |

TABLE 3

| Example | K1/K6 | K2/K6 | K5/K6 | K7/K6 | K9/K6 |
|---|---|---|---|---|---|
| 1 | 77 | 218 | 385 | 68 | 321 |
| 13 | 48 | 65 | 200 | 28 | 33 |
| 137 | 57 | 214 | 143 | 57 | 52 |
| Compound 18-4 of WO 01/17995 | 2.0 | 2.0 | 1.1 | 2.0 | 0.7 |

In Table 2 and Table 3 above, K1/K4, K2/K4, K5/K4, K7/K4, K9/K4, K1/K6, K2/K6, K5/K6, K7/K6, and K9/K6 represent the selectivity for Cdk4 against Cdk1, the selectivity for Cdk4 against Cdk2, the selectivity for Cdk4 against Cdk5, the selectivity for Cdk4 against Cdk7, the selectivity for Cdk4 against Cdk9, the selectivity for Cdk6 against Cdk1, the selectivity for Cdk6 against Cdk2, the selectivity for Cdk6 against Cdk5, the selectivity for Cdk6 against Cdk7, and the selectivity for Cdk6 against Cdk9, respectively, and the values are determined by dividing the respective $IC_{50}$ values of Cdk1, Cdk2, Cdk5, CDk7 and CDk9 by the $IC_{50}$ value of Cdk4 or CDk6.

From Table 1, Table 2 and Table 3, it is clearly shown that the compound according to the invention has a remarkably excellent selective inhibitory activity against cyclin D2-Cdk4 and cyclin D2-Cdk6 over other Cdks, as compared with the Compound 18-4 described in page 138 of International Publication No. WO 01/17995.

Inhibitory Action Against Cell Proliferation (1) Method of Cell Culture

Clinically isolated cancer cell lines EOL-1, KU812 and JURKAT were cultured in RPMI1640 medium containing 10% fetal calf serum at 37° C. in the presence of 5% $CO_2$ under an atmosphere of saturated steam.

(2) Measurement of Inhibitory Action Against Cell Proliferation

The inhibitory action against cell proliferation was measured by modifying the method of Skehan et al. [J. Natl. Cancer Inst., Vo. 82, 1107-1112 (1990)] according to the method of Ishiyama et al. [Talanta, Vol. 44, 1299 (1997)]. 100 μL each of cell culture medium containing $1 \times 10^3$ live cells of EOL-1, KU812 and JURKAT, respectively, was dispensed into each well of a 96-well cell culture dish, and the cells were cultured overnight. On the next day, a dilution series of solutions in DMSO was prepared from a DMSO solution of the compound of each Example. Then, the dilution series of solutions or DMSO only as a control for no drug addition were separately added to the medium for cell culture. Finally, 100 μL each of the culture medium containing either the dilution series of solutions of the compounds or DMSO only, was added to the cells which had been cultured in a 96-well dish, and then the cells were further cultured for 3 days.

After adding 20 μL each of WST-8 (Kishida Chemical Co., Ltd.) to each well and culturing the cells for another 2 hours, the optical densities at 450 nm were measured against a reference wavelength of 650 nm, and were compared with the control group. The results obtained by determining the concentrations for 50% inhibition of cell proliferation ($IC_{50}$ (nM)) of the compounds of Examples are presented in the following Table 4.

TABLE 4

| Example No. | EOL-1(nM) | KU812(nM) | Jurkat(nM) |
|---|---|---|---|
| 1 | 54 | 150 | 230 |
| 13 | — | — | 170 |
| 52 | — | — | 160 |
| 94 | — | — | 180 |
| 96 | — | — | 140 |
| 99 | — | — | 190 |
| 105 | — | — | — |
| 106 | — | — | 63 |
| 107 | — | — | 63 |
| 109 | — | — | 110 |
| 110 | — | — | 73 |
| 113 | — | — | 72 |
| 114 | — | — | 83 |
| 118 | — | — | 90 |
| 125 | 5.6 | 180 | 260 |
| 137 | — | — | 250 |

As is clear from Table 4, the compound according to the invention is acknowledged to have a strong inhibitory action against cell proliferation.

As discussed in the above, the compound according to the invention has a strong inhibitory activity against Cdk4 and/or Cdk6 and at the same time, has a high selectivity therefor over other Cdks, and also has a strong inhibitory action against cell proliferation. Therefore, it is believed that the compound strongly inhibits proliferation of cancer cells, and would be useful as a highly safe anticancer agent. That is, a pharmaceutical composition containing the novel aminothiazole derivative according to the invention or a pharmaceutically acceptable salt or ester thereof, or an anticancer agent containing the novel aminothiazole derivative according to the invention or a pharmaceutically acceptable salt or ester thereof is believed to be effective for the treatment of cancer patients. Also, the pharmaceutical composition or the anticancer agent may contain pharmaceutically acceptable carriers or diluents. Here, the term "pharmaceutically acceptable carriers or diluents" refers to excipients [e.g., fats, bees wax, semi-solid or liquid polyol, natural or hydrogenated oil, etc.]; water [e.g., distilled water, especially distilled water for injection, etc.], physiological saline, alcohol (e.g., ethanol), glycerol, polyol, aqueous glucose solution, mannitol, plant oil, or the like; additives [e.g. bulking agent, disintegrant, binder, lubricant, wetting agent, stabilizer, emulsifier, dispersant, preservative, sweetener, colorant, flavoring agent or aromatic substance, thickening agent, diluent, buffering substance, solvent or solubilizer, agent for attaining storage effect, salt for adjusting osmotic pressure, coating agent or antioxidant], and the like.

Furthermore, for tumor suitable for expecting a therapeutic effect of the compound according to the invention, for example, human solid tumors and the like may be mentioned. Examples of the human solid tumors include cerebral cancer, head and neck cancer, esophageal cancer, thyroid cancer, small cell cancer, non-small cell cancer, breast cancer, gastric cancer, gall bladder/bile duct cancer, hepatic cancer, pancreatic cancer, colon cancer, rectal cancer, ovarian cancer, chorioepithelioma, uterine cancer, cervical cancer, renal pelvic/ureteral cancer, urinary bladder cancer, prostate cancer, penile cancer, testicular cancer, embryonal cancer, Wilms' tumor, skin cancer, malignant melanoma, neuroblastoma, osteosarcoma, Ewing's sarcoma, soft tissue sarcoma and the like.

In addition, examples of the diseases causing abnormality in cell cycle or cell proliferation, for which a therapeutic effect of the compound according to the invention is expected, include, but are not limited to, arthritis, arteriosclerosis, pulmonary fibrosis, cerebral infarction and the like.

Next, the "pharmaceutically acceptable salt or ester thereof" described above will be described.

When the compound according to the invention is used as an anticancer agent or the like, the compound can be used in the form of a pharmaceutically acceptable salt thereof. Typical examples of the pharmaceutically acceptable salt include salts with alkali metals such as sodium, potassium and the like, inorganic acid salts such as hydrochloride, sulfate, nitrate, phosphate, carbonate, hydrogen carbonate, hyperchlorate and the like; for example, organic acid salts such as acetate, propionate, lactate, maleate, fumarate, tartrate, malate, citrate, ascorbate and the like; for example, sulfonates such as methanesulfonate, isethionate, benzenesulfonate, toluenesulfonate and the like; for example, acidic amino acid salts such as aspartate, glutamate and the like; and the like.

Preparation of the pharmaceutically acceptable salts of the compound according to the invention can be carried out by appropriately combining methods that are conventionally used in the field of organic synthetic chemistry. Specifically, a method of neutrally titrating a solution of the compound according to the invention in a free form using an alkaline solution or an acidic solution, or the like may be mentioned.

Examples of the ester of the compound according to the invention include methyl ester, ethyl ester and the like. These esters can be prepared by esterifying a free carboxyl group according to standard methods.

For the dosage form used in the case of using the compound according to the invention as an anticancer agent or the like, various forms can be selected, and for example, oral formulations such as tablet, capsule, powder, granule, liquid and the like; and sterilized liquid parenteral formulations such as solution, suspension and the like may be mentioned.

Here, solid preparations can be prepared, without modifications, in the form of tablet, capsule, granule or powder according to standard methods, but can be also prepared using appropriate additives. Examples of the additives include sugars such as lactose, sucrose and the like; starches of corn, wheat, rice and the like; fatty acids such as stearic acid and the like; inorganic salts such as sodium metasilicate, magnesium aluminate, anhydrous calcium phosphate, and the like; synthetic polymers such as polyvinylpyrrolidone, polyalkylene glycol and the like; fatty acid salts such as calcium stearate, magnesium stearate and the like; alcohols such as stearyl alcohol, benzyl alcohol and the like; synthetic cellulose derivatives such as methylcellulose, carboxymethylcellulose, ethylcellulose, hydroxypropylmethylcellulose and the like; and in addition to these, conventionally used additives such as water, gelatin, talc, plant oils, gum arabic, and the like.

These solid preparations such as tablet, capsule, granule, powder and the like may generally contain 0.1 to 100% by weight, preferably 5 to 100% by weight, more preferably 5 to 85% by weight, and particularly preferably 5 to 30% by weight, of the active ingredient.

Liquid preparations can be prepared in the form of suspension, syrup, injectable preparation or the like, using appropriate additives that are used for liquid preparations, such as water, alcohols, plant-derived oils such as soybean oil, peanut oil, sesame oil and the like.

In particular, examples of appropriate solvent or diluent useful in the case of administering parenterally via intramuscular injection, intravenous injection, or subcutaneous injection, include distilled water for injection, aqueous solution of lidocaine hydrochloride (for intramuscular injection), physiological saline, aqueous glucose solution, ethanol, fluid for intravenous injection (e.g., aqueous solution of citric acid, sodium citrate and the like), electrolyte solution (e.g., fluid for infusion, for intravenous injection), and the like, or mixed solutions thereof.

These injectable preparations may be in such a form that the active ingredient is preliminarily dissolved, or in such a form that the active ingredient as a powder or the active ingredient compounded with suitable additives is to be dissolved at the time of use. Such injectable liquid can usually contain 0.1 to 10% by weight, preferably 1 to 5% by weight, of the active ingredient.

The liquid for oral administration, such as suspension, syrup or the like, can contain 0.5 to 10% by weight, preferably 1 to 5% by weight, of the active ingredient.

The preferred amount of the compound according to the invention to be administered in practice can be appropriately increased or decreased in accordance with the kind of the compound to be used, the kind of the composition mixed, the frequency of application, the specific site to be treated, and the conditions of the patient. For example, the daily dose for an adult is, in the case of oral administration, 10 to 500 mg, preferably 10 to 200 mg, and in the case of parenteral administration, preferably in the case of intravenous injection, 10 to 100 mg, preferably 10 to 30 mg, per day. In addition, the dose frequency may vary depending on the mode of administration and symptoms, but the administration can be conducted once, or divided into 2 to 5 portions, and preferably 2 to 3 portions.

BEST MODE FOR CARRYING OUT THE INVENTION

Examples

Hereinafter, the present invention will be described in more detail with reference to Examples, but the invention is not intended to be limited by the Examples by any means. For example, in the case of describing a racemate in an Example, the invention of chiral isomers thereof are definitely included in the scope of the invention. In the Examples, thin layer chromatography was performed using Silica gel $_{60}F_{254}$ (Merck & Co., Inc.) for the plate, and a UV detector for the detection. Wakogel™ C-300 or C-200 (Wako Pure Chemical Industries, Ltd.) or NH (Fuji Silysia Chemical, Ltd.) was used as the silica gel for column. The MS spectra were measured using JMS-SX102A (JEOL, Inc.), QUATTRO II (Micromass, Ltd.), or ZMD (Micromass, Ltd.) in the case of LC-MS. For the NMR spectra, dimethylsulfoxide was used as the internal standard in the case of measuring in a deuterated dimethylsulfoxide solution, and a spectrometer such as Gemini-200 (200 MHz; Varian, Inc.), Gemini-300 (300 MHz; Varian, Inc.), Mercury 400 (400 MHz; Varian, Inc.), or Inova 400 (400 MHz; Varian, Inc.) was used for the measurement. All δ values were expressed in ppm.

The meanings of the abbreviations used in the NMR measurement are given below.
s: Singlet
d: Doublet
dd: Double doublet
ddd: Double double doublet
t: Triplet
dt: Double triplet
q: Quartet
dq: Double quartet
m: Multiplet
br: Broad
J: Coupling constant
Hz: Hertz
DMSO-$d_6$: Deuterated dimethylsulfoxide
CDCl$_3$: Deuterated chloroform
CD$_3$OD: Deuterated methanol The meanings of the abbreviations used in Examples are presented below.
TBS: t-Butyldimethylsilyl group
Ms: Methanesulfonyl group
Bz: Benzoyl group
Bn: Benzyl group
TBDPS: t-Butyldiphenylsilyl group
Ac: Acetyl group
Boc: t-Butoxycarbonyl group
SEM: 2-(trimethylsilyl)ethoxymethyl group
MOM: Methoxymethyl group
Me: Methyl group

Example 1

Synthesis of compound represented by following Formula [1]

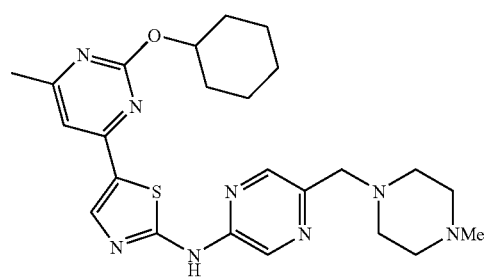

(1) 175 g of 5-methyl-2-pyrazinecarboxylic acid was suspended in 1 L of dioxane, then 1 L of t-butanol, 175 mL of triethylamine, and 287 mL of diphenyl azidophosphate were sequentially added to the suspension, and the reaction solution was heated to 100° C. The obtained reaction solution was stirred at the same temperature for 3 hours and then cooled to room temperature, and the solvent was distilled off under reduced pressure. The residue was poured onto a saturated aqueous solution of sodium hydrogen carbonate, and the aqueous phase was extracted with ethyl acetate. The obtained extraction liquid was washed with a saturated aqueous solution of ammonium chloride and dried, and then the solvent was distilled off under reduced pressure. The obtained crude product was crystallized from acetonitrile, to obtain 158 g of the following Compound [1-1].

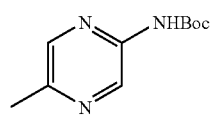

The spectral data of the compound represented by the above Formula [1-1] is presented below.
$^1$H-NMR (CDCl$_3$) δ: 9.15 (1H, s), 8.70 (1H, s), 7.41 (1H, brs), 2.51 (3H, s), 1.55 (9H, s).
mass: 210 (M+1)$^+$.

(2) 158 g of the Compound [1-1] obtained in (1) above was dissolved in 2 L of carbon tetrachloride, then 267 g of N-bromosuccinimide and 25 g of azobisisobutyronitrile were added to the solution, and the mixture was stirred overnight under overheating reflux. The obtained reaction solution was cooled to room temperature, and the insolubles were removed by filtration under reduced pressure. The filtrate was concentrated, and a monobromide product [1-2-1] was obtained as a mixture of a dibromide product [1-2-2] and Compound [1-1]. The monobromide product [1-2-1] was used in the subsequent reaction without further purification.

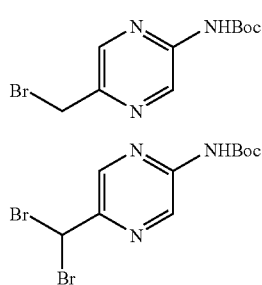

[1-2-1]

[1-2-2]

The spectral data of the compound represented by the above Formula [1-2-1] is presented below.
$^1$H-NMR (CDCl$_3$) δ: 9.27 (1H, s), 8.33 (1H, s), 7.91 (1H, brs), 4.55 (2H, s), 1.55 (9H, s).
mass: 288, 300 (M+1)$^+$.

(3) The monobromide product [1-2-1] obtained in (2) above was dissolved in 2 L of acetonitrile, then 145 g of potassium acetate and 10 g of 18-crown-6 were added to the solution at room temperature, and the mixture was stirred at the same temperature for 1 hour. The insolubles were removed by filtration under reduced pressure, and the filtrate was concentrated under reduced pressure. The residue was dissolved in chloroform, and the resulting solution was poured onto a saturated aqueous solution of sodium hydrogen carbonate, and was extracted with chloroform. The extract was dried, then the solvent was removed under reduced pressure, and an acetic acid ester product [1-3-1] was obtained as a mixture of a diacetate product [1-3-2] and Compound [1-1]. The acetic acid ester product was used in the subsequent reaction without further purification.

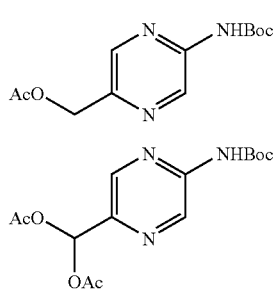

[1-3-1]

[1-3-2]

The spectral data of the compound represented by the above Formula [1-3-1] is presented below.
$^1$H-NMR (CDCl$_3$) δ: 9.29 (1H, s), 8.30 (1H, s), 7.90 (1H, brs), 5.19 (2H, s), 2.13 (3H, s), 1.55 (9H, s).
mass: 268 (M+1)$^+$.

(4) The acetic acid ester product [1-3-1] obtained in (3) above was dissolved in 1 L of THF and 0.3 L of methanol, then 252 mL of a 3 M aqueous solution of sodium hydroxide was added to the solution, and the mixture was stirred overnight at room temperature. The obtained reaction solution was concentrated under reduced pressure, and the concentrate was poured onto water. The aqueous phase was extracted with chloroform and dried, then the solvent was removed under reduced pressure, and a benzyl alcohol product [1-4] was obtained as a mixture with Compound [1-1]. The benzyl alcohol product was used in the subsequent reaction without further purification.

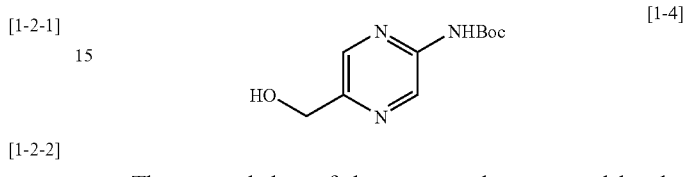

[1-4]

The spectral data of the compound represented by the above Formula [1-4] is presented below.
$^1$H-NMR (CDCl$_3$) δ: 9.25 (1H, s), 8.25 (1H, s), 7.73 (1H, brs), 4.77 (2H, s), 2.97 (1H, brs), 1.55 (9H, s).
mass: 226 (M+1)$^+$.

(5) The benzyl alcohol product [1-4] obtained in (4) above was dissolved in 1 L of DMF, then 44 g of imidazole and 147 mL of chloro-t-butyldiphenylsilane were added to the solution in an ice bath, and the mixture was stirred overnight at room temperature. The obtained reaction solution was poured onto ice water, and the aqueous phase was extracted with ethyl acetate. The extract was washed with water and saturated brine and dried, and the solvent was concentrated under reduced pressure. The residue was purified by silica gel column chromatography, and a silyl ether product [1-5] was obtained as a mixture with a side product derived from chloro-t-butyldiphenylsilane. The silyl ether product was used in the subsequent reaction without further purification.

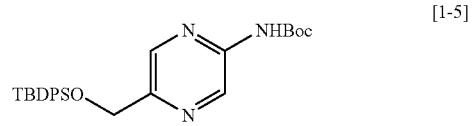

[1-5]

The spectral data of the compound represented by the above Formula [1-5] is presented below.
$^1$H-NMR (CDCl$_3$) δ: 9.15 (1H, s), 8.45 (1H, s), 7.74-7.65 (4H, m), 7.46-7.35 (6H, s), 4.85 (2H, s), 1.55 (9H, s), 1.11 (9H, s).

(6) The silyl ether product [1-5] obtained in (5) above was dissolved in 0.5 L of chloroform, and 0.25 L of trifluoroacetic acid was added to the solution in an ice bath. After stirring at room temperature for 2 hours, 0.1 L of trifluoroacetic acid was added thereto. After stirring at room temperature for another 3 hours, the solvent was removed under reduced pressure. Water was added to the residue, then sodium hydrogen carbonate was added to alkalinize the residue, and the aqueous phase was extracted with chloroform. After drying, the solvent was concentrated under reduced pressure, and an aminopyrazine product [1-6] was obtained as a mixture with a side product derived from chloro-t-butyldiphenylsilane. The aminopyrazine product was used in the subsequent reaction without further purification.

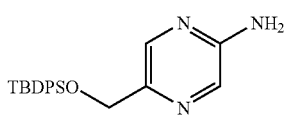
[1-6]

The spectral data of the compound represented by the above Formula [1-6] are presented below.

$^1$H-NMR (CDCl$_3$) δ: 8.20 (1H, s), 7.88 (1H, s), 7.73-7.65 (4H, m), 7.44-7.35 (6H, s), 4.76 (2H, s), 4.50 (2H, brs), 1.11 (9H, s).

mass: 364 (M+1)$^+$.

(7) The aminopyrazine product [1-6] obtained in (6) was dissolved in 0.5 L of THF, then 38.4 mL of benzoylisocyanate was added to the solution in an ice bath, and the mixture was stirred at room temperature for 2 hours. The solvent was removed from the obtained reaction solution under reduced pressure, and the residue was poured onto saturated brine. The aqueous phase was extracted with ethyl acetate and dried, then the solvent was concentrated under reduced pressure, and a protected product of thiourea [1-7] was obtained as a mixture with a side product derived from chloro-t-butyl-diphenylsilane. The protected product of thiourea was used in the subsequent reaction without further purification.

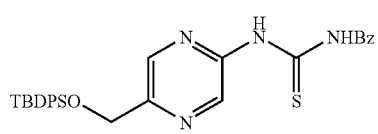
[1-7]

The spectral data of the compound represented by the above Formula [1-7] is presented below.

$^1$H-NMR (CDCl$_3$) δ: 13.09 (1H, s), 9.88 (1H, s), 9.14 (1H, s), 8.73 (1H, s), 7.93-7.92 (2H, m), 7.33-7.35 (13H, m), 4.93 (2H, s), 1.12 (9H, s).

(8) The protected product of thiourea [1-7] obtained in (7) was dissolved in 0.5 L of THF and 0.5 L of methanol, then 73 g of potassium carbonate and 200 mL of water were added to the solution, and the mixture was stirred at room temperature for 3 hours and continuously at 45° C. for 2 and a half hours. After cooling to room temperature, the reaction solution was removed of the solvent under reduced pressure, and water was added to the obtained residue. The solid thus produced was taken, sufficiently washed with water and hexane, and dried under reduced pressure to obtain 98 g of a thiourea product [1-8].

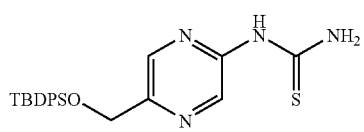
[1-8]

The spectral data of the compound represented by the above Formula [1-8] is presented below.

$^1$H-NMR (CDCl$_3$) δ: 10.48 (1H, brs), 9.02 (1H, brs), 8.43 (1H, s), 8.17 (1H, s), 7.68-7.66 (4H, m), 7.45-7.37 (6H, m), 4.85 (2H, s), 1.12 (9H, s).

mass: 423 (M+1)$^+$.

(9) 5.93 mL of 4-chloro-2-methylthiopyrimidine was dissolved in 50 mL of diethyl ether, and 100 mL of a 1 M diethyl ether solution of methyllithium was gradually added to the solution at −78° C. The reaction solution was stirred at 0° C. for 1 hour, and then a solution prepared by mixing 2.3 mL of water and 15 mL of tetrahydrofuran was added to the reaction mixture. The reaction mixture was stirred at the same temperature for 10 minutes, and then 50 mL of a tetrahydrofuran solution containing 13.7 g of 2,3-dichloro-5,6-dicyanohydroquinone was added to the reaction solution. The reaction solution was stirred at the same temperature for 1 hour, and then 100 mL of a 1 N aqueous solution of sodium hydroxide was added to the reaction solution. The obtained reaction solution was extracted with hexane, and the organic phase was washed with a 1 N aqueous solution of sodium hydroxide and saturated brine. The resultant solution was dried over magnesium sulfate and filtered, and the filtrate was concentrated. The obtained residue was purified by silica gel column chromatography to obtain 5.1 g of 4-chloro-6-methyl-2-methylthiopyrimidine product [1-9] as a pale yellow solid.

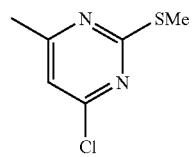
[1-9]

The spectral data of the compound represented by the above Formula [1-9] is presented below.

$^1$H-NMR (CDCl$_3$) δ: 6.86 (1H, d, J=0.4 Hz), 2.56 (3H, s), 2.44 (3H, d, J=0.4 Hz).

mass: 175 (M+1)$^+$.

(10) 15 g of a 40% hexane solution of ethyl ethynyl ether was dissolved in 50 mL of THF, and 29 mL of a 1 M tetrahydrofuran solution of a borane-tetrahydrofuran complex was added to the solution at 0° C. After stirring at room temperature for 4 hours, 150 mL of a tetrahydrofuran solution containing 4.0 g of the pyrimidine product [1-9], 35 mL of a 3 N aqueous solution of sodium hydroxide, 0.46 g of triphenylphosphine and 0.34 g of palladium (II) acetate were added to the mixture. The obtained reaction solution was stirred at the same temperature for 16 hours, and then 200 mL of water was added to the reaction solution. The reaction solution was extracted with ethyl acetate, and the organic phase was washed with saturated brine. The organic phase was dried over magnesium sulfate and filtered, and the filtrate was concentrate. The obtained residue was purified by silica gel column chromatography, and 4.9 g of a vinyl ether product [1-10] was obtained as a brown oily product.

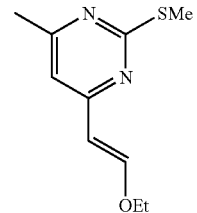
[1-10]

The spectral data of the compound represented by the above Formula [1-10] is presented below.

$^1$H-NMR (CDCl$_3$) δ: 7.83 (1H, d, J=12.4 Hz), 6.48 (1H, s), 5.64 (1H, d, J=12.4 Hz), 3.98 (H, q, J=7.6 Hz), 2.54 (3H, s), 2.36 (3H, s), 1.36 (3H, t, J=7.6 Hz).

mass: 211 (M+1)$^+$.

(11) 1.5 g of the vinyl ether product [1-10] obtained in (10) above was dissolved in 37 mL of ethanol, and 1.5 g of N-bromosuccinimide was added to the solution at 0° C. After stirring at the same temperature for 30 minutes, water was added to the mixture. The obtained reaction solution was extracted with ethyl acetate, and the organic phase was washed with saturated brine. This organic phase was dried over magnesium sulfate, and filtered, and the filtrate was concentrated. The obtained residue was purified by silica gel column chromatography to obtain 1.8 g of an acetal product [1-11] was obtained as a brown oily product.

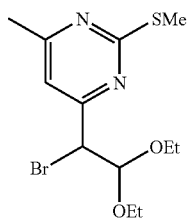

[1-11]

The spectral data of the compound represented by the above Formula [1-11] is presented below.

¹H-NMR (CDCl₃) δ: 6.92 (1H, s), 5.08 (1H, d, J=7.2 Hz), 4.77 (1H, d, J=7.2 Hz), 3.77 (1H, dq, J=9.6, 7.6 Hz), 3.68 (1H, dq, J=9.6, 7.6 Hz), 3.67 (1H, dq, J=9.6, 7.6 Hz), 3.52 (1H, dq, J=9.6, 7.6 Hz), 2.56 (3H, s), 2.46 (3H, s), 1.26 (3H, t, J=7.6 Hz), 1.07 (3H, t, J=7.6 Hz).

mass: 357 (M+23)⁺.

(12) 1.8 g of the acetal product [1-11] obtained in (11) above and 2.0 g of the thiourea product [1-8] were suspended in 20 mL of a mixed solvent of ethanol-water (9:1), and 1.0 g of p-toluenesulfonic acid monohydrate was added to the suspension at room temperature. After stirring at 90° C. for 12 hours, the reaction solution was concentrated. The obtained residue was dissolved in 20 mL of methanol, and then 80 mL of diethyl ether was added to the solution. A precipitate formed therein was filtered and dried to obtain 1.8 g of the target compound [1-12] as a mixture with p-toluenesulfonic acid. This mixture was used in the subsequent reaction without further purification.

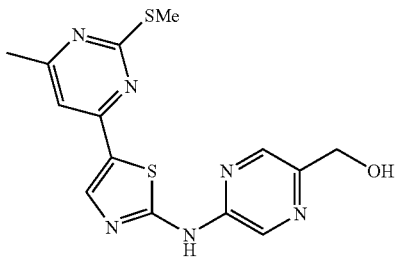

[1-12]

(13) 1.8 g of the aforementioned mixture [1-12] was dissolved in 10 mL of dimethylformamide, and 3.5 g of imidazole was added to the solution. 3.8 g of tert-butyldimethylsilyl chloride was added to the mixture in an ice bath, and the mixture was stirred at room temperature for 3 hours. After adding water, the reaction solution was extracted with ethyl acetate. The organic phase was washed with water and saturated brine and then dried over magnesium sulfate. The organic phase was filtered, and the filtrate was concentrated. The obtained residue was purified by silica gel column chromatography to obtain 0.53 g of a silyl ether product [1-13] as a brown solid.

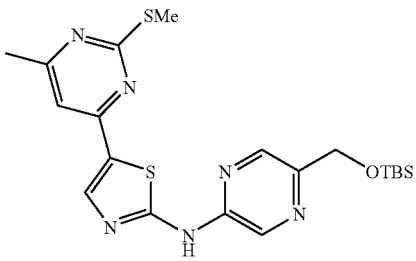

[1-13]

The spectral data of the compound represented by the above Formula [1-13] is presented below.

¹H-NMR (CDCl₃) δ: 8.51 (1H, s), 8.35 (1H, s), 8.12 (1H, s), 7.05 (1H, s), 4.85 (2H, s), 2.64 (3H, s), 2.48 (3H, s), 0.98 (9H, s), 0.17 (6H, s).

mass: 461 (M+1)⁺.

(14) 0.53 g of the silyl ether product [1-13] was dissolved in 11 mL of chloroform, then 0.58 mL of diisopropylethylamine and 0.39 μL of 2-trimethylsilylethoxymethyl chloride were added to the solution at 0° C., and the mixture was stirred at the same temperature for 1 hour. The obtained reaction solution was diluted with ethyl acetate, and then the organic phase was washed with a saturated aqueous solution of sodium hydrogen carbonate and saturated brine. This organic phase was dried over magnesium sulfate and filtered, and the filtrate was concentrated. The obtained residue was purified by silica gel column chromatography to obtain 0.33 g of a SEM product [1-14] and 0.15 g of a regioisomer thereof as an orange solid.

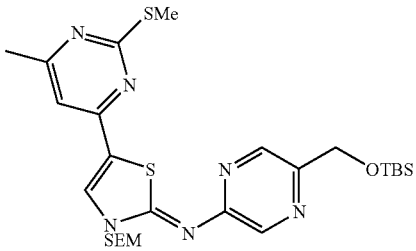

[1-14]

The spectral data of the compound represented by the above Formula [1-14] is presented below.

¹H-NMR (CDCl₃) δ: 8.56 (1H, d, J=1.2 Hz), 8.40 (1H, d, J=1.2 Hz), 7.88 (1H, s), 6.87 (1H, s), 5.61 (2H, s), 4.86 (2H, s), 3.76-3.71 (2H, m), 2.62 (3H, s), 2.47 (3H, s), 1.03-0.97 (2H, m), 0.98 (9H, s), 0.15 (6H, s), −0.02 (9H, s).

mass: 591 (M+1)⁺.

(15) 2.24 g of the SEM product [1-14] obtained in (14) above was dissolved in 40 mL of chloroform, and 1.10 g of m-chloroperbenzoic acid was added to the solution at 0° C. After stirring at the same temperature for 1.5 hours, the obtained reaction solution was diluted with ethyl acetate. The reaction liquid was washed with a saturated aqueous solution of sodium hydrogen carbonate and an aqueous solution of sodium thiosulfate. The reaction solution was further washed with saturated brine and then dried over magnesium sulfate. The resultant solution was filtered, and the filtrate was concentrated. The obtained residue was purified by silica gel column chromatography to obtain 2.30 g of a sulfoxide product [1-15] as a brown oily product.

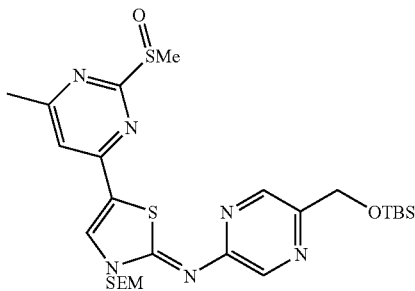

[1-15]

The spectral data of the compound represented by the above Formula [1-15] is presented below.

$^1$H-NMR (CDCl$_3$) δ: 8.60 (1H, d, J=1.6 Hz), 8.45 (1H, d, J=1.6 Hz), 8.10 (1H, s), 7.22 (1H, s), 5.62 (2H, s), 4.88 (2H, s), 3.80-3.71 (2H, m), 3.00 (3H, s), 2.67 (3H, s), 1.08-1.01 (2H, m), 1.00 (9H, s), 0.18 (6H, s), 0.02 (9H, s).

mass: 607 (M+1)$^+$.

(16) 63 mg of a 60% solution of sodium hydride was added to 0.5 mL of a 117 μL tetrahydrofuran solution of cyclohexanol at 0° C., and the mixture was stirred at the same temperature for 10 minutes. To this reaction solution, 2.0 mL of a tetrahydrofuran solution containing 135 mg of the sulfoxide product [1-15] obtained in (15) above was added at 0° C. After stirring at the same temperature for 30 minutes, the obtained reaction solution was diluted with ethyl acetate. The organic phase was washed with a saturated aqueous solution of ammonium chloride, water and saturated brine. The organic phase was dried over magnesium sulfate and filtered, and the filtrate was concentrated. The obtained residue was purified by silica gel column chromatography to obtain 59 mg of an ether product [1-16] as a yellow oily product.

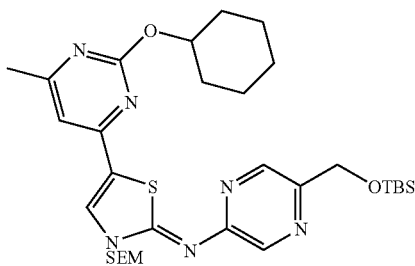

[1-16]

The spectral data of the compound represented by the above Formula [1-16] is presented below.

$^1$H-NMR (CDCl$_3$) δ: 8.55 (1H, d, J=1.6 Hz), 8.40 (1H, d, J=1.6 Hz), 7.85 (1H, s), 6.84 (1H, s), 5.60 (2H, s), 5.12-5.02 (1H, m), 4.86 (2H, s), 3.75-3.70 (2H, m), 2.46 (3H, s), 2.15-2.06 (2H, m), 1.90-1.80 (2H, m), 1.70-1.10 (6H, m), 1.03-0.95 (2H, m), 0.98 (9H, s), 0.15 (6H, s), −0.02 (9H, s).

mass: 643 (M+1)$^+$.

(17) 59 mg of the ether product [1-16] was dissolved in 0.92 mL of tetrahydrofuran, and 140 μL of a 1 M tetrahydrofuran solution of tetrabutylammonium fluoride was added to the solution at 0° C. The obtained reaction solution was stirred at the same temperature for 1 hour, then 10 mL of a saturated aqueous solution of ammonium chloride was added to the reaction solution, and the reaction mixture was extracted with ethyl acetate and dried. The extract was concentrated, and the obtained residue was purified by silica gel column chromatography to obtain 49 mg of a compound represented by [1-17] as a yellow oily product.

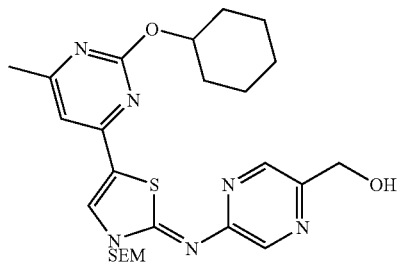

[1-17]

The spectral data of the compound represented by the above Formula [1-17] is presented below.

$^1$H-NMR (CDCl$_3$) δ: 8.44 (1H, d, J=1.2 Hz), 8.42 (1H, brs), 7.85 (1H, s), 6.83 (1H, s), 5.60 (2H, s), 5.15-5.05 (1H, m), 4.79 (2H, s), 3.73 (2H, t, J=8.0 Hz), 2.46 (3H, s), 2.15-2.05 (2H, m), 1.90-1.80 (2H, m), 1.70-1.55 (2H, m), 1.50-1.20 (4H, m), 1.01 (2H, t, J=8.0 Hz), −0.02 (9H, s).

mass: 529 (M+1)$^+$.

(18) 16 mg of the alcohol product [1-17] was dissolved in 0.5 mL of chloroform, and 27 μL of diisopropylethylamine and 7.3 μL of methanesulfonyl chloride were added to the solution at 0° C. After stirring at the same temperature for 1 hour, 20 μL of N-methylpiperazine and 22 mg of potassium carbonate were added to the mixture. After stirring at 70° C. for 1 hour, the obtained reaction solution was concentrated, and the obtained residue was purified by silica gel column chromatography to obtain 8.6 mg of an amine product [1-18] as a yellow oily product.

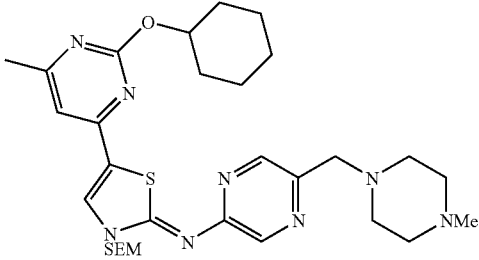

[1-18]

The spectral data of the compound represented by [1-18] is presented below.

$^1$H-NMR (CDCl$_3$) δ: 8.46 (1H, d, J=1.6 Hz), 8.40 (1H, d, J=1.6 Hz), 7.86 (1H, s), 6.83 (1H, s), 5.60 (2H, s), 5.15-5.05 (1H, m), 3.72 (2H, t, J=8.0 Hz), 3.68 (2H, s), 2.70-2.40 (8H, m), 2.46 (3H, s), 2.31 (3H, s), 2.15-2.05 (2H, m), 1.90-1.80 (2H, m), 1.80-1.20 (6H, m), 1.00 (2H, t, J=8.0 Hz), −0.02 (9H, s).

mass: 611 (M+1)$^+$.

(19) 8.6 mg of the above amine [1-18] was dissolved in 1 mL of a mixed solvent of trifluoroacetic acid-water (9:1), and the solution was stirred at room temperature for 2 hours. The reaction solution was concentrated, and the obtained residue was solidified from methanol and ether, and 7.5 mg of a trifluoroacetate of the target compound [1] was obtained as a yellow solid product.

The spectral data of the trifluoroacetate of the above Formula [1] is presented below.

$^1$H-NMR (DMSO-$d_6$) δ: 12.1 (1H, brs), 8.48 (1H, s), 8.43 (1H, s), 8.36 (1H, s), 7.42 (1H, s), 5.01-4.93 (1H, m), 3.81 (2H, s), 3.50-3.30 (4H, m), 3.20-2.90 (4H, m), 2.77 (3H, s), 2.38 (3H, s), 2.01-1.92 (2H, m), 1.80-1.70 (2H, m), 1.60-1.20 (6H, m).

mass: 481 (M+1)$^+$.

424 mg of the trifluoroacetate was suspended in 25 mL of chloroform. 25 mL of a saturated aqueous solution of sodium hydrogen carbonate was added to the suspension, and the mixture was stirred at room temperature for 30 minutes. The organic phase was concentrated, and the obtained residue was dissolved in 4 mL of methanol. 2 mL of a 4 N hydrogen chloride-dioxane solution was added to the solution of residue at 0° C. After stirring at the same temperature for 5 minutes, the reaction solution was concentrated. The obtained residue was dissolved in methanol, and a precipitate generated upon addition of diethyl ether to the methanol solution was filtered to obtain 351 mg of a hydrochloride salt of the target compound [1] as a yellow solid.

The spectral data of the hydrochloride salt of the above Formula [1] is presented below.

$^1$H-NMR (DMSO-$d_6$) δ: 8.63 (1H, s), 8.57 (1H, s), 8.41 (1H, s), 7.47 (1H, s), 5.02-4.93 (1H, m), 4.47 (2H, brs), 3.64 (4H, brs), 3.40 (4H, brs), 2.81 (3H, s), 2.39 (3H, s), 2.05-1.95 (2H, m), 1.81-1.70 (2H, m), 1.61-1.22 (6H, m).

mass: 481 (M+1)$^+$.

The hydrochloride salt of the target compound [1] can be also obtained by treating the Compound [1-18] with a 4 N dioxane solution of hydrogen chloride, in methanol at room temperature, and performing the post-treatment as described above.

Example 2

Synthesis of compound represented by following Formula [2]

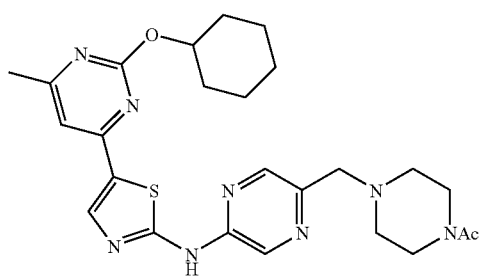

[2]

4.1 mg of a trifluoroacetate salt of the target compound [2] was obtained as a yellow solid, from 16 mg of the benzyl alcohol product [1-17] obtained in Example 1-(17) and 40 mg of N-acetylpiperazine, according to the methods of Example 1-(18) and (19).

The spectral data of the compound represented by the above Formula [2] is presented below.

$^1$H-NMR (DMSO-$d_6$) δ: 8.53 (1H, s), 8.48 (1H, s), 8.37 (1H, s), 7.43 (1H, s), 5.01-4.91 (1H, m), 3.60-3.20 (10H, m), 2.38 (3H, s), 2.02-1.95 (2H, m), 2.01 (3H, s), 1.80-1.70 (2H, m), 1.61-1.21 (6H, m).

mass: 509 (M+1)$^+$.

Example 3

Synthesis of compound represented by following Formula [3]

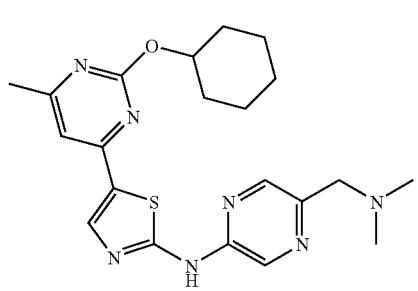

[3]

6.6 mg of a trifluoroacetate salt of the target compound [3] was obtained as a pale yellow solid, from 16 mg of the benzyl alcohol product [1-17] obtained in Example 1-(17) and 80 μL of a 2 M tetrahydrofuran solution of dimethylamine, according to the methods of Example 1-(18) and (19).

The spectral data of the compound represented by the above Formula [3] is presented below.

$^1$H-NMR (DMSO-$d_6$) δ: 12.29 (1H, brs), 9.90 (1H, brs), 8.55 (1H, brd, J=1.6 Hz), 8.51 (1H, brd, J=1.6 Hz), 8.38 (1H, s), 7.44 (1H, s), 5.00-4.92 (1H, m), 4.39 (2H, brs), 2.79 (6H, s), 2.38 (3H, s), 2.04-1.96 (2H, m), 1.81-1.71 (2H, m), 1.62-1.24 (6H, m).

mass: 426 (M+1)$^+$.

Example 4

Synthesis of compound represented by following Formula [4]

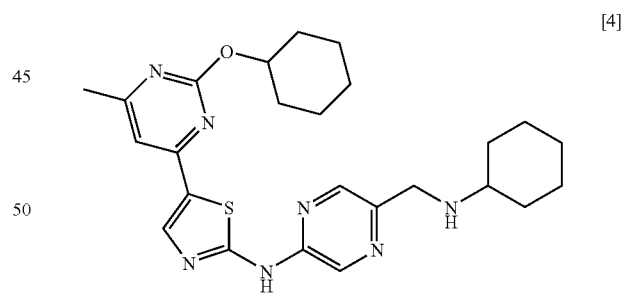

[4]

0.78 mg of a trifluoroacetate salt of the target compound [4] was obtained as a yellow solid, from 13 mg of the benzyl alcohol product [1-17] obtained in Example 1-(17) and 15 μL of cyclohexylamine, according to the methods of Example 1-(18) and (19).

The spectral data of the compound represented by the above Formula [4] is presented below.

$^1$H-NMR (DMSO-$d_6$) δ: 8.92 (1H, brs), 8.57-8.53 (2H, m), 8.38 (1H, s), 7.44 (1H, s), 5.00-4.92 (1H, m), 4.35-4.29 (2H, m), 3.12-2.99 (1H, m), 2.38 (3H, s), 2.12-1.94 (4H, m), 1.82-1.70 (4H, m), 1.65-1.04 (12H, m).

mass: 480 (M+1)$^+$.

Example 5

Synthesis of compound represented by following Formula [5]

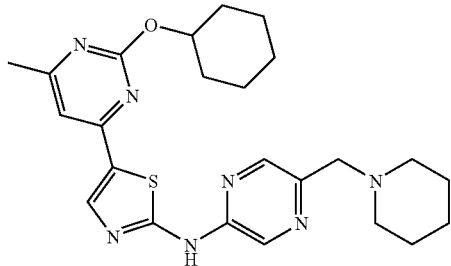

[5]

0.54 mg of a trifluoroacetate salt of the target compound [5] was obtained as a yellow solid, from 13 mg of the benzyl alcohol product [1-17] obtained in Example 1-(17) and 13 μL of piperidine, according to the methods of Example 1-(18) and (19).

The spectral data of the compound represented by the above Formula [5] is presented below.

$^1$H-NMR (DMSO-$d_6$) δ: 9.64 (1H, brs), 8.55 (1H, brs), 8.52 (1H, brs), 8.38 (1H, brs), 7.44 (1H, s), 5.00-4.91 (1H, m), 4.41-4.37 (2H, m), 3.20-2.80 (4H, m), 2.38 (3H, s), 2.04-1.95 (2H, m), 1.84-1.20 (14H, m).

mass: 466 (M+1)$^+$.

Example 6

Synthesis of compound represented by following Formula [6]

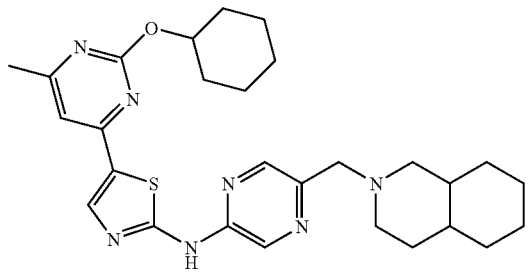

[6]

4.6 mg of a trifluoroacetate salt of the target compound [6] was obtained as a yellow solid, from 15 mg of the benzyl alcohol product [1-17] obtained in Example 1-(17) and 23 μL of decahydroisoquinoline, according to the methods of Example 1-(18) and (19).

The spectral data of the compound represented by the above Formula [6] is presented below.

$^1$H-NMR (DMSO-$d_6$) δ: 12.29 (1H, brs), 8.55 (1H, brs), 8.52-8.49 (1H, m), 8.38 (1H, s), 7.44 (1H, s), 5.00-4.91 (1H, m), 4.45-4.35 (2H, m), 3.14-2.90 (4H, m), 2.38 (3H, s), 2.14-0.80 (22H, m).

mass: 520 (M+1)$^+$.

Example 7

Synthesis of compound represented by following Formula [7]

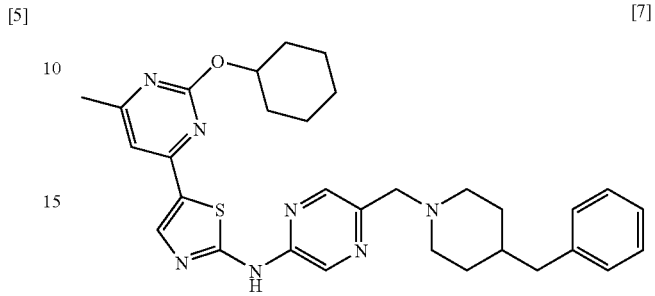

[7]

9.3 mg of a trifluoroacetate salt of the target compound [7] was obtained as a yellow solid, from 15 mg of the benzyl alcohol product [1-17] obtained in Example 1-(17) and 27 μL of 4-benzylpiperidine, according to the methods of Example 1-(18) and (19).

The spectral data of the compound represented by the above Formula [7] is presented below.

$^1$H-NMR (DMSO-$d_6$) δ: 12.28 (1H, brs), 9.55 (1H, brs), 8.53 (1H, brs), 8.49 (1H, brs), 8.38 (1H, s), 7.44 (1H, s), 7.28 (2H, brt, J=7.2 Hz), 7.23-7.13 (3H, m), 5.00-4.90 (1H, m), 4.37 (2H, brs), 3.47-3.36 (2H, m), 3.02-2.88 (4H, m), 2.38 (3H, s), 2.04-1.94 (2H, m), 1.82-1.64 (5H, m), 1.62-1.20 (8H, m).

mass: 556 (M+1)$^+$.

Examples 8-22

Synthesis of compounds represented by following General Formula [8-1] (wherein $R_a$ and $R_b$, which may be identical or different, are each a hydrogen atom, a lower alkyl group, or a $C_3$-$C_8$ cycloalkyl group, or $R_a$ and $R_b$ may together form an aliphatic heterocyclic group, and the lower alkyl group, cycloalkyl group and aliphatic heterocyclic group may be substituted):

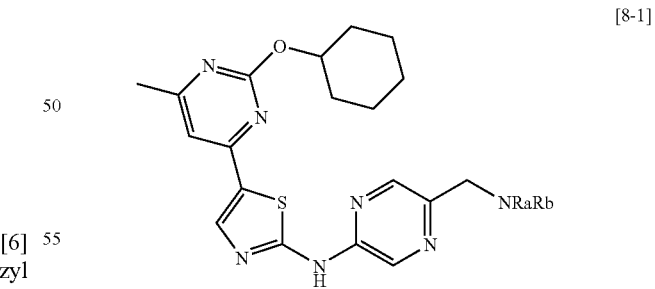

[8-1]

(1) 5 mg of the benzyl alcohol product obtained in Example 1-(17) was dissolved in 1 mL of chloroform, then 10 μL of N,N-diisopropylethylamine and 3 μL of methanesulfonyl chloride were added to the solution in an ice bath, and the mixture was stirred at the same temperature for 1 hour. 1 mL of a saturated aqueous solution of sodium hydrogen carbonate was added to the obtained reaction solution, and cyclopropylamine (in the case of Example 8), isopropylamine (in the case of Example 9), N-2-hydroxyethyl-N-methylamine (in the case of Example 10), pyrrolidine (in the case of Example 11), ethylamine (in the case of Example 12), 3-dimethylaminopyrrolidine (in the case of Example 13), 3-hydroxypyrrolidine (in the case of Example 14), N-(cyclohexyl)-N-methylamine (in the case of Example 15), 4-hydroxypiperidine (in the case of Example 16), cyclopentylamine (in the case of Example 17), dimethylamine (in the case of Example 18), 4-hydroxy-3-methylpiperidine (in the case of Example 19), (2R,3R)-3-hydroxy-2-methylpyrrolidine (in the case of Example 20), 2-hydroxyethylamine (in the case of Example 21), or 2-dimethylaminoethylamine (in the case of Example 22) was added to the reaction solution, each in an excess amount (50 μL). The mixture was stirred at 80° C. for 3 hours. The chloroform phase was purified with a fractional thin layer silica gel to obtain a purified benzylamine product.

(2) A solution of trifluoroacetic acid-water (10:1) was added to the benzylamine product. The mixture was stirred at room temperature for 3 hours and concentrated under reduced pressure, and then the target compounds [8] to [22] (respectively corresponding to Examples 8 to 22 described below) were obtained as trifluoroacetate salts. The target compounds were confirmed by LC-MS.

In addition, the method for synthesis of 4-hydroxy-3-methylpiperidine used in Example 19 is described in Heterocycles, 43, 205 (1996), and the method for synthesis of 3-hydroxy-2-methylpyrrolidine used in Example 20 is described in Eur. J. Med. Chem. Chim. Ther., 34, 125 (1999).

TABLE 5

| Examples 8 to 12 | Structure | Molecular formula | Mass (M + 1)+ |
|---|---|---|---|
| 8 | 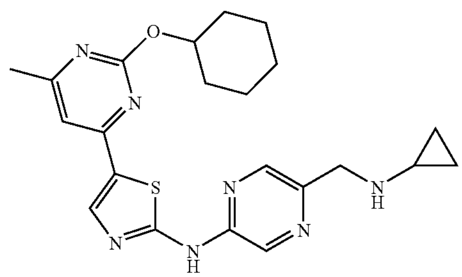 | C22H27N7OS | 438 |
| 9 | 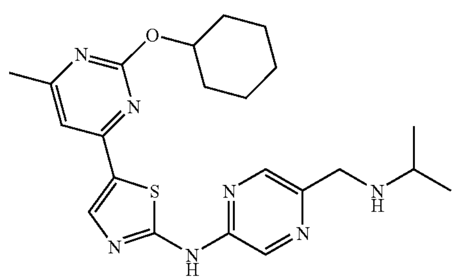 | C22H29N7OS | 440 |
| 10 | 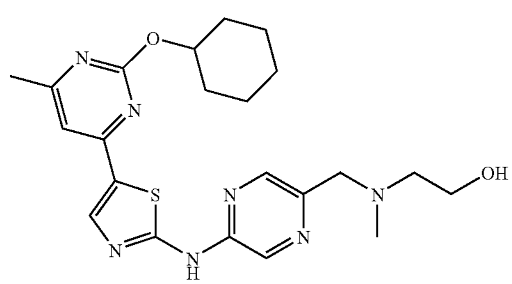 | C22H29N7O2S | 456 |
| 11 | 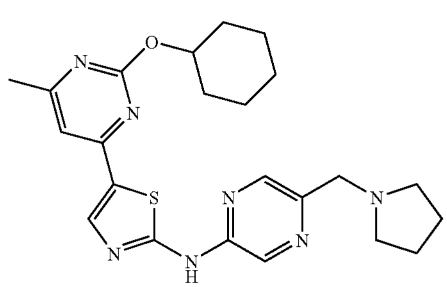 | C23H29N7OS | 452 |

TABLE 5-continued

| Examples 8 to 12 | Structure | Molecular formula | Mass (M + 1)+ |
|---|---|---|---|
| 12 | 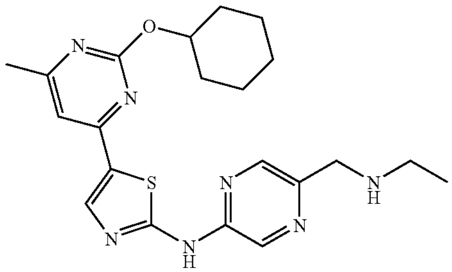 | C21H27N7OS | 426 |

TABLE 6

| Examples 13 to 17 | Structure | Molecular formula | Mass (M + 1)+ |
|---|---|---|---|
| 13 | 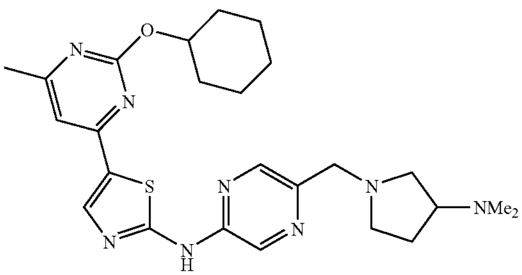 | C25H34N8OS | 495 |
| 14 | 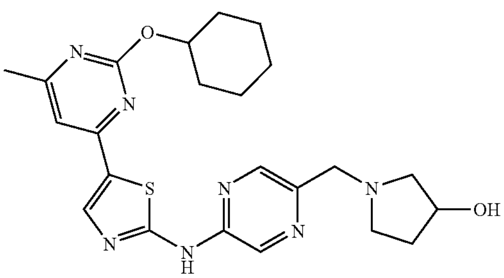 | C23H29N7O2S | 468 |
| 15 | 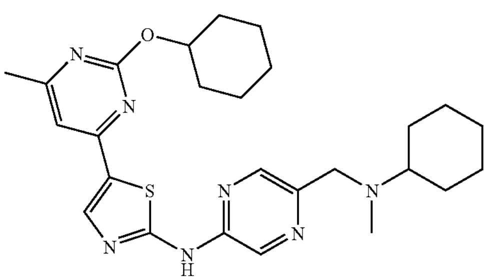 | C26H35N7OS | 494 |
| 16 | 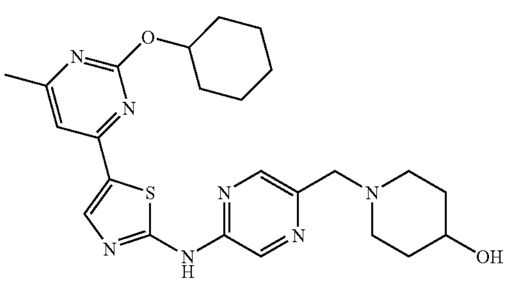 | C24H31N7O2S | 482 |

TABLE 6-continued
| Examples 13 to 17 | Structure | Molecular formula | Mass (M + 1)+ |
|---|---|---|---|
| 17 | 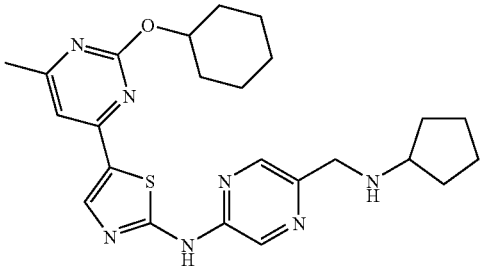 | C24H31N7OS | 466 |
TABLE 7
| Examples 18 to 22 | Structure | Molecular formula | Mass (M + 1)+ |
|---|---|---|---|
| 18 | 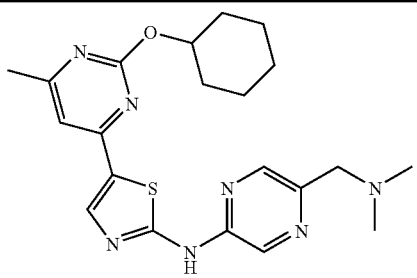 | C21H27N7OS | 426 |
| 19 | 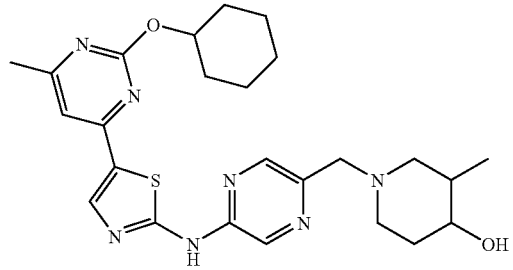 | C25H33N7O2S | 496 |
| 20 | 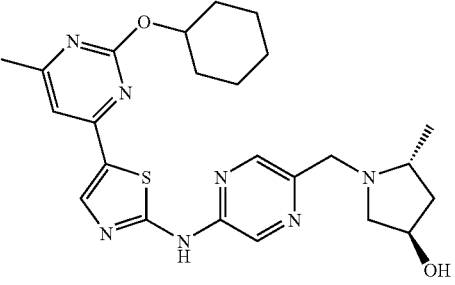 | C24H31N7O2S | 482 |
| 21 | 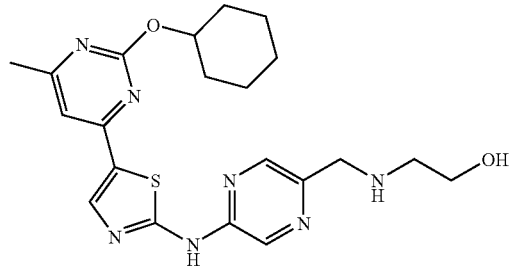 | C21H27N7O2S | 442 |

TABLE 7-continued

| Examples 18 to 22 | Structure | Molecular formula | Mass (M + 1)+ |
|---|---|---|---|
| 22 | 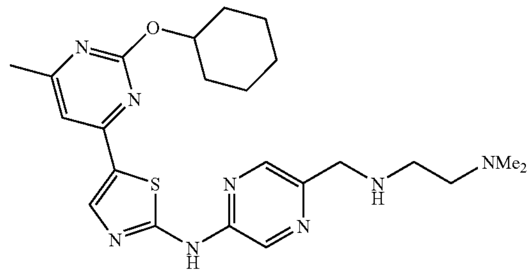 | C23H32N8OS | 469 |

Examples 23

Synthesis of compound represented by following Formula [23]

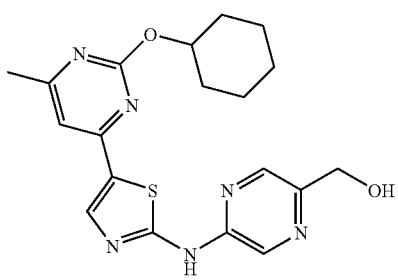

[23]

The benzyl alcohol product [1-17] obtained in Example 1-(17) was dissolved in a mixed solution of trifluoroacetic acid-water (10:1), and the solution was stirred at room temperature for 3 hours and concentrated under reduced pressure to obtain the target compound [23]. The target compound was confirmed by LC-MS.

mass: 399 (M+1)+.

Example 24

Synthesis of compound represented by following Formula [24]

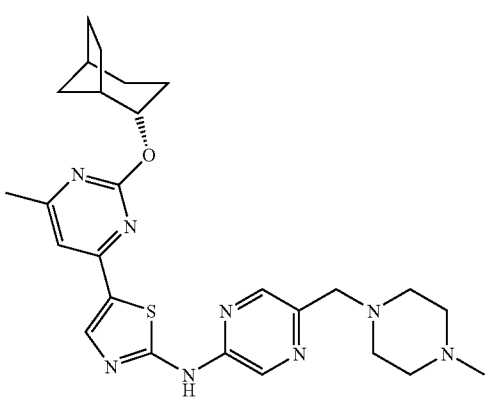

[24]

The target compound [24] was obtained from the sulfoxide product [1-15] obtained in Example 1-(15) and a sodium salt of cis-bicyclo[3.2.1]-2-octanol, according to the methods of Example 1-(16), (17), (18) and (19). The target compound was confirmed by LC-MS.

mass: 507 (M+1)+.

In addition, the method for synthesis of bicyclo[3.2.1]-2-octanol is described in J. Am. Chem. Soc., 81, 4709 (1959).

Example 25

Synthesis of compound represented by following Formula [25]

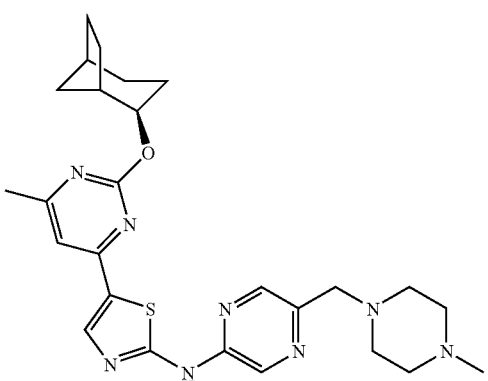

[25]

The target compound [25] was obtained from the sulfoxide product obtained in Example 1-(15) and a sodium salt of trans-bicyclo[3.2.1]-2-octanol, according to the methods of Example 1-(16), (17), (18) and (19). The target compound was confirmed by LC-MS.

mass: 507 (M+1)+.

In addition, the method for synthesis of the bicyclo[3.2.1]-2-octanol is described in J. Am. Chem. Soc., 81, 4709 (1959).

Example 26

Synthesis of compound represented by following Formula [26]

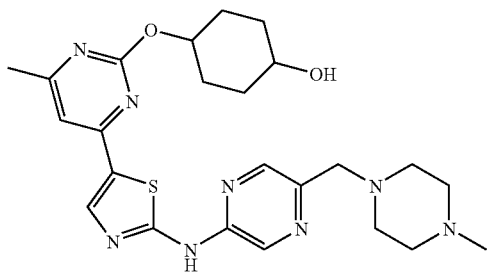

[26]

1.7 mg of a trifluoroacetate salt of the target compound [26] was obtained as a yellow solid from 70 mg of the sulfoxide product obtained in Example 1-(15) and a sodium salt of 4-cyclohexanediol, according to the methods of Example 1-(16), (17), (18) and (19).

The spectral data of the compound represented by the above Formula [26] is presented below.

$^1$H-NMR (DMSO-d$_6$) δ: 8.47 (1H, brs), 8.42 (0.5H, brs), 8.40 (0.5H, brs), 8.35 (0.5H, s), 8.35 (0.5H, s), 7.43-7.41 (1H, m), 5.06-5.00 (0.5H, m), 4.96-4.87 (0.5H, m), 3.69 (2H, brs), 3.50-3.20 (5H, m), 3.10-2.90 (4H, m), 2.77 (3H, brs), 2.39 (3H, s), 2.10-2.02 (2H, m), 1.94-1.82 (2H, m), 1.64-1.20 (4H, m).

mass: 497 (M+1)$^+$.

Example 27

Synthesis of compound represented by following Formula [27]

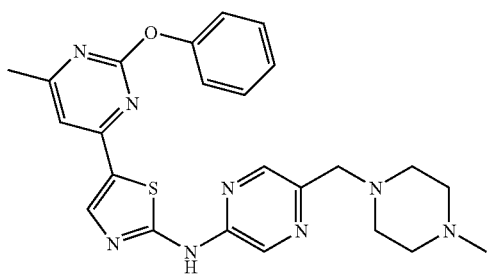

[27]

(1) The sulfoxide product obtained in Example 1-(15) and phenol were dissolved in dimethylformamide, and the solution was heated to 90° C. in the presence of potassium carbonate and stirred for 3 hours. The obtained reaction solution was poured onto saturated brine and was extracted with ethyl acetate. The extract was washed with water and saturated brine, dried and then concentrated. The obtained residue was purified by silica gel column chromatography, and a benzyl alcohol product [27-1] was obtained according to the method of Example 1-(17).

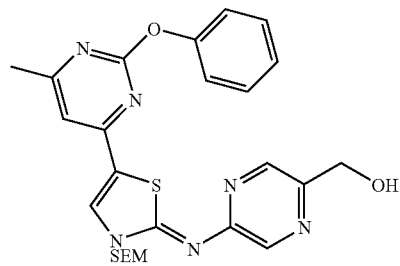

[27-1]

The compound was confirmed by LC-MS.
mass: 523 (M+1)$^+$.

(2) The target compound [27] was obtained from the benzyl alcohol product [27-1] and N-methylpiperazine, according to the methods of Example 8-22-(1) and (2). The target compound was confirmed by LC-MS.
mass: 475 (M+1)$^+$.

Examples 28-41

Synthesis of compounds represented by following General Formula [28-1] (wherein R$_a$ and R$_b$, which may be identical or different, are each a hydrogen atom, a lower alkyl group, a C$_3$-C$_8$ cycloalkyl group, or an aliphatic heterocyclic group, or R$_a$ and R$_b$ may together form an aliphatic heterocyclic ring, and the lower alkyl group, aliphatic heterocyclic group and cycloalkyl group may be substituted):

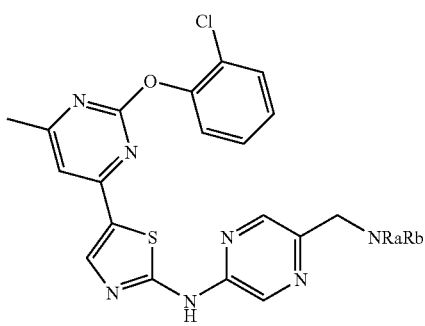

[28-1]

(1) Compound [28-2] was obtained from the sulfoxide product obtained in Example 1-(15) and 2-chlorophenol, according to the method of Example 27-(1).

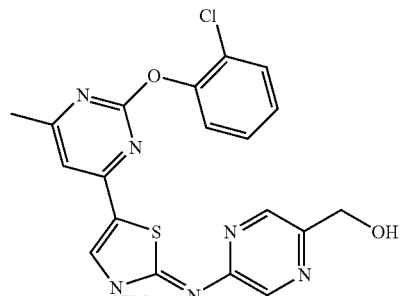

[28-2]

The compound was confirmed by LC-MS.
mass: 556 (M+1)$^+$.

(2) The target compounds [28] to [41] were respectively obtained from the benzyl alcohol product [28-2] and N-methylpiperazine (in the case of Example 28), (2S)-2-hydroxymethylpyrrolidine (in the case of Example 29), 4-hydroxypiperidine (in the case of Example 30), (3S)-3-hydroxypyrrolidine (in the case of Example 31), ethylamine (in the case of Example 32), (3S)-3-dimethylaminopyrrolidine (in the case of Example 33), methylamine (in the case of Example 34), pyrrolidine (in the case of Example 35), (3R)-3-hydroxypyrrolidine (in the case of Example 36), (3R)-3-dimethylaminopyrrolidine (in the case of Example 37), N-2-hydroxyethyl-N-methylamine (in the case of Example 38), dimethylamine (in the case of Example 39), isopropylamine (in the case of Example 40), and 2-hydroxyethylamine (in the case of Example 41), respectively, according to the methods of Example 8-22-(1) and (2). The target compounds were confirmed by LC-MS.

TABLE 8

| Examples 28 to 31 | Structure | Molecular formula | Mass (M + 1)+ |
|---|---|---|---|
| 28 | 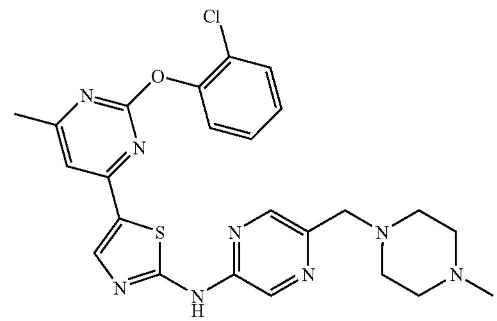 | C24H25ClN8OS | 509, 511 |
| 29 | 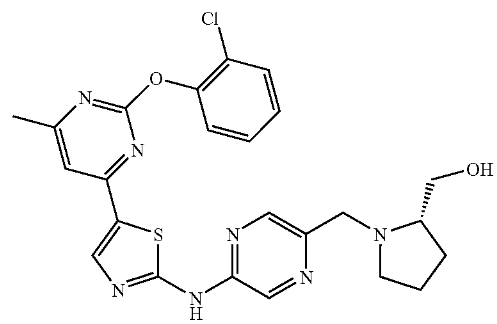 | C24H24ClN7O2S | 510, 512 |
| 30 | 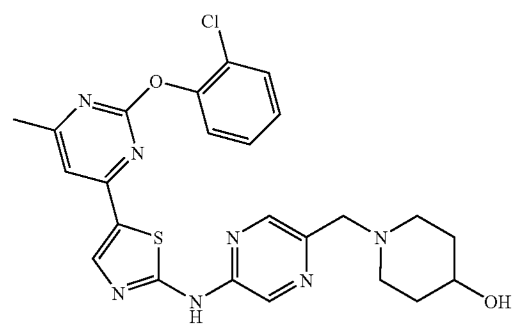 | C24H24ClN7O2S | 510, 512 |
| 31 | 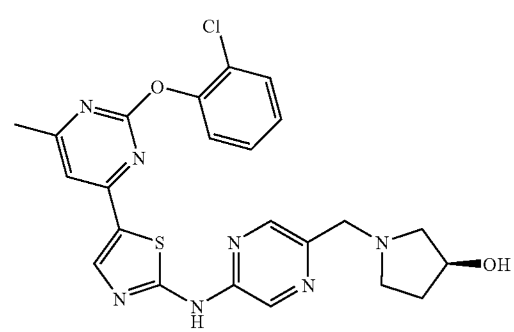 | C23H22ClN7O2S | 496, 498 |

TABLE 9

| Examples 32 to 36 | Structure | Molecular formula | Mass (M + 1)+ |
|---|---|---|---|
| 32 | 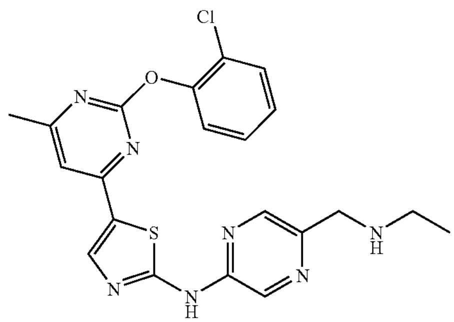 | C21H20ClN7OS | 454, 456 |
| 33 | 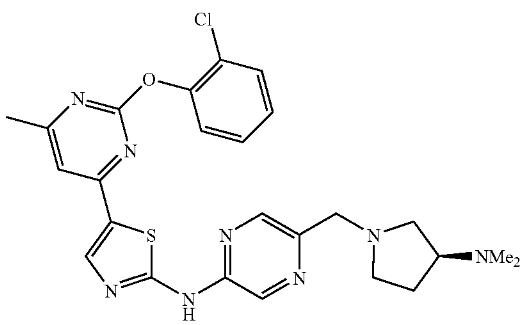 | C25H27ClN8OS | 523, 525 |
| 34 | 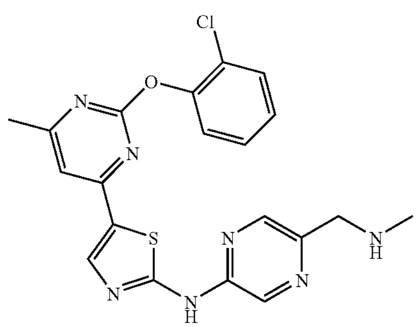 | C20H18ClN7OS | 440, 442 |
| 35 | 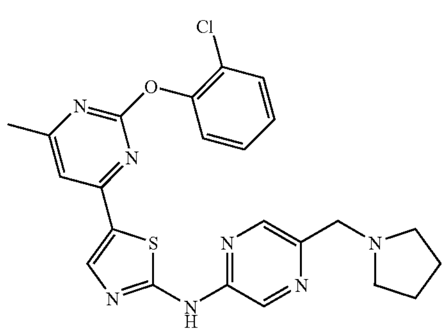 | C23H22ClN7OS | 480, 482 |

TABLE 9-continued

| Examples 32 to 36 | Structure | Molecular formula | Mass (M + 1)+ |
|---|---|---|---|
| 36 | 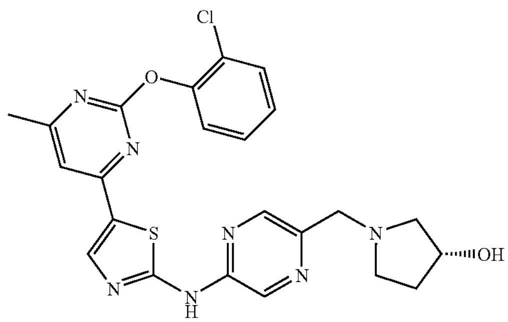 | C23H22ClN7O2S | 496, 498 |

TABLE 10

| Examples 37 to 41 | Structure | Molecular formula | Mass (M + 1)+ |
|---|---|---|---|
| 37 | 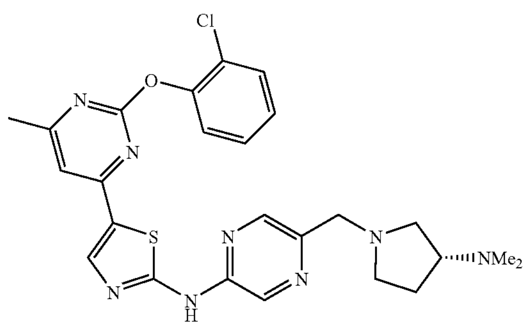 | C25H27ClN8OS | 523, 525 |
| 38 | 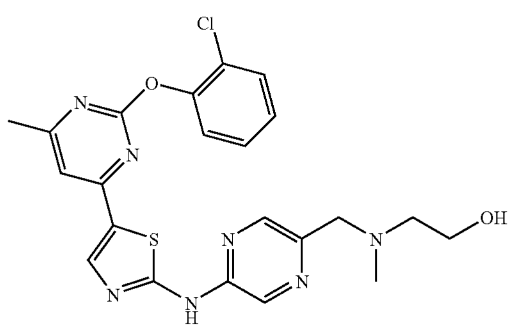 | C22H22ClN7O2S | 484, 486 |
| 39 | 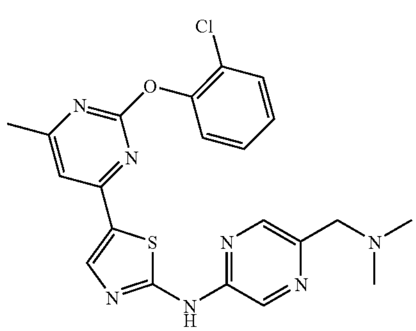 | C21H20ClN7OS | 454, 456 |

TABLE 10-continued

| Examples 37 to 41 | Structure | Molecular formula | Mass (M + 1)+ |
|---|---|---|---|
| 40 | 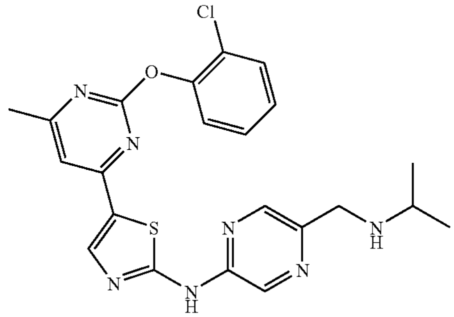 | C22H22ClN7OS | 468, 470 |
| 41 | 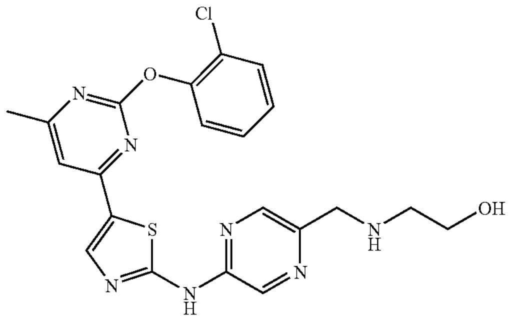 | C21H20ClN7O2S | 470, 472 |

Example 42

Synthesis of compound represented by following Formula [42]

[42]

(1) A benzyl alcohol product [42-1] was obtained from the sulfoxide product obtained in Example 1-(15) and 2-fluorophenol, according to the method of Example 27-(1).

[42-1]

The compound represented by the above Formula [42-1] was confirmed by LC-MS.

mass: 541 (M+1)+.

(2) The target compound [42] was obtained from the benzyl alcohol product [42-1] and N-methylpiperazine, according to the methods of Examples 8-22-(1) and (2). The target compound was confirmed by LC-MS.

mass: 493 (M+1)+.

Example 43

Synthesis of compound represented by following Formula [43]

[43]

(1) A benzyl alcohol product [43-1] was obtained from the sulfoxide product obtained in Example 1-(15) and 2,6-dichlorophenol, according to the method of Example 27-(1).

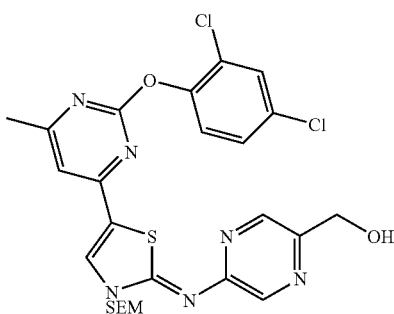

The compound represented by the above Formula [43-1] was confirmed by LC-MS.

mass: 591, 593 (M+1)⁺.

(2) The target compound [43] was obtained from the benzyl alcohol product [43-1] and N-methylpiperazine, according to the methods of Examples 8-22-(1) and (2). The target compound was confirmed by LC-MS.

mass: 543, 545 (M+1)⁺.

Example 44

Synthesis of compound represented by following Formula [44]

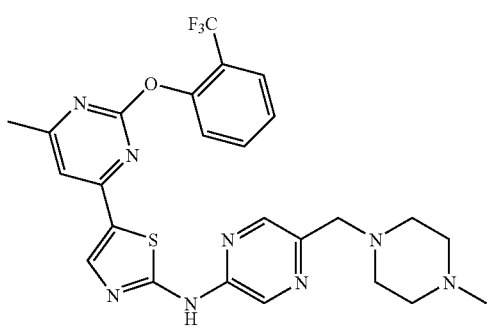

(1) A benzyl alcohol product [44-1] was obtained from the sulfoxide product obtained in Example 1-(15) and 2-trifluoromethylphenol, according to the method of Example 27-(1).

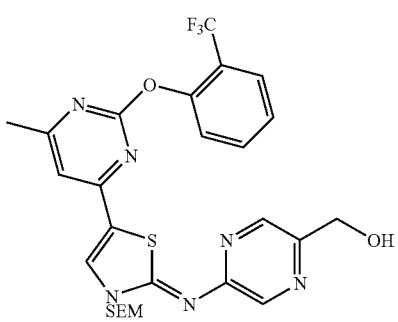

The compound represented by the above Formula [44-1] was confirmed by LC-MS.

mass: 591 (M+1)⁺.

(2) The target compound [44] was obtained from the benzyl alcohol product [44-1] and N-methylpiperazine, according to the methods of Examples 8-22-(1) and (2). The target compound was confirmed by LC-MS.

mass: 543 (M+1)⁺.

Example 45

Synthesis of compound represented by following Formula [45]

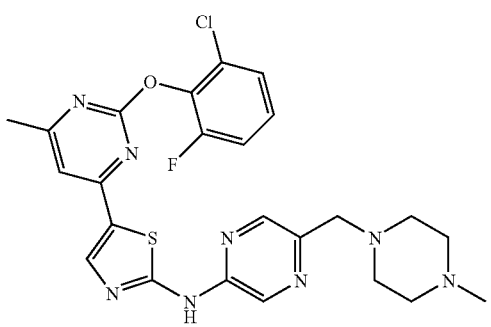

(1) A benzyl alcohol product [45-1] was obtained from the sulfoxide product obtained in Example 1-(15) and 2-chloro-6-fluorophenol, according to the method of Example 27-(1).

The compound represented by the above Formula [45-1] was confirmed by LC-MS.

mass: 575 (M+1)⁺.

(2) The target compound [45] was obtained from the benzyl alcohol product [45-1] and N-methylpiperazine, according to the methods of Examples 8-22-(1) and (2). The target compound was confirmed by LC-MS.

mass: 527 (M+1)⁺.

Example 46

Synthesis of compound represented by following Formula [46]

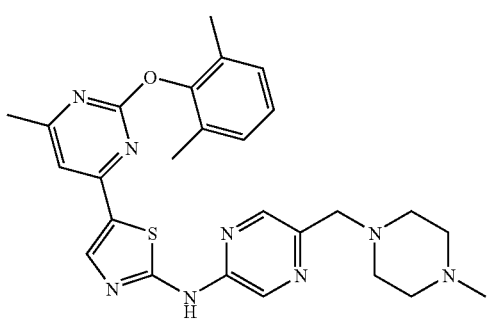

(1) A benzyl alcohol product [46-1] was obtained from the sulfoxide product obtained in Example 1-(15) and 2,6-dimethylphenol, according to the method of Example 27-(1).

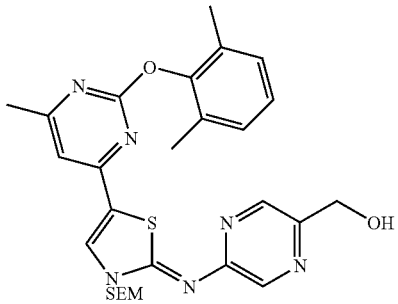

[46-1]

The compound represented by the above Formula [46-1] was confirmed by LC-MS.

mass: 551 (M+1)$^+$.

(2) The target compound [46] was obtained from the benzyl alcohol product [46-1] and N-methylpiperazine, according to the methods of Examples 8-22-(1) and (2). The target compound was confirmed by LC-MS.

mass: 503 (M+1)$^+$.

Examples 47-89

Synthesis of compounds represented by following General Formula [47-1] (wherein R$_a$ and R$_b$, which may be identical or different, are each a hydrogen atom, a lower alkyl group, a C$_3$-C$_8$ cycloalkyl group, or an aliphatic heterocyclic group, or R$_a$ and R$_b$ may together form an aliphatic heterocyclic ring, and the lower alkyl group, aliphatic heterocyclic group and cycloalkyl group may be substituted):

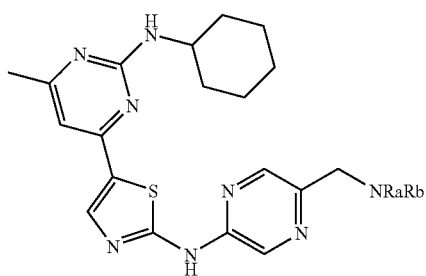

[47-1]

(1) The sulfoxide product obtained in Example 1-(15) and cyclohexylamine were heated to 90° C. in dimethylsulfoxide, and was stirred for 6 hours. The obtained reaction solution was cooled to room temperature, and the reaction solution was poured onto water, and was extracted with ethyl acetate. The extract was washed with water and saturated brine, dried and concentrated. The obtained residue was purified by column chromatography, and a benzyl alcohol product [47-2] was obtained according to the method of Example 1-(17).

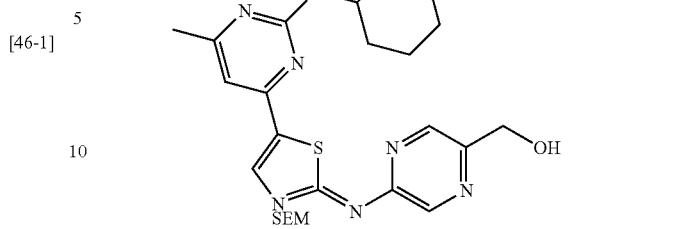

[47-2]

The spectral data of the compound represented by the above Formula [47-2] is presented below.

$^1$H-NMR (CDCl$_3$) δ: 8.46 (1H, s), 8.40 (1H, s), 7.72 (1H, s), 6.53 (1H, s), 5.60 (2H, s), 5.00 (1H, d, J=7.9 Hz), 4.77 (2H, s), 3.96-3.83 (1H, m), 3.76-3.68 (2H, m), 2.88-2.83 (1H, m), 2.34 (3H, s), 2.14-2.03 (2H, m), 1.83-1.17 (8H, m), 1.05-0.96 (2H, m), 0.02 (9H, s).

(2) The target compounds [47] to [89] (respectively corresponding to Examples 47 to 89) were obtained from the benzyl alcohol product [47-2] and isopropylamine (in the case of Example 47), dicyclopropylmethylamine (in the case of Example 48), 2-oxo-5-azabicyclo[2.2.1]heptane (in the case of Example 49), pyrrolidine (in the case of Example 50), cyclopropylamine (in the case of Example 51), ethylamine (in the case of Example 52), dimethylamine (in the case of Example 53), N-2-hydroxyethyl-N-methylamine (in the case of Example 54), N-methylpiperazine (in the case of Example 55), 1,4-dioxan-2-ylmethylamine (in the case of Example 56), tetrahydro-2-furanylmethyl (in the case of Example 57), methylamine (in the case of Example 58), 3-dimethylaminomethylpiperidine (in the case of Example 59), 1-(tetrahydro-2-furanyl)ethylamine (in the case of Example 60), 4-hydroxypiperidine (in the case of Example 61), N-(cyclohexyl)-N-methylamine (in the case of Example 62), 3-methyl-3-oxetanylamine (in the case of Example 63), (3R)-3-hydroxypyrrolidine (in the case of Example 64), (3S)-3-hydroxypyrrolidine (in the case of Example 65), (2R,3R)-3-hydroxy-2-methylpyrrolidine (in the case of Example 66), 3-acetylaminopyrrolidine (in the case of Example 67), N-(2-hydroxyethyl)piperazine (in the case of Example 68), N-benzylpiperazine (in the case of Example 69), N-Boc piperazine (in the case of Example 70), 4-acetyl-4-phenylpiperidine (in the case of Example 71), 4-(1-pyrrolidinyl)piperidine (in the case of Example 72), 3-ethoxycarbonylpiperidine (in the case of Example 73), morpholine (in the case of Example 74), 4-(4-piperidinyl)piperidine (in the case of Example 75), cyclopentylamine (in the case of Example 76), 2-hydroxyethylamine (in the case of Example 77), 3-dimethylaminopyrrolidine (in the case of Example 78), 2-dimethylaminoethylamine (in the case of 79), N-(1-methyl-2-piperidinyl)methyl-N-methylamine (in the case of Example 80), 1-(2-thienyl)ethylamine (in the case of Example 81), N-ethoxycarbonylpiperazine (in the case of Example 82), (2-methyl-4-thiazolyl)methylamine (in the case of Example 83), N-(1-methyl-3-piperidinyl)methyl-N-methylamine (in the case of Example 84), 2-trifluoromethylpyrrolidine (in the case of Example 85), N-(4-methyl-2-thiazolylmethyl)-N-methylamine (in the case of Example 86), 1-(4-methyl-2-thiazolyl)ethylamine (in the case of Example 87), 4-(2-benzoxazolyl)piperidine (in the case of Example 88), and 3-ethoxycarbonyl-4-piperidone (in the case of Example 89), respectively, according to the methods of Examples 8-22-(1) and (2). The target compounds were confirmed by LC-MS.

In addition, the method for synthesis of dicyclopropylmethylamine used in Example 48 is described in J. Org. Chem., 60, 7718 (1995); the method for synthesis of 2-oxo-5-azabicyclo[2.2.1]heptane used in Example 49 is described in J. Chem. Soc. Perkin. Trans., 1, 874 (1977); the method for synthesis of 3-dimethylaminomethylpiperidine used in Example 59 is described in Eur. J. Med. Chem. Chim. Ther., 37, 487 (2002); the method for synthesis of N-(1-methyl-2-piperidinyl)methyl-N-methylamine used in Example 80 is described in J. Med. Chem., 35, 4334 (1992); and the method for synthesis of 1-(4-methyl-2-thiazolyl)ethylamine used in Example 87 is described in J. Chem. Soc., 1372(1947).

TABLE 11

| Examples 47 to 51 | Structure | Molecular formula | Mass (M + 1)+ |
|---|---|---|---|
| 47 | 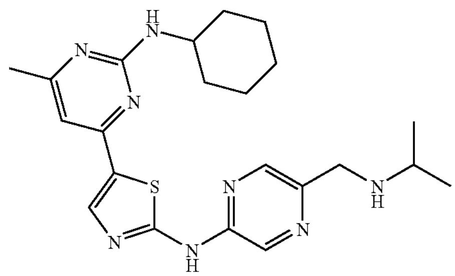 | C22H30N8S | 439 |
| 48 | 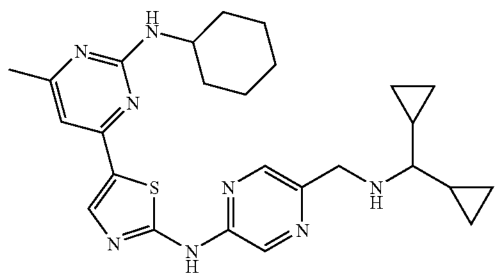 | C26H34N8S | 491 |
| 49 | 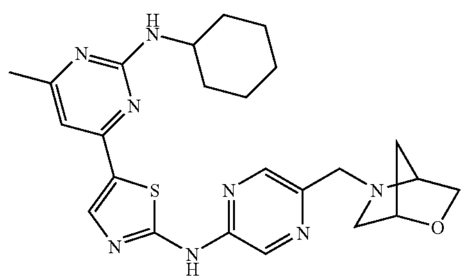 | C24H30N8OS | 479 |
| 50 | 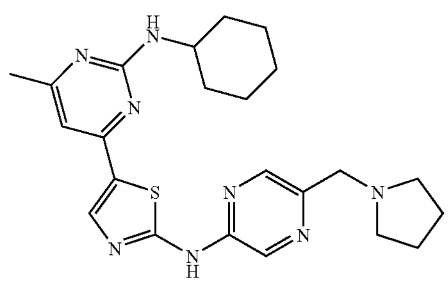 | C23H30N8S | 451 |
| 51 | 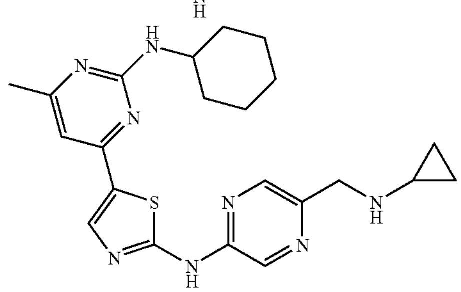 | C22H28N8S | 437 |

TABLE 12

| Examples 52 to 56 | Structure | Molecular formula | Mass (M + 1)+ |
|---|---|---|---|
| 52 | 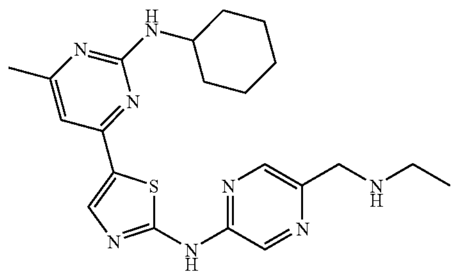 | C21H28N8S | 425 |
| 53 | 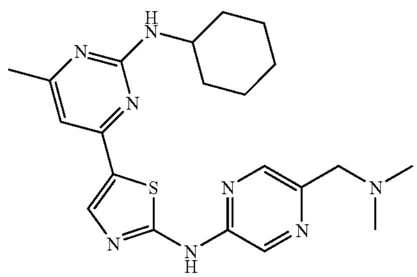 | C21H28N8S | 425 |
| 54 | 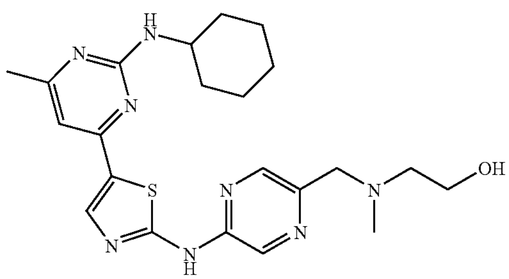 | C22H30N8OS | 455 |
| 55 | 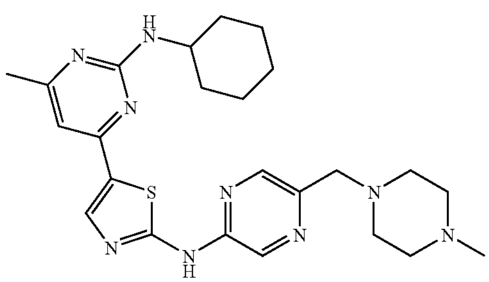 | C24H33N9S | 480 |
| 56 | 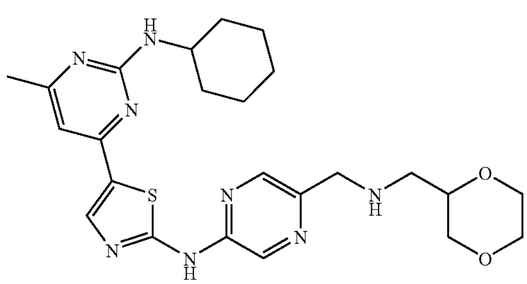 | C24H32N8O2S | 497 |

TABLE 13

| Examples 57 to 61 | Structure | Molecular formula | Mass (M + 1)+ |
|---|---|---|---|
| 57 | 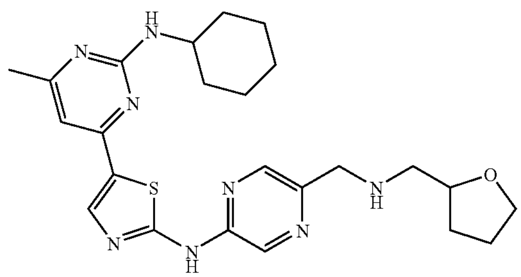 | C24H32N8OS | 481 |
| 58 | 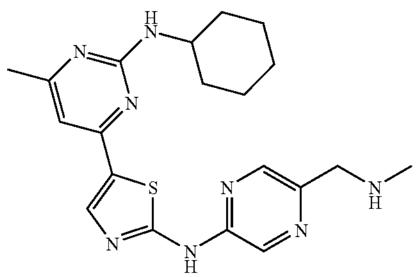 | C20H26N8S | 411 |
| 59 | 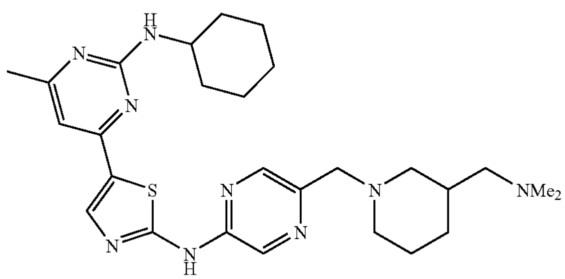 | C27H39N9S | 521 |
| 60 | 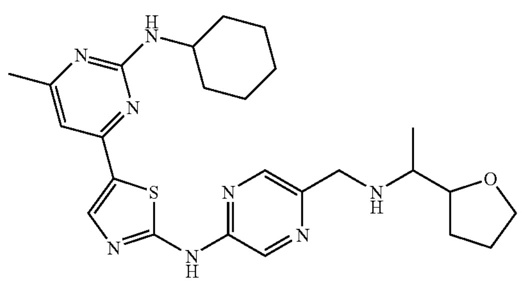 | C25H34N8OS | 495 |
| 61 | 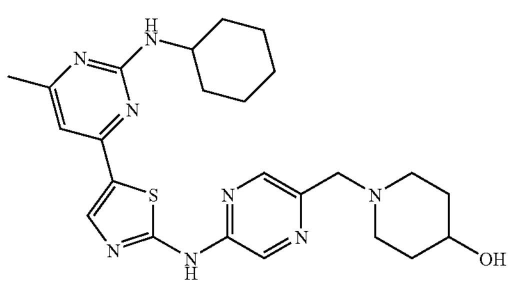 | C24H32N8OS | 481 |

TABLE 14

| Examples 62 to 66 | Structure | Molecular formula | Mass (M + 1)+ |
|---|---|---|---|
| 62 | 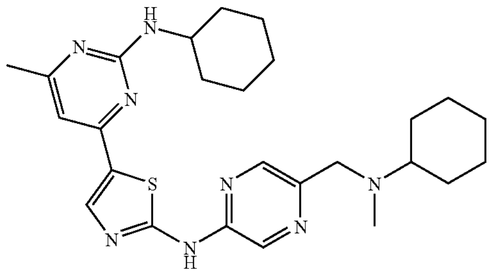 | C26H36N8S | 493 |
| 63 | 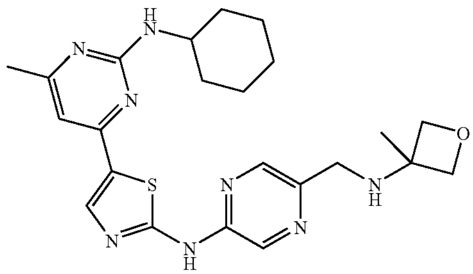 | C23H30N8OS | 467 |
| 64 | 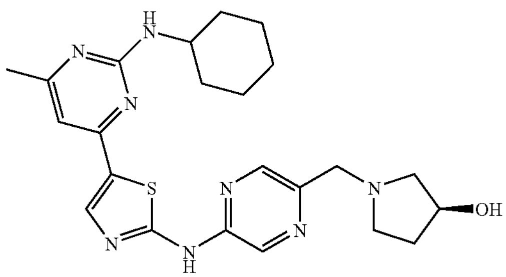 | C23H30N8OS | 467 |
| 65 | 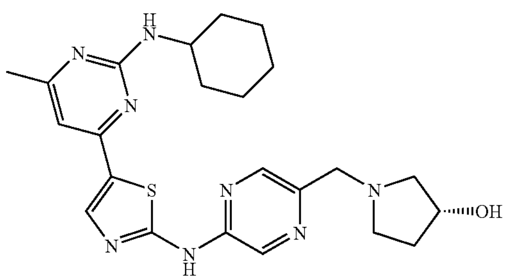 | C23H30N8OS | 467 |
| 66 | 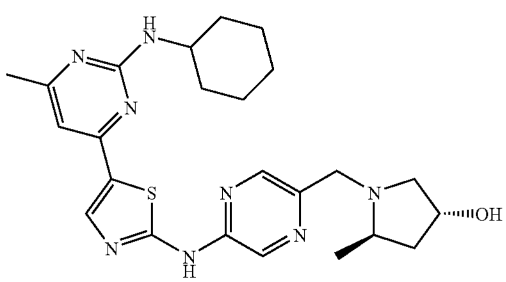 | C24H32N8OS | 481 |

TABLE 15

| Examples 67 to 71 | Structure | Molecular formula | Mass (M + 1)+ |
|---|---|---|---|
| 67 | 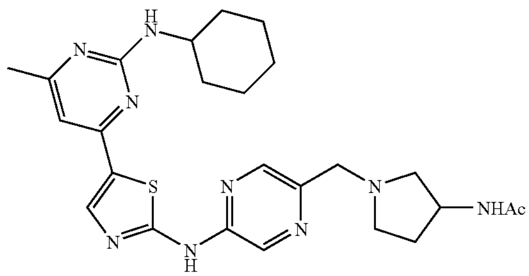 | C25H33N9OS | 508 |
| 68 | 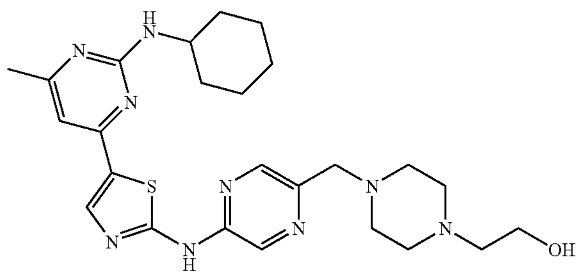 | C25H35N9OS | 510 |
| 69 | 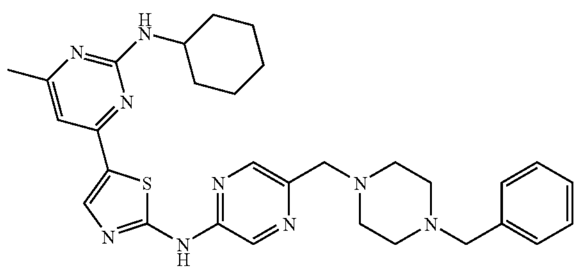 | C30H37N9S | 556 |
| 70 | 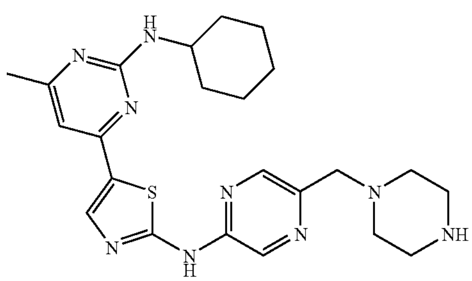 | C23H31N9S | 466 |
| 71 | 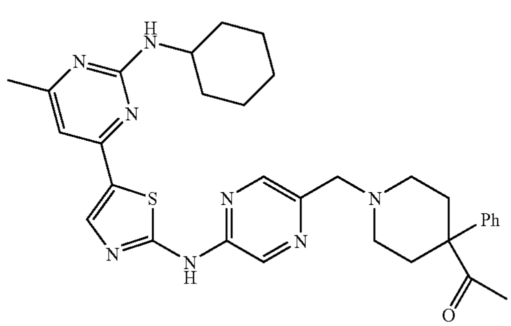 | C32H38N8OS | 583 |

TABLE 16
| Examples 72 to 76 | Structure | Molecular formula | Mass (M + 1)+ |
|---|---|---|---|
| 72 | 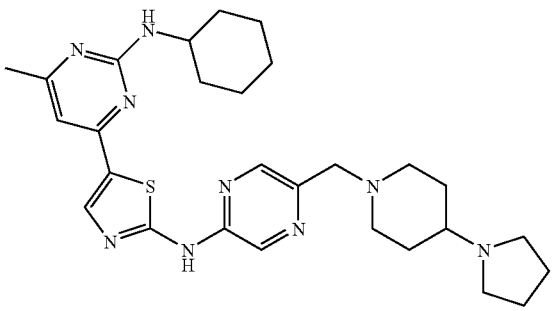 | C28H39N9S | 534 |
| 73 | 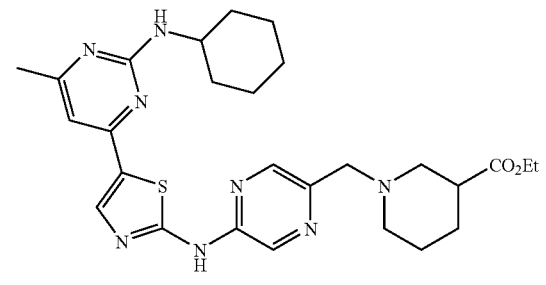 | C27H36N8O2S | 537 |
| 74 | 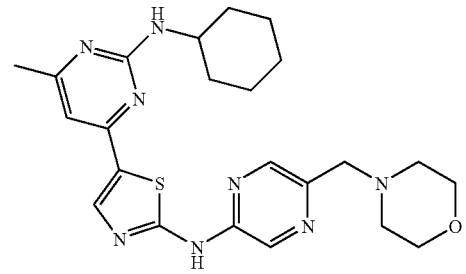 | C23H30N8OS | 467 |
| 75 | 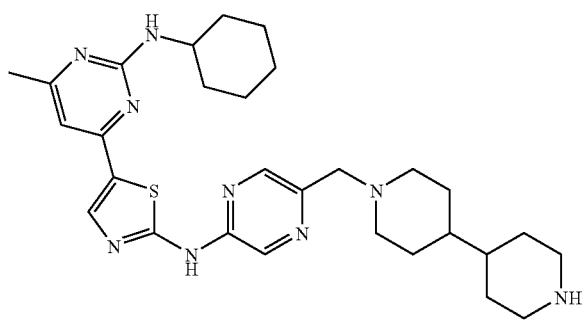 | C29H41N9S | 548 |
| 76 | 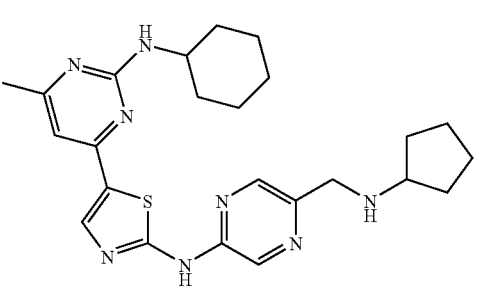 | C24H32N8S | 465 |

TABLE 17

| Examples 77 to 81 | Structure | Molecular formula | Mass (M + 1)+ |
|---|---|---|---|
| 77 | 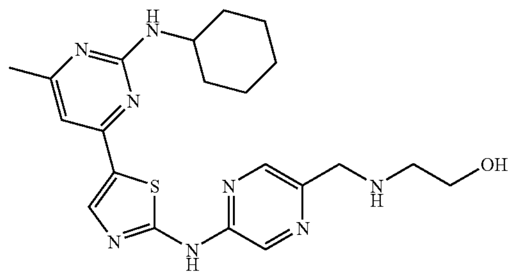 | C21H28N8OS | 441 |
| 78 | 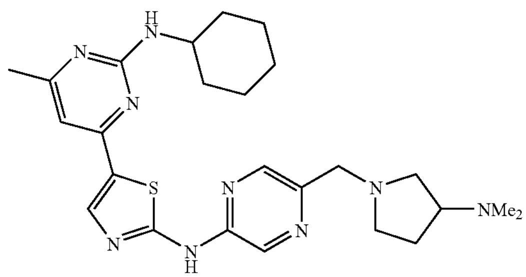 | C25H35N9S | 494 |
| 79 | 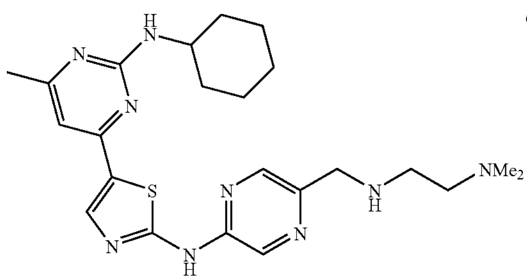 | C23H33N9S | 468 |
| 80 | 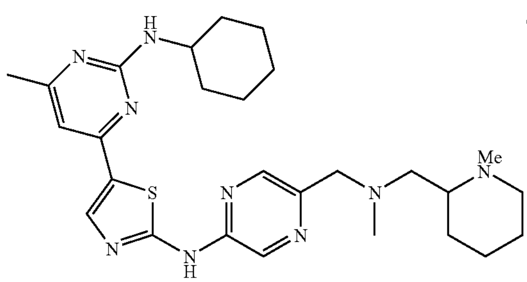 | C27H39N9S | 522 |
| 81 | 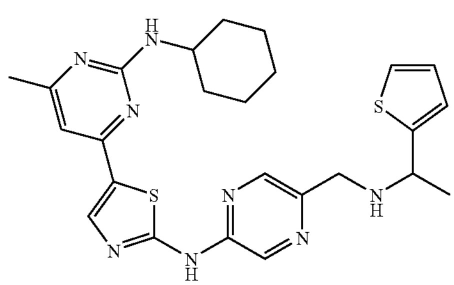 | C25H30N8S2 | 507 |

TABLE 18

| Examples 82 to 86 | Structure | Molecular formula | Mass (M + 1)+ |
|---|---|---|---|
| 82 | 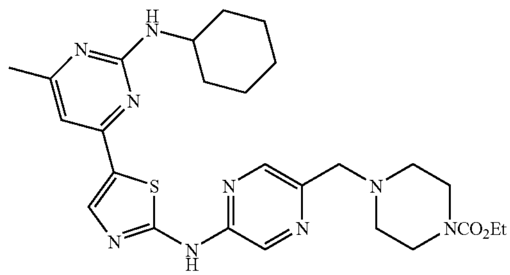 | C26H35N9O2S | 538 |
| 83 | 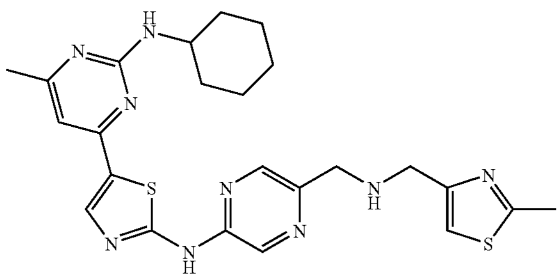 | C24H29N9S2 | 508 |
| 84 | 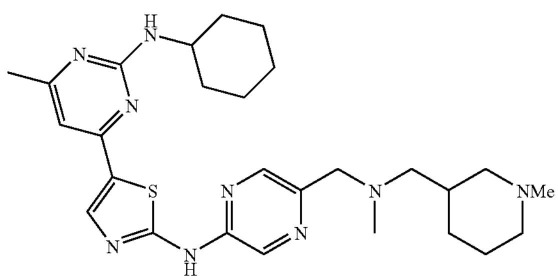 | C27H39N9S | 522 |
| 85 | 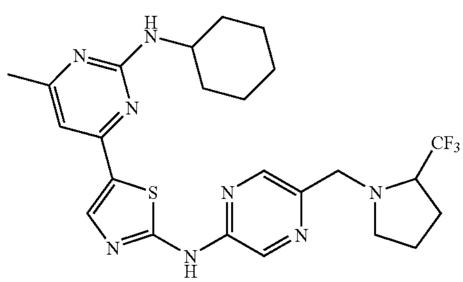 | C24H29F3N8S | 519 |
| 86 | 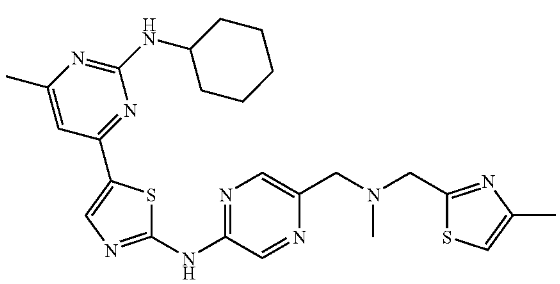 | C25H31N9S2 | 522 |

TABLE 19

| Examples 87 to 89 | Structure | Molecular formula | Mass (M + 1)+ |
|---|---|---|---|
| 87 | 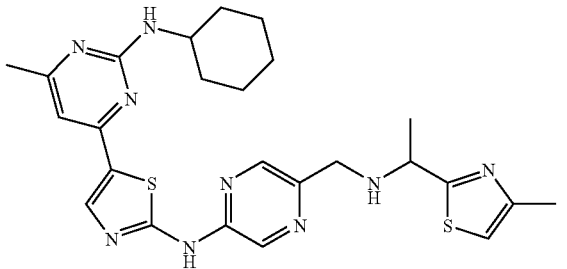 | C25H31N9S2 | 522 |
| 88 | 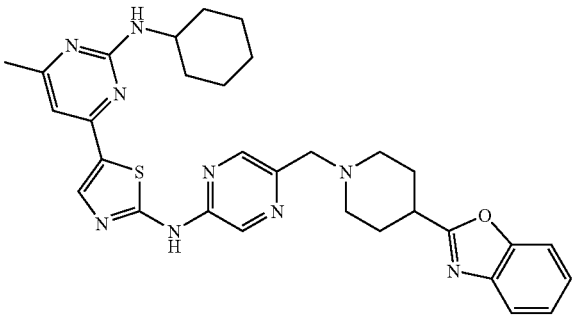 | C31H35N9OS | 582 |
| 89 | 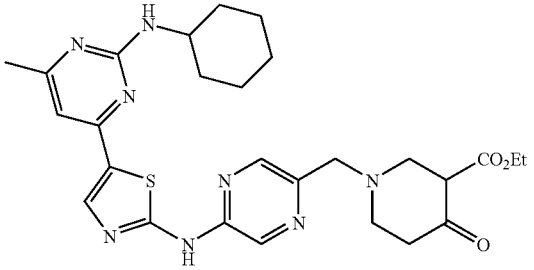 | C27H34N8O3S | 551 |

Example 90

Synthesis of compound represented by following Formula [90]

[90]

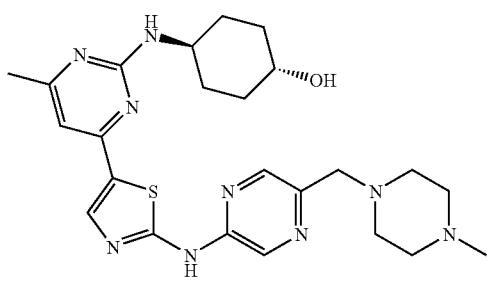

The target compound [90] was obtained from the sulfoxide product obtained in Example 1-(15), trans-4-hydroxycyclohexylamine and N-methylpiperazine, according to the methods of Examples 47-89, Examples 8-22-(1) and (2). The target compound was confirmed by LC-MS.

mass: 496 (M+1)+.

Examples 91-104

Synthesis of compounds represented by following General Formula [91-1] (wherein $R_a$ and $R_b$, which may be identical or different, are each a hydrogen atom, a lower alkyl group, a $C_3$-$C_8$ cycloalkyl group or an aliphatic heterocyclic group, or $R_a$ and $R_b$ may together form an aliphatic heterocyclic ring, and the lower alkyl group, aliphatic heterocyclic group and cycloalkyl group may be substituted):

[91-1]

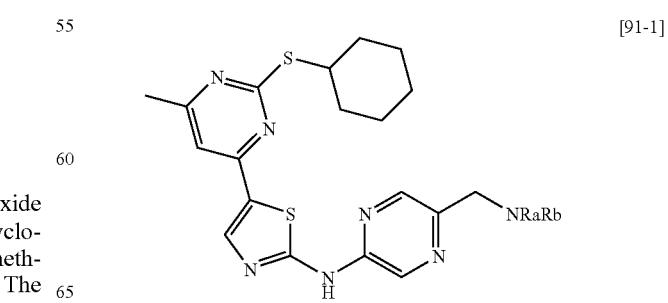

(1) A benzyl alcohol product [91-2] was obtained from the sulfoxide [1-15] obtained in Example 1-(15) and a sodium salt of cyclohexanethiol, according to the methods of Example 1-(16) and (17).

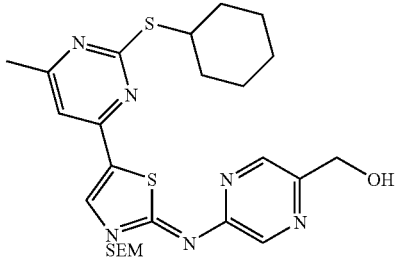

[91-2]

The compound represented by the above Formula [91-2] was confirmed by LC-MS.
mass: 545 (M+1)$^+$.

(2) The target compounds [91] to [104] (respectively corresponding to Examples 91 to 104) were obtained from the benzyl alcohol product [91-2] and ethylamine (in the case of Example 91), N-(2-hydroxyethyl)-N-methylamine (in the case of Example 92), pyrrolidine (in the case of Example 93), 3-dimethylaminopyrrolidine (in the case of Example 94), cyclopropylamine (in the case of Example 95), isopropylamine (in the case of Example 96), N-methylpiperazine (in the case of Example 97), cyclopentylamine (in the case of Example 98), 2-hydroxyethylamine (in the case of Example 99), 2-dimethylaminoethylamine (in the case of Example 100), N-(cyclohexyl)-N-methylamine (in the case of Example of 101), methylamine (in the case of Example 102), dimethylamine (in the case of Example 103), and 4-hydroxypiperidine (in the case of Example 104), respectively, according to the methods of Examples 8-22-(1) and (2). The target compounds were confirmed by LC-MS.

TABLE 20

| Examples 91 to 95 | Structure | Molecular formula | Mass (M + 1)$^+$ |
|---|---|---|---|
| 91 | 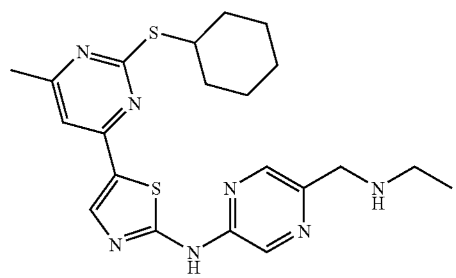 | C21H27N7S2 | 442 |
| 92 | 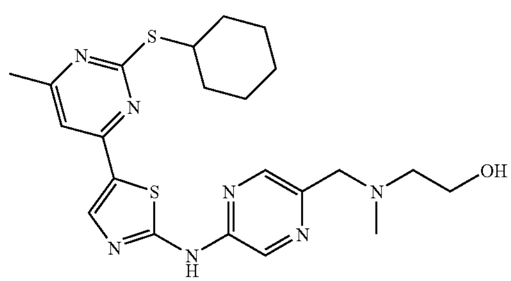 | C22H29N7OS2 | 472 |
| 93 | 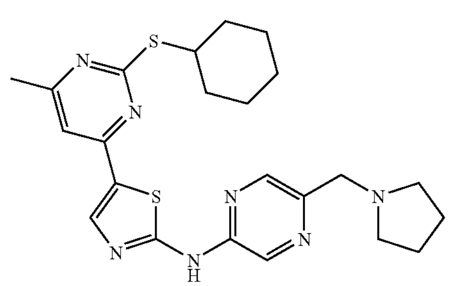 | C23H29N7S2 | 468 |

TABLE 20-continued
| Examples 91 to 95 | Structure | Molecular formula | Mass (M + 1)+ |
|---|---|---|---|
| 94 | 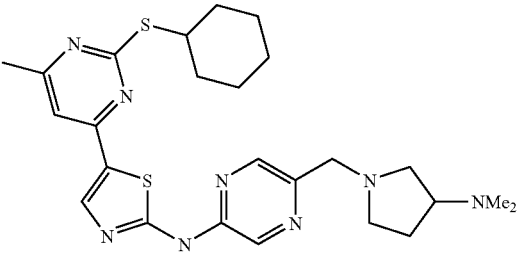 | C25H34N8S2 | 511 |
| 95 | 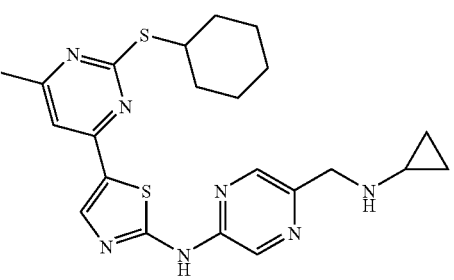 | C22H27N7S2 | 454 |
TABLE 21
| Examples 96 to 100 | Structure | Molecular formula | Mass (M + 1)+ |
|---|---|---|---|
| 96 | 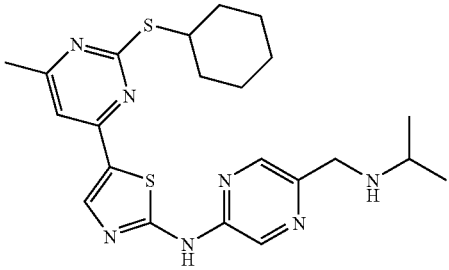 | C22H29N7S2 | 456 |
| 97 | 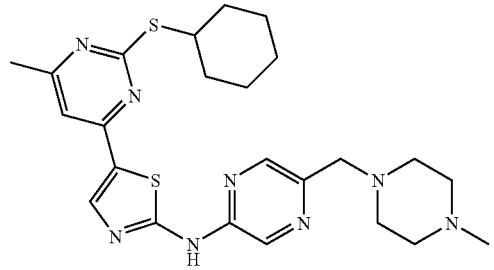 | C24H32N8S2 | 497 |
| 98 | 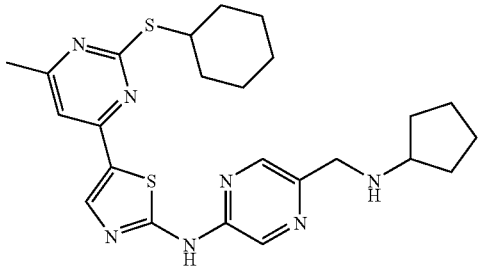 | C24H31N7S2 | 482 |

TABLE 21-continued

| Examples 96 to 100 | Structure | Molecular formula | Mass (M + 1)+ |
|---|---|---|---|
| 99 | 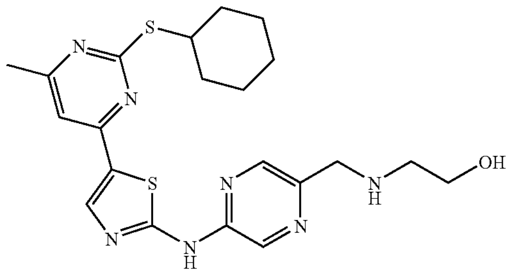 | C21H27N7OS2 | 458 |
| 100 | 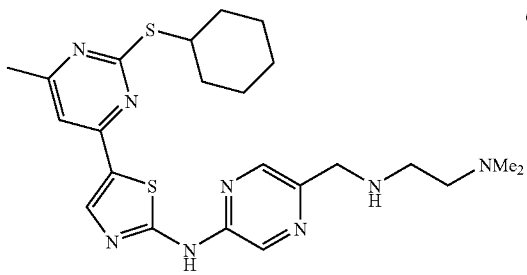 | C23H32N8S2 | 485 |

TABLE 22

| Examples 101 to 104 | Structure | Molecular formula | Mass (M + 1)+ |
|---|---|---|---|
| 101 | 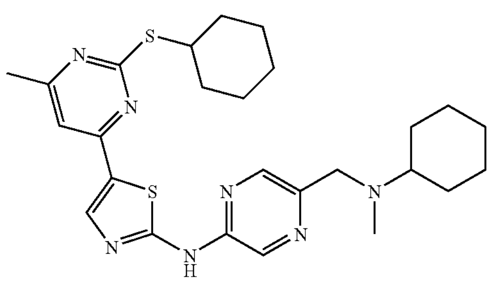 | C26H35N7S2 | 510 |
| 102 | 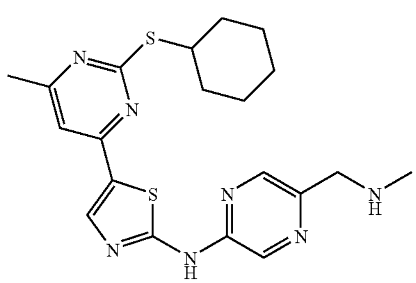 | C20H25N7S2 | 428 |

TABLE 22-continued

| Examples 101 to 104 | Structure | Molecular formula | Mass (M + 1)+ |
|---|---|---|---|
| 103 | 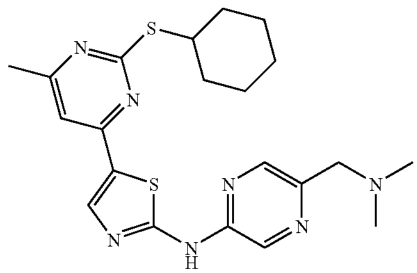 | C21H27N7S2 | 442 |
| 104 | 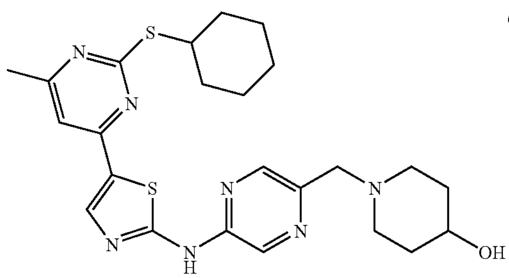 | C24H31N7OS2 | 498 |

Examples 105-118

Synthesis of compound represented by following General Formula [105-1] (wherein $R_a$ and $R_b$, which may be identical or different, are each a hydrogen atom, a lower alkyl group, a $C_3$-$C_8$ cycloalkyl group or an aliphatic heterocyclic group, or $R_a$ and $R_b$ may together form an aliphatic heterocyclic ring, and the lower alkyl group, aliphatic heterocyclic group and cycloalkyl group may be substituted):

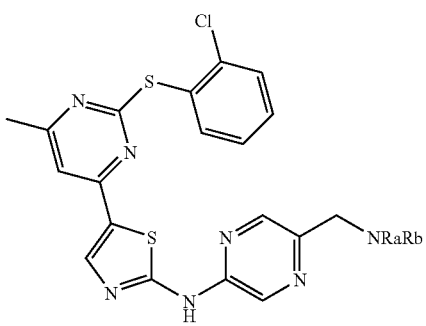

[105-1]

(1) A benzyl alcohol product [105-2] was obtained from the sulfoxide product [1-15] obtained in Example 1-(15) and 2-chlorothiophenol, according to the method of Example 27-(1).

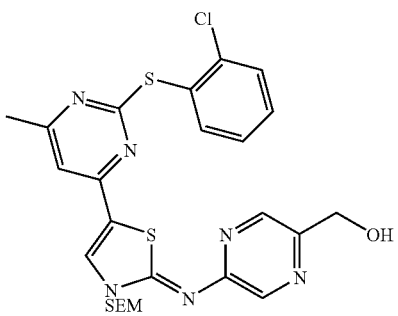

[105-2]

The compound represented by the above Formula [91-2] was confirmed by LC-MS.

mass: 573 (M+1)+.

(2) The target compounds [105] to [118] (respectively corresponding to Examples 105 to 118) were obtained from the benzyl alcohol product [105-2] and ethylamine (in the case of Example 105), isopropylamine (in the case of Example 106), methylamine (in the case of Example 107), 4-hydroxypiperidine (in the case of Example 108), N-methylpiperazine (in the case of Example 109), (2S)-2-hydroxymethylpyrrolidine (in the case of Example 110), dimethylamine (in the case of Example 111), 2-hydroxyethylamine (in the case of Example 112), pyrrolidine (in the case of Example 113), N-(2-hydroxyethyl)-N-methylamine (in the case of Example 114), (3S)-3-dimethylaminopyrrolidine (in the case of Example 115), (3S)-3-hydroxypyrrolidine (in the case of Example 116), (3R)-3-dimethylaminopyrrolidine (in the case of Example 117), and (3R)-3-hydroxypyrrolidine (in the case of Example 118), respectively, according to the methods of Examples 8-22-(1) and (2). The target compounds were confirmed by LC-MS.

TABLE 23

| Examples 105 to 108 | Structure | Molecular formula | Mass (M + 1)+ |
|---|---|---|---|
| 105 | 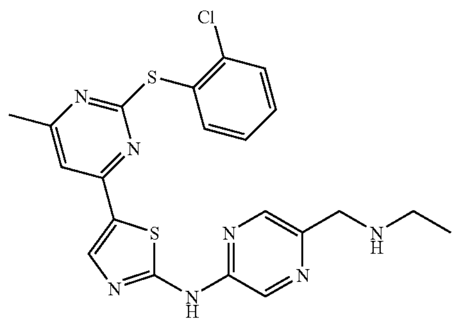 | C21H20ClN7S2 | 470, 472 |
| 106 | 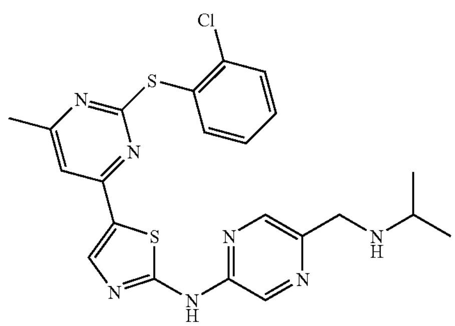 | C22H22ClN7S2 | 484, 486 |
| 107 | 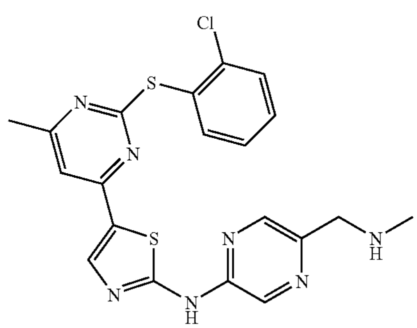 | C20H18ClN7S2 | 456, 458 |
| 108 | 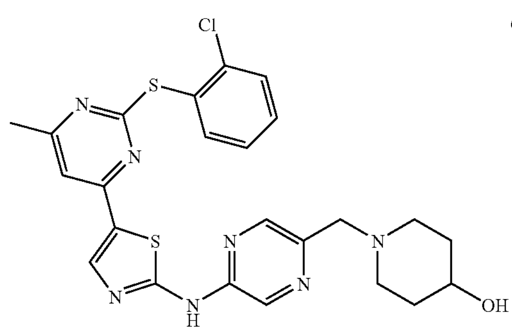 | C24H24ClN7OS2 | 526, 528 |

TABLE 24

| Examples 109 to 112 | Structure | Molecular formula | Mass (M + 1)+ |
|---|---|---|---|
| 109 | 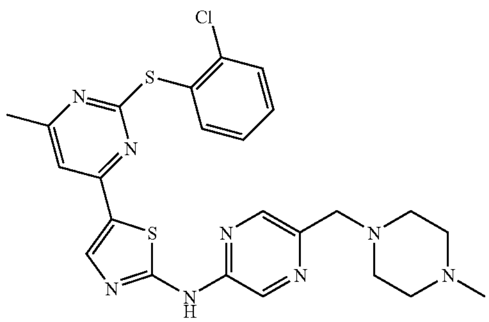 | C24H25ClN8S2 | 525, 527 |
| 110 | 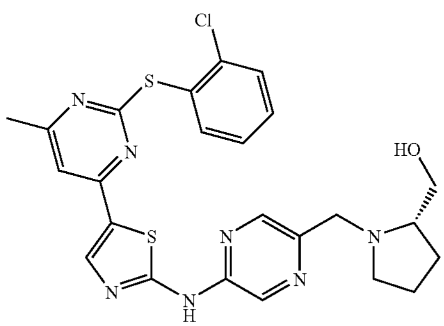 | C24H24ClN7OS2 | 526, 528 |
| 111 | 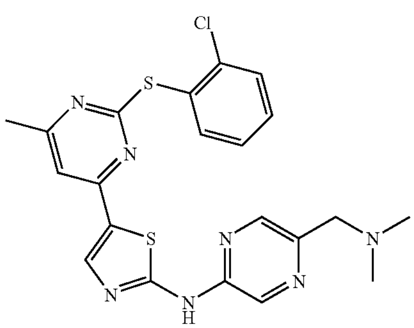 | C21H20ClN7S2 | 470, 472 |
| 112 | 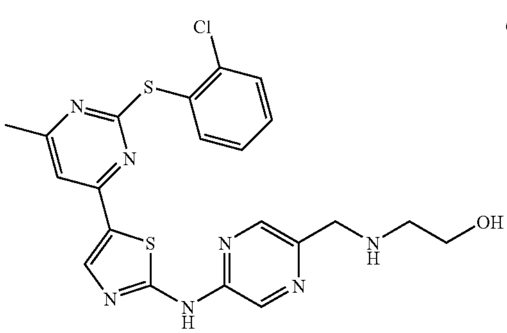 | C21H20ClN7OS2 | 486, 488 |

TABLE 25

| Examples 113 to 116 | Structure | Molecular formula | Mass (M + 1)+ |
|---|---|---|---|
| 113 | 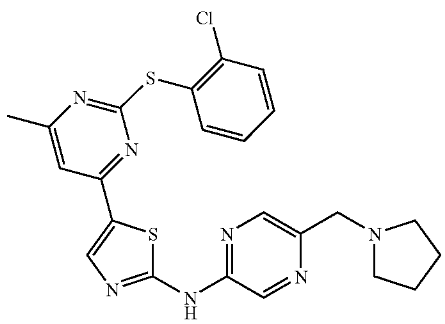 | C23H22ClN7S2 | 496, 498 |
| 114 | 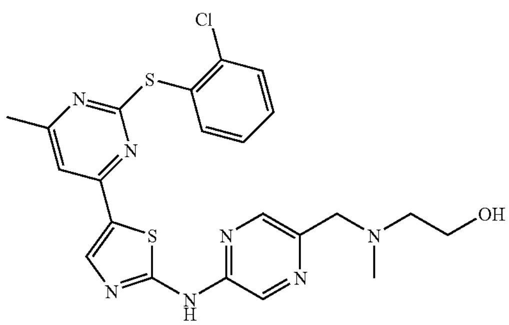 | C22H22ClN7OS2 | 500, 502 |
| 115 | 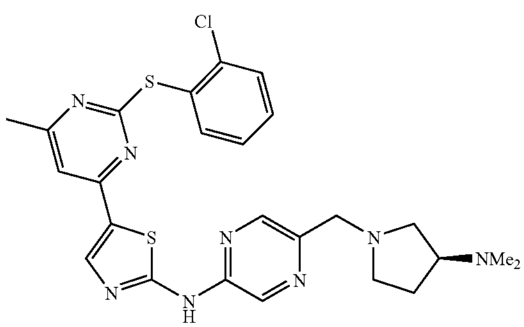 | C25H27ClN8S2 | 539, 541 |
| 116 | 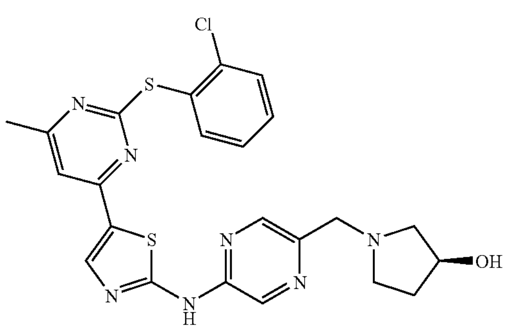 | C23H22ClN7OS2 | 512, 514 |

TABLE 26

| Examples 117 to 118 | Structure | Molecular formula | Mass (M + 1)+ |
|---|---|---|---|
| 117 | 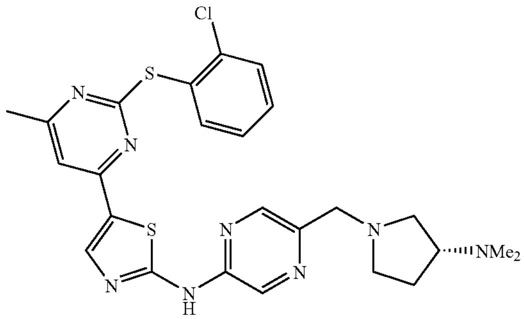 | C25H27ClN8S2 | 539, 541 |
| 118 | 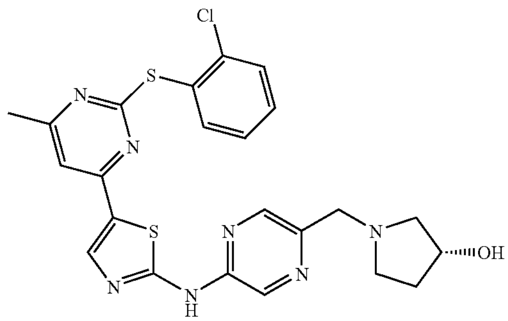 | C23H22ClN7OS2 | 512, 514 |

Example 119

Synthesis of compound represented by following Formula [119]

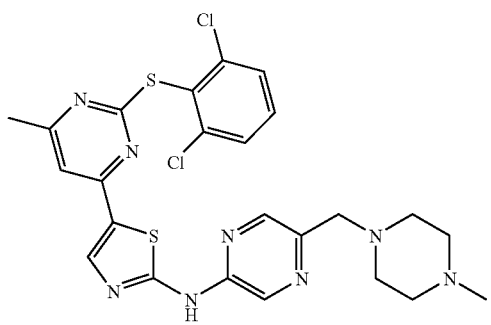

[119]

(1) A benzyl alcohol product [119-1] was obtained from the sulfoxide product [15-1] obtained in Example 1-(15) and 2,6-dichlorothiophenol, according to the method of Example 27-(1).

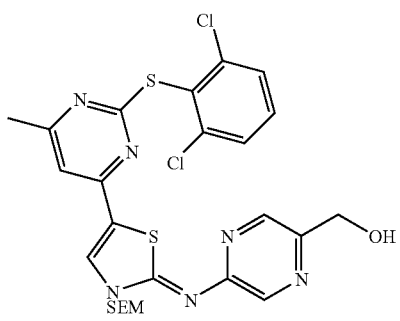

[119-1]

The compound represented by the above Formula [119-1] was confirmed by LC-MS.
mass: 607 (M+1)+.

(2) The target compound [119] was obtained from the benzyl alcohol product [119-1] and N-methylpiperazine, according to the methods of Examples 8-22-(1) and (2). The target compound was confirmed by LC-MS.
mass: 559, 561 (M+1)+.

Example 120

Synthesis of compound represented by following Formula [120]

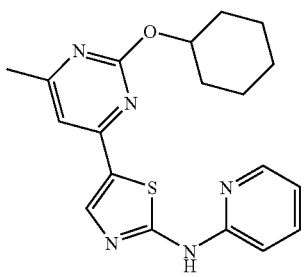

[120]

(1) A thiourea product [120-1] was obtained from 2-aminopyridine according to the methods of Example 1-(7) and (8).

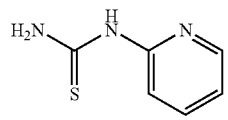

[120-1]

The spectral data of the compound represented by the above Formula [120-1] is presented below.

$^1$H-NMR (DMSO-d$_6$) δ: 10.85 (1H, brs), 10.76 (1H, brs), 9.14 (1H, brs), 8.46-8.02 (1H, m), 8.06-7.98 (1H, m), 7.44-7.37 (1H, m), 7.33-7.26 (1H, m).

(2) An α-bromoacetal product [120-2] was obtained from 4-chloro-2-methylthiopyrimidine, according to the methods of Example 1-(10) and (11).

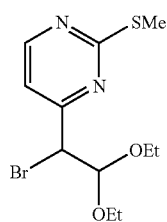

[120-2]

The spectral data of the compound represented by the above Formula [120-2] is presented below.

$^1$H-NMR (CDCl$_3$) δ: 8.49 (1H, d, J=5.1 Hz), 7.08 (1H, d, J=5.1 Hz), 5.04 (1H, d, J=6.9 Hz), 4.80 (1H, d, J=6.9 Hz), 3.83-3.46 (4H, m), 2.57 (3H, m), 1.25 (3H, t, J=7.2 Hz), 1.07 (3H, t, J=7.2 Hz).

(3) An aminothiazole product [120-3] was obtained from the thiourea product [120-1] and the α-bromoacetal product [120-2], according to the methods of Example 1-(12), (14), (15) and (16).

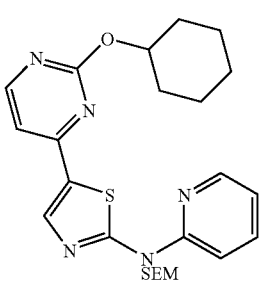

[120-3]

The spectral data of the compound represented by the above Formula [120-3] is presented below.

$^1$H-NMR (CDCl$_3$) δ: 8.50-8.42 (1H, m), 8.35-8.10 (1H, m), 8.08 (1H, s), 7.78-7.70 (1H, m), 7.40-7.35 (1H, m), 7.10-7.05 (1H, m), 7.05-7.00 (1H, m), 5.82 (2H, s), 5.10-5.00 (1H, m), 3.80-3.72 (2H, m), 2.20-2.10 (2H, m), 1.84-1.80 (2H, m), 1.70-1.60 (2H, m), 1.58-1.40 (2H, m), 1.38-1.20 (2H, m), 1.00-0.98 (2H, m), 0.02 (9H, s).

mass: 484 (M+1)$^+$.

(4) 134 mg of the aminothiazole product [120-3] was dissolved in 10 mL of THF, then MeLi was added at −78° C. to the solution, and the mixture was heated to 0° C. and stirred for 30 minutes. After adding water, the mixture was treated with 95 mg of 2,3-dichloro-5,6-dicyano-1,4-benzoquinone. The obtained reaction solution was stirred at room temperature for 30 minutes, and then was extracted with ethyl acetate. The ethyl acetate phase was washed with an aqueous solution of sodium hydroxide, dried, filtered and concentrated, and then the concentrate was purified by preparative thin layer chromatography to obtain 35 mg of a methylation product [120-4].

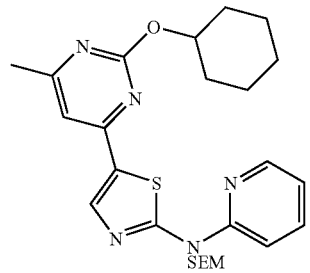

[120-4]

The spectral data of the compound represented by the above Formula [120-4] is presented below.

$^1$H-NMR (CDCl$_3$) δ: 8.48-8.40 (1H, m), 8.05 (1H, s), 7.78-7.70 (1H, m), 7.40-7.38 (1H, m), 7.05-7.00 (1H, m), 6.98 (1H, s), 5.84 (2H, s), 5.10-5.00 (1H, m), 3.80-3.72 (2H, m), 2.42 (3H, s), 2.10-2.06 (2H, m), 1.90-1.80 (2H, m), 1.70-1.58 (2H, m), 1.48-1.20 (4H, m), 1.00-0.96 (2H, m), 0.02 (9H, s).

mass: 498 (M+1)$^+$.

(5) 24 mg of the target compound [120] was obtained from 35 mg of the methylation product [120-4], according to the method of Example 1-(19).

The spectral data of the compound represented by the above Formula [120] is presented below.

$^1$H-NMR (DMSO-d$_6$) δ: 11.8 (1H, brs), 8.40-8.32 (2H, m), 7.80-7.74 (1H, m), 7.43 (1H, s), 7.13 (1H, d, J=8.3 Hz), 7.05-7.00 (1H, m), 5.08-4.92 (1H, m), 2.38 (3H, s), 2.05-1.95 (2H, m), 1.80-1.70 (2H, m), 1.60-1.25 (6H, m).

mass: 368 (M+1)$^+$.

Example 121

Synthesis of compound represented by following Formula [121]

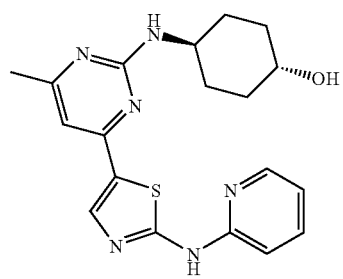

[121]

(1) A thiourea product [121-1] was obtained from 5-bromo-2-aminopyridine, according to the methods of Example 1-(7) and (8).

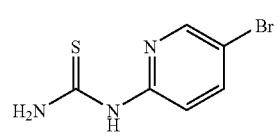

[121-1]

The spectral data of the compound represented by the above Formula [121-1] is presented below.

$^1$H-NMR (DMSO-d$_6$) δ: 10.66 (1H, brs), 10.17 (1H, brs), 8.99 (1H, brs), 8.35 (1H, d, J=2.8 Hz), 7.98 (1H, dd, J=2.8, 9.6 Hz), 7.14 (1H, d, J=9.6 Hz).

(2) An aminothiazole product [121-2] was obtained from the thiourea product [121-1] and the acetal product [1-11] obtained in Example 1-(11), according to the method of Example 1-(12).

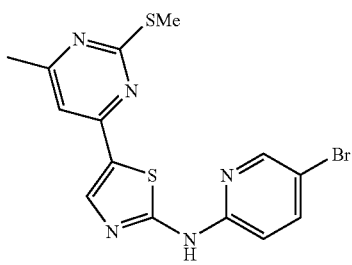

[121-2]

The spectral data of the compound represented by the above Formula [121-2] is presented below.

$^1$H-NMR (DMSO-d$_6$) δ: 11.82 (1H, brs), 8.50 (1H, d, J=2.0 Hz), 8.33 (1H, s), 7.95-7.92 (1H, m), 7.48 (1H, s), 7.09 (1H, d, J=10 Hz), 2.55 (3H, s), 2.40 (3H, s).

(3) 2.07 g of the aminothiazole product [121-2] was dissolved in 100 mL of dimethylformamide, and 560 mg of 60% sodium hydride was added to the solution at 0° C. After stirring at the same temperature for 15 minutes, 1.0 mL of chloromethyl methyl ether was added to the mixture. After stirring at the same temperature for 30 minutes, 100 mL of a saturated aqueous solution of sodium hydrogen carbonate was added to the mixture. A precipitate formed by further adding 100 mL of water was filtered and dried, and 2.2 g of a mixture of regioisomers of the protected product of aminothiazole [121-3-1] and [121-3-2] (about 2:1) was obtained as a yellow solid.

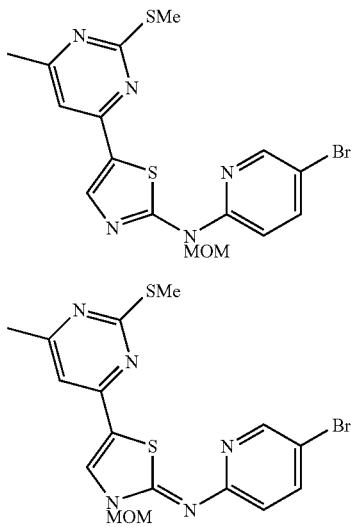

The spectral data of the compounds represented by the above Formula [121-3-1] and [121-3-2] are presented below.

Main isomer [121-3-1], $^1$H-NMR (CDCl$_3$) δ: 8.52 (1H, d, J=3.0, 0.8 Hz), 8.07 (1H, s), 7.81 (1H, dd, J=8.8, 3.0 Hz), 7.26 (1H, d, J=8.8, 3.0 Hz), 7.01 (1H, s), 5.80 (2H, s), 3.47 (3H, s), 2.62 (3H, s), 2.46 (3H, s).

Side isomer [121-3-2], $^1$H-NMR (CDCl$_3$) δ: 8.52 (1H, d, J=3.0, 0.8 Hz), 7.81 (1H, s), 7.69 (1H, dd, J=8.8, 3.0 Hz), 7.02 (1H, dd, J=8.8, 0.8 Hz), 6.84 (1H, s), 5.53 (2H, s), 3.46 (3H, s), 2.61 (3H, s), 2.46 (3H, s).

mass: 438, 440 (M+1)$^+$.

(4) 2.2 g of the mixture of regioisomers of the protected products of aminothiazole [121-3-1] and [121-3-2] was dissolved in 100 mL of tetrahydrofuran, and 9.0 mL of a 1.5 M hexane solution of n-butyllithium was added to the solution at −78° C. After stirring at the same temperature for 1 hour, 20 mL of a saturated aqueous solution of ammonium chloride was added to the mixture. The obtained reaction solution was extracted with ethyl acetate, and the organic phase was washed with water and saturated brine. This organic phase was dried over magnesium sulfate and filtered, and the filtrate was concentrated. The obtained residue was purified by silica gel column chromatography to obtain 1.7 g of a mixture of regioisomers of a debromination product [121-4-1] and [121-4-2] (about 2:1) was obtained as a brown oily product.

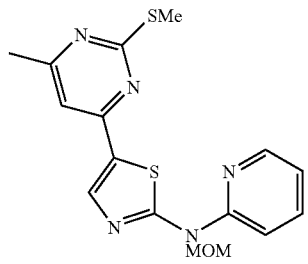

[124-4-1]

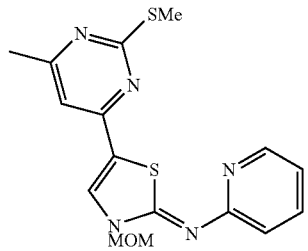

[124-4-2]

The spectral data of the compounds represented by the above Formula [121-4-1] and [121-4-2] are presented below.

Main isomer [121-4-1], $^1$H-NMR (CDCl$_3$) δ: 8.51-8.45 (1H, m), 8.09 (1H, s), 7.76-7.69 (1H, m), 7.34-7.29 (1H, m), 7.07-7.02 (1H, m), 7.00 (1H, s), 5.82 (2H, s), 3.49 (3H, s), 2.62 (3H, s), 2.45 (3H, s).

Side isomer [121-4-2], $^1$H-NMR (CDCl$_3$) δ: 8.51-8.45 (1H, m), 7.82 (1H, s), 7.65-7.58 (1H, m), 7.15-7.10 (1H, m), 6.93-6.89 (1H, m), 6.84 (1H, s), 5.54 (2H, s), 3.47 (3H, s), 2.61 (3H, s), 2.45 (3H, s).

mass: 360 (M+1)$^+$.

(5) 14.4 mg of the target compound [121] was obtained as a yellow solid, from 35 mg of the debromination product [121-4], according to the methods of Example 1-(15), (16) and (19).

The spectral data of the compound represented by the above Formula [121] is presented below.

$^1$H-NMR (DMSO-d$_6$) δ: 12.10 (1H, brs), 8.58 (1H, s), 8.39-8.32 (1H, m), 7.81 (1H, ddd, J=8.0, 6.8, 1.8 Hz), 7.31

(1H, s), 7.19 (1H, d, J=8.0 Hz), 7.07 (1H, dd, J=6.8, 5.6 Hz), 3.70-3.40 (2H, m), 2.41 (3H, brs), 2.10-1.80 (4H, m), 1.52-1.26 (4H, m).

mass: 383 (M+1)⁺.

Examples 122-124

Synthesis of compound represented by following General Formula [122-1] (wherein $R_a$ and $R_b$, which may be identical or different, are each a hydrogen atom, a lower alkyl group, a $C_3$-$C_8$ cycloalkyl group, or an aliphatic heterocyclic group, or $R_a$ and $R_b$ may together form an aliphatic heterocyclic ring, and the lower alkyl group, aliphatic heterocyclic group and cycloalkyl group may be substituted):

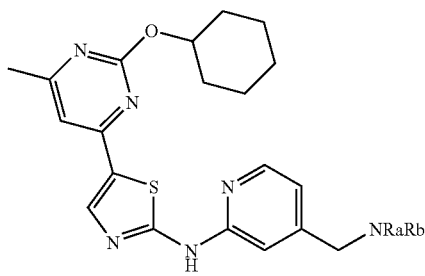

[122-1]

(1) 2-chloro-4-pyridinecarboxylic acid was dissolved in methanol, then thionyl chloride was added to the solution, and the mixture was stirred overnight at 80° C. The obtained reaction solution was concentrated and then poured onto water, and the reaction solution was extracted with ethyl acetate. The extract was washed with a saturated aqueous solution of sodium hydrogen carbonate and dried over anhydrous sodium sulfate, and the solvent was removed to obtain a methyl ester product [122-2].

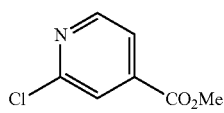

[122-2]

The spectral data of the compound represented by the above Formula [122-2] is presented below.

¹H-NMR (CDCl₃) δ: 8.55 (1H, dd, J=0.8, 4.8 Hz), 7.90-7.80 (1H, m), 7.78 (1H, dd, J=1.2, 4.8 Hz), 3.98 (3H, s).

(2) 18 g of the methyl ester product [122-2] and 21 mL of benzophenonimine were dissolved in 200 mL of toluene, then 47 g of cesium carbonate, 1.2 g of palladium acetate and 3.2 g of 2,2'-bis(diphenylphosphino)-1,1'-binaphthyl were added to the solution, and the mixture was stirred in a nitrogen atmosphere at 110° C. for 5 hours. The obtained reaction solution was cooled to 0° C., then a methanol solution of hydrogen chloride was added to the reaction solution, and the mixture was stirred at room temperature for 3 hours. The solvent was distilled off under reduced pressure, then the mixture was diluted with water, and sodium hydrogen carbonate was added to the dilution to neutralize the dilution. The aqueous phase was extracted with chloroform and dried, and the solvent was distilled off under reduced pressure. The residue was solidified from methanol and ether to obtain 4.6 g of a 2-aminopyridine product [122-3].

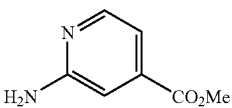

[122-3]

The spectral data of the compound represented by the above Formula [122-3] is presented below.

¹H-NMR (CD₃OD) δ: 8.17 (1H, d, J=5.6 Hz), 7.16-7.06 (1H, m), 7.06-7.05 (1H, m), 3.92 (3H, m).

(3) 900 mg of the 2-aminopyridine product [122-3] was dissolved in THF, and the solution was cooled to −78° C. 450 mg of lithium aluminum hydride was added to the solution, and the mixture was heated to 0° C. After stirring at the same temperature for 1 hour, sodium sulfate decahydrate was added to the mixture, and the mixture was stirred at room temperature. The obtained reaction solution was filtered through Celite, and the liquor was concentrated to obtain a benzyl alcohol product. 1.6 g of a protected product of benzyl alcohol [122-4] was obtained from the benzyl alcohol product, according to the method of Example 1-(5).

[122-4]

The spectral data of the compound represented by the above Formula [122-4] is presented below.

¹H-NMR (CDCl₃) δ: 8.00 (1H, d, J=5.6 Hz), 7.69-7.64 (4H, m), 7.46-7.36 (6H, m), 6.58-6.56 (2H, m), 4.67 (2H, s), 1.12 (9H, s).

(4) 2.0 g of a thiourea product [122-5] was obtained as a mixture with methyl benzoate, from 1.6 g of the protected product of benzyl alcohol [122-4], according to the methods of Example 1-(7) and (8).

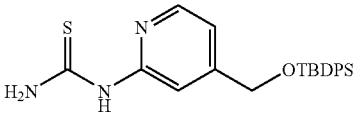

[122-5]

The spectral data of the compound represented by the above Formula [122-5] is presented below.

¹H-NMR (CDCl₃) δ: 11.03 (1H, brs), 8.18 (1H, brs), 8.12 (1H, d, J=5.6 Hz), 7.67-7.64 (4H, m), 7.44-7.36 (6H, m), 6.90-6.80 (2H, m), 6.78 (1H, s), 4.72 (2H, s), 1.13 (9H, s).

(5) 51 mg of a benzyl alcohol product [122-6] was obtained from 1.1 g of the thiourea product [122-5] and 800 mg of the acetal product [1-11], according to the methods of Example 1-(12), (13), (14), (15), (16) and (17).

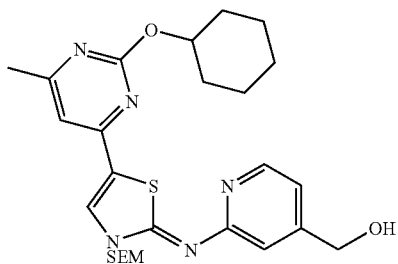

[122-6]

The spectral data of the compound represented by the above Formula [122-6] is presented below.

$^1$H-NMR (CDCl$_3$) δ: 8.45 (1H, d, J=8.0 Hz), 7.82 (1H, s), 7.11 (1H, s), 6.91 (1H, d, J=8.0 Hz), 6.80 (1H, s), 5.58 (2H, s), 5.12-5.03 (1H, m), 4.75 (2H, s), 3.75-3.60 (2H, m), 2.45 (3H, s), 2.15-1.12 (10H, m), 1.04-0.95 (2H, m), 0.03 (9H, s).

(6) The target compounds [122], [123] and [124] (respectively corresponding to Examples 122, 123 and 124) were obtained from the benzyl alcohol product [122-6] and N-ethylpiperazine (in the case of Example 122), dimethylamine (in the case of Example 123), and 4-hydroxypiperidine (in the case of Example 124), respectively, according to the methods of Example 8-22-(1) and (2). The target compounds were confirmed by LC-MS.

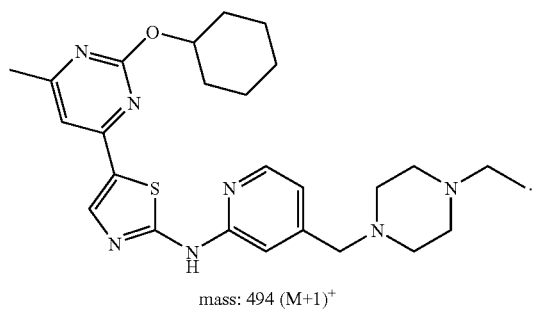

[122]

mass: 494 (M+1)$^+$

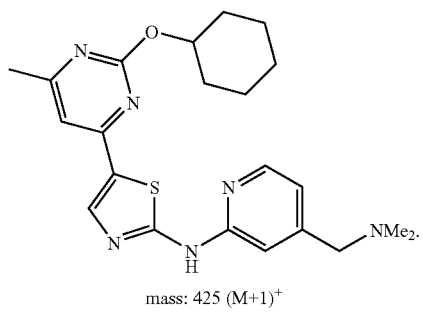

[123]

mass: 425 (M+1)$^+$

-continued

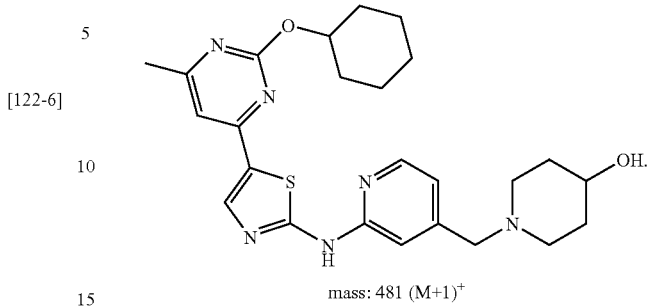

[124]

mass: 481 (M+1)$^+$

Example 125

Synthesis of compound represented by following Formula [125]

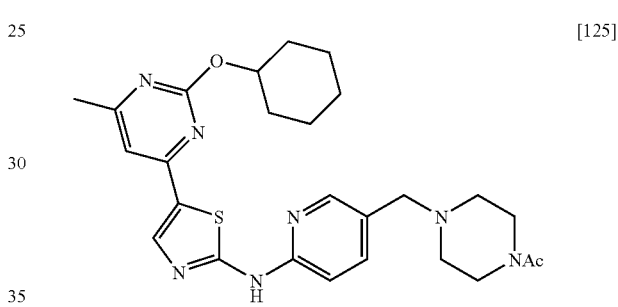

[125]

(1) 255 mg of the compound [121-4] obtained in Example 121-(4) was dissolved in a mixed solvent of 5 mL of DMF and 5 mL of methanol, and 1.02 mL of triethylamine, 54.8 mg of palladium acetate and 127 mg of 1,1'-bis(diphenylphosphino)ferrocene were added to the solution. The mixture was heated to 70° C. in a carbon monoxide atmosphere, and was stirred for two days. The obtained reaction solution was diluted with ethyl acetate, and then was washed with water, dried, filtered and concentrated. The concentrate was purified by silica gel column chromatography to obtain 139 mg of a methyl ester product [125-1].

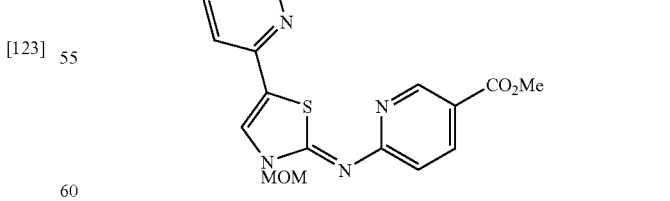

[125-1]

The spectral data of the compound represented by the above Formula [125-1] is presented below.

$^1$H-NMR (CDCl$_3$) δ: 9.10 (1H, s), 8.40-8.38 (1H, m), 7.82 (1H, s), 7.10-7.08 (1H, m), 6.85 (1H, s), 5.60 (2H, s), 3.98 (3H, s), 3.50 (3H, s), 2.62 (3H, s), 2.48 (3H, s).

mass: 418 (M+1)$^+$.

(2) 139 mg of the methyl ester product [125-1] obtained in Example 125-(1) was dissolved in a mixed solvent of 4 mL of THF and 4 mL of methanol, then 1 mL of a 1 N aqueous solution of sodium hydroxide was added to the solution, and the mixture was stirred at room temperature for 8 hours. The obtained reaction solution was concentrated, and then was acidified with 2 N hydrochloric acid. The reaction solution was extracted with a mixed solvent of chloroform-methanol, dried and concentrated to obtain a carboxylic acid product [125-2].

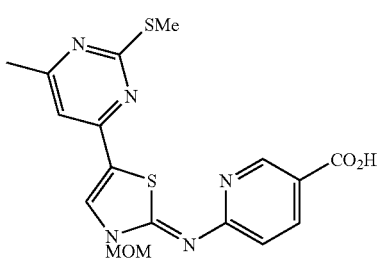

[125-2]

The spectral data of the compound represented by the above Formula [125-2] is presented below.

mass: 404 $(M+1)^+$.

(3) The carboxylic acid product [125-2] obtained in Example 125-(2) was dissolved in a mixed solvent of 5 mL of THF and 1 mL of DMF, then 270 mg of N,N'-carbonyldiimidazole was added to the solution at room temperature, and the mixture was stirred overnight at the same temperature. The obtained reaction solution was cooled in an ice bath, then 1 mL of an aqueous solution containing 61 mg of sodium borohydride was added to the reaction solution, and the mixture was stirred at the same temperature for 30 minutes. After adding a saturated aqueous solution of ammonium chloride, the reaction solution was extracted with ethyl acetate, and then washed with water, dried and concentrated. The crude product was purified by silica gel column chromatography to obtain 120 mg of a benzyl alcohol product [125-3].

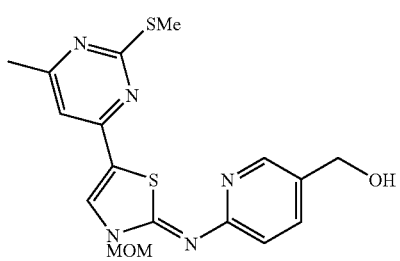

[125-3]

The spectral data of the compound represented by the above Formula [125-3] is presented below.

$^1$H-NMR (CDCl$_3$) δ: 8.45 (1H, s), 7.80 (1H, s), 7.68-7.62 (1H, m), 7.12-7.10 (2H, m), 6.82 (1H, m), 5.50 (2H, s), 4.70 (2H, s), 3.42 (3H, s), 2.62 (3H, s), 2.42 (3H, s).

(4) A sulfoxide product [125-4] was obtained from the benzyl alcohol product [125-3] obtained in Example 125-(3), according to the methods of Example 1-(13) and (15).

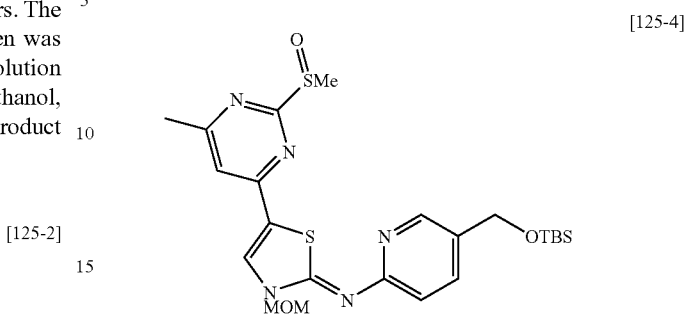

[125-4]

The spectral data of the compound represented by the above Formula [125-4] is presented below.

$^1$H-NMR (CDCl$_3$) δ: 8.43 (1H, s), 8.82 (1H, s), 8.63-8.58 (1H, m), 7.12-7.09 (1H, m), 7.83 (1H, s), 5.54 (2H, s), 4.73 (2H, s), 3.45 (3H, s), 2.99 (3H, s), 2.45 (3H, s), 0.95 (9H, s), 0.14 (6H, s).

(5) The target compound [125] was obtained as a hydrochloride salt, from the sulfoxide product [125-4] obtained in Example 125-(4), cyclohexanol and N-acetylpiperazine, according to the methods of Example 1-(16), (17), (18) and (19).

The spectral data of the compound represented by the above Formula [125] is presented below.

$^1$H-NMR (DMSO-d$_6$) δ: 11.8 (1H, brs), 10.7 (1H, brs), 8.46 (1H, d, J=2.0 Hz), 8.31 (1H, s), 7.91 (1H, dd, J=2.0, 8.8 Hz), 7.39 (1H, s), 7.16 (1H, d, J=8.8 Hz), 5.02-4.92 (1H, m), 4.49-4.25 (3H, m), 4.05-3.95 (1H, m), 3.50-3.30 (3H, m), 3.12-2.82 (3H, m), 2.37 (3H, s), 2.02 (3H, s), 2.05-1.95 (2H, m), 1.80-1.70 (2H, m), 1.60-1.25 (6H, m).

mass: 508 $(M+1)^+$.

Example 126

Synthesis of compound represented by following Formula [126]

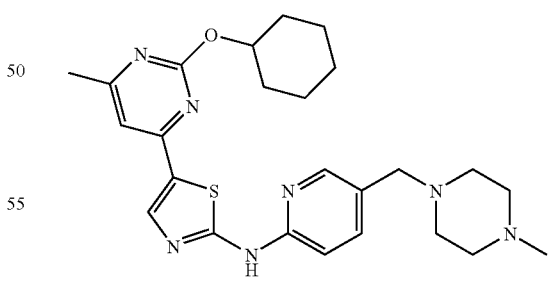

[126]

The target compound [126] was obtained from the sulfoxide product [125-4] obtained in Example 125-(4), cyclohexanol and N-methylpiperazine, according to the method of Example 125.

The spectral data of the compound represented by the above Formula [126] is presented below.

$^1$H-NMR (DMSO-d$_6$) δ: 11.9 (1H, brs), 8.53 (1H, brs), 8.36 (1H, s), 7.98 (1H, brs), 7.43 (1H, s), 7.19 (1H, d, J=8.8

Hz), 5.05-4.95 (1H, m), 4.00-3.20 (6H, m), 2.90-2.80 (4H, m), 2.40 (3H, s), 2.10 (3H, s), 2.10-2.00 (2H, m), 1.82-1.72 (2H, m), 1.62-1.28 (6H, m).

mass: 480 (M+1)$^+$.

Example 127

Synthesis of compound represented by following Formula [127]

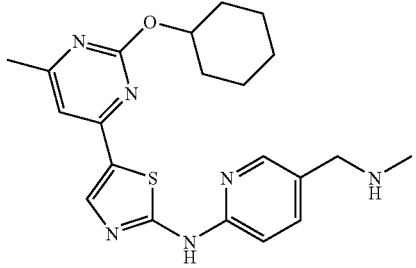
[127]

4.11 mg of the target compound [127] was obtained as a hydrochloride salt, from 11.9 mg of the benzyl alcohol product [125-3] obtained in Example 125-(3) and methylamine, according to the method of Example 125.

The spectral data of the compound represented by the above Formula [127] is presented below.

$^1$H-NMR (DMSO-d$_6$) δ: 11.93 (1H, brs), 9.25 (1H, brs), 8.49 (1H, s), 8.38 (1H, s), 7.95 (1H, d, J=8.7 Hz), 7.46 (1H, s), 7.18 (1H, d, J=8.7 Hz), 4.95-5.05 (1H, m), 4.10 (2H, brs), 2.5-2.48 (3H, brs), 2.39 (3H, s), 1.98-2.01 (2H, m), 1.74-1.76 (2H, m), 1.20-1.62 (6H, m).

mass: 411 (M+1)$^+$.

Example 128

Synthesis of compound represented by following Formula [128]

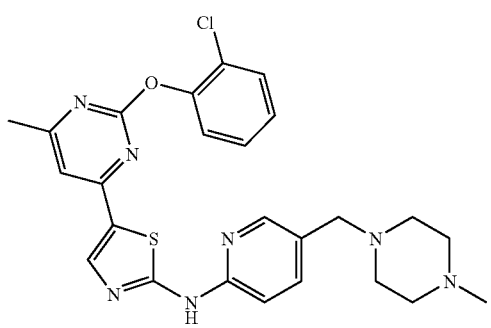
[128]

The target compound [128] was obtained from the compound of [125-4] obtained in Example 125 and 2-chlorophenol, according to the method of Example 27. The target compound was confirmed by LC-MS.

The spectral data of the compound represented by the above Formula [128] is presented below.

mass: 508 (M+1)$^+$.

Example 129

Synthesis of compound represented by following Formula [129]

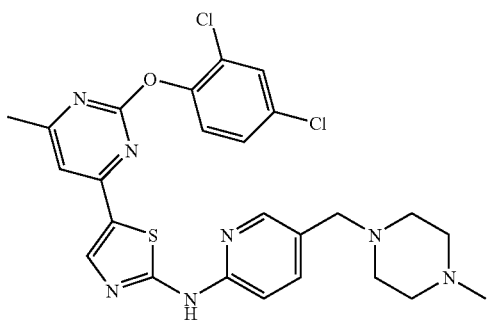
[129]

The target compound [129] was obtained from the compound of [125-4] obtained in Example 125 and 2,4-dichlorophenol, according to the method of Example 27. The target compound was confirmed by LC-MS.

The spectral data of the compound represented by the above Formula [129] is presented below.

mass: 542 (M+1)$^+$.

Example 130

Synthesis of compound represented by following Formula [130]

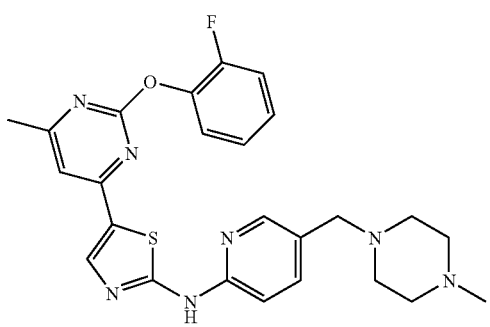
[130]

The target compound [130] was obtained from the compound of [125-4] obtained in Example 125 and 2-fluorophenol, according to the method of Example 27. The target compound was confirmed by LC-MS.

The spectral data of the compound represented by the above Formula [130] is presented below.

mass: 492 (M+1)$^+$.

Examples 131-144

Synthesis of compound represented by following General Formula [131-1] (wherein R$_a$ and R$_b$, which may be identical or different, are each a hydrogen atom, a lower alkyl group, a C$_3$-C$_8$ cycloalkyl group or an aliphatic heterocyclic group, or R$_a$ and R$_b$ may together form an aliphatic heterocyclic ring, and the lower alkyl group, aliphatic heterocyclic group and cycloalkyl group may be substituted):

[131-1]

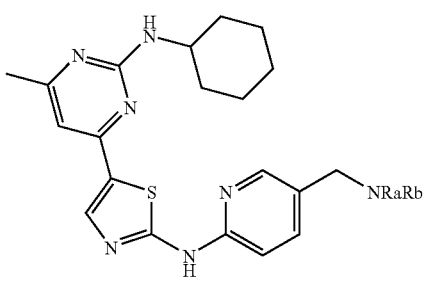

The target compounds [131] to [144] (respectively corresponding to Examples 131 to 144) were obtained from the compound [125-4] obtained in Example 125 and (3S)-3-dimethylaminopyrrolidine (in the case of Example 131), (3R)-3-dimethylaminopyrrolidine (in the case of Example 132), 2-methoxycarbonylpiperazine (in the case of Example 133), 4-hydroxymethylpiperidine (in the case of Example 134), 2-hydroxymethylpiperidine (in the case of Example 135), 3-hydroxypiperidine (in the case of Example 136), (2S)-2-hydroxymethylpyrrolidine (in the case of Example 137), (2R)-2-hydroxymethylpyrrolidine (in the case of Example 138), (3S)-pyrrolidin-3-ylcarbamic acid t-butyl ester (in the case of Example 139), (3R)-pyrrolidin-3-ylcarbamic acid t-butyl ester (in the case of Example 140), 3-hydroxymethylpiperidine (in the case of Example 141), 4-hydroxy-4-phenylpiperidine (in the case of Example 142), N-2-pyridylpiperazine (in the case of Example 143), or N-2-pyrimidylpiperazine (in the case of Example 144), respectively, according to the method of Examples 47-89. The target compounds were confirmed by LC-MS.

TABLE 27

| Examples 131 to 135 | Structure | Molecular formula | Mass (M + 1)+ |
|---|---|---|---|
| 131 | 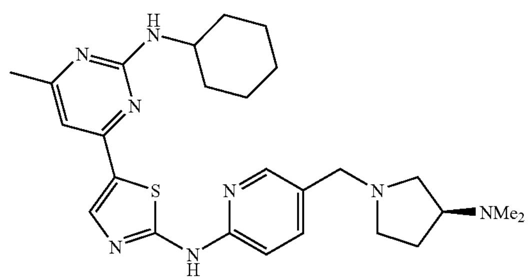 | C26H36N8S | 493 |
| 132 | 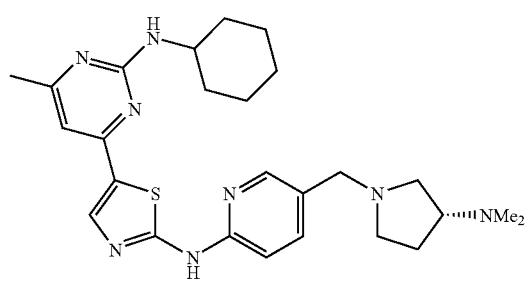 | C26H36N8S | 493 |
| 133 | 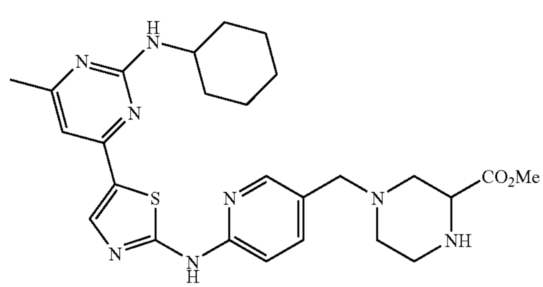 | C26H34N8O2S | 523 |

TABLE 27-continued
| Examples 131 to 135 | Structure | Molecular formula | Mass (M + 1)+ |
|---|---|---|---|
| 134 | 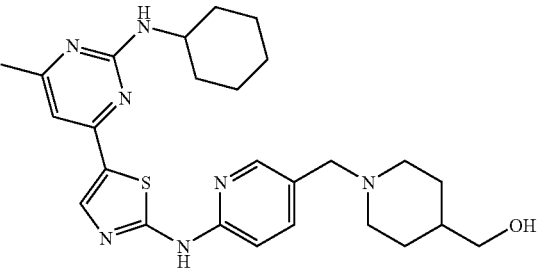 | C26H35N7OS | 494 |
| 135 | 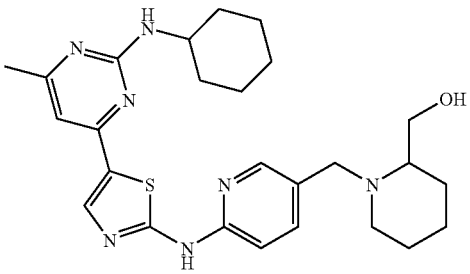 | C26H35N7OS | 494 |
TABLE 28
| Examples 136 to 140 | Structure | Molecular formula | Mass (M + 1)+ |
|---|---|---|---|
| 136 | 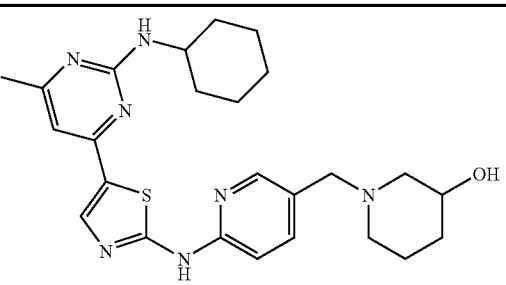 | C25H33N7OS | 480 |
| 137 | 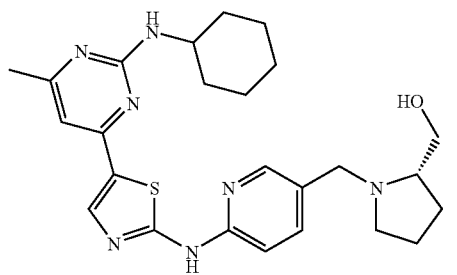 | C25H33N7OS | 480 |
| 138 | 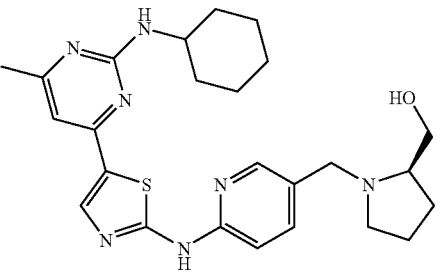 | C25H33N7OS | 480 |

TABLE 28-continued

| Examples 136 to 140 | Structure | Molecular formula | Mass (M + 1)+ |
|---|---|---|---|
| 139 | 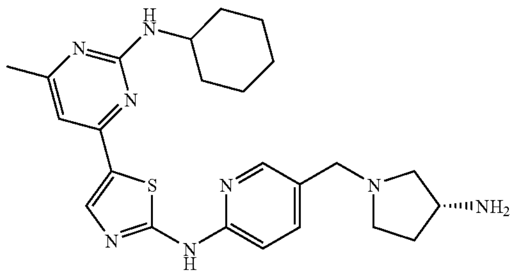 | C24H32N8S | 465 |
| 140 | 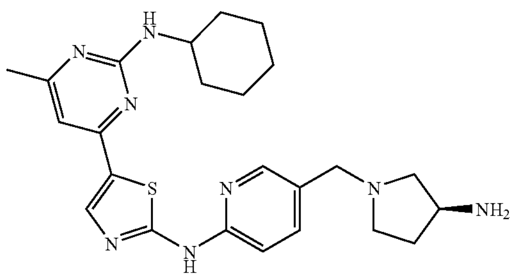 | C24H32N8S | 465 |

TABLE 29

| Examples 141 to 144 | Structure | Molecular formula | Mass (M + 1)+ |
|---|---|---|---|
| 141 | 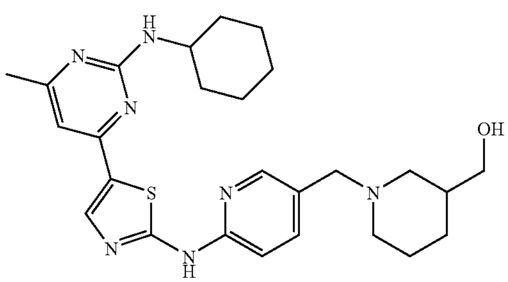 | C26H35N7OS | 494 |
| 142 | 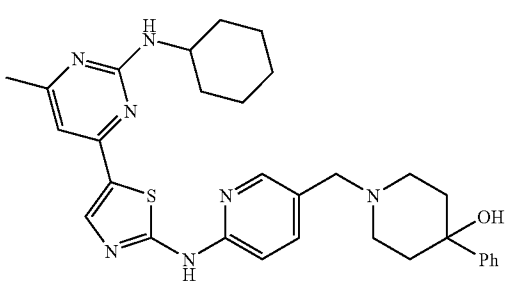 | C31H37N7OS | 556 |

TABLE 29-continued

| Examples 141 to 144 | Structure | Molecular formula | Mass (M + 1)+ |
|---|---|---|---|
| 143 | 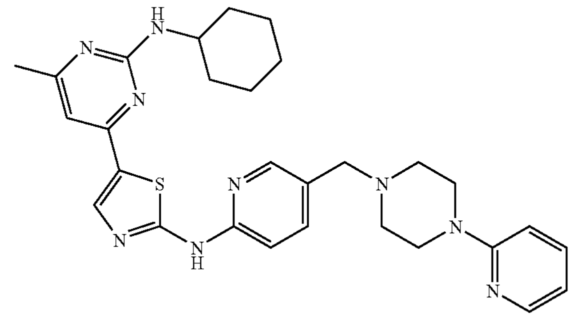 | C29H35N9S | 542 |
| 144 | 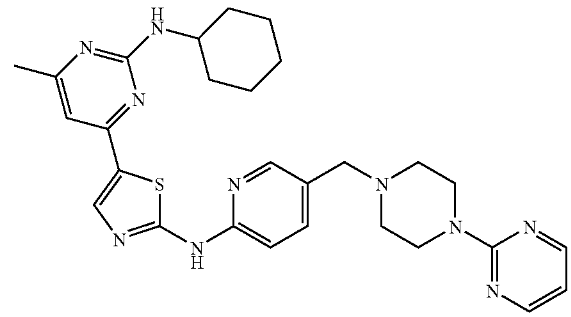 | C28H34N10S | 543 |

Example 145

Synthesis of compound represented by following Formula [145]

[145]

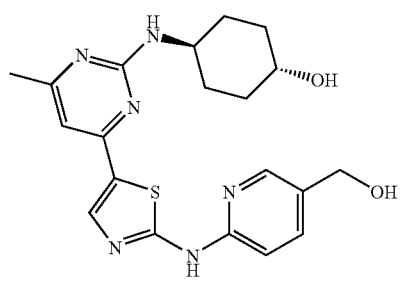

(1) A benzyl alcohol product [145-1] was obtained from the sulfoxide product [125-4] obtained in Example 125-(4) and trans-4-aminocyclohexanol, according to the method of Examples 47-89-(1).

mass: 543 (M+1)+.

[145-1]

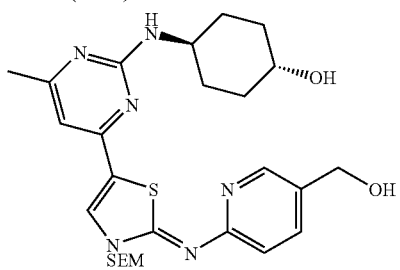

The spectral data of the compound represented by the above Formula [145-1] is presented below.

mass: 543 (M+1)+.

(2) The target compound [145] was obtained from the benzyl alcohol product [145-1], according to the method of Example 1-(19). The target compound was confirmed by LC-MS.

The spectral data of the compound represented by the above Formula [145] is presented below.

mass: 413 (M+1)+.

Example 146

Synthesis of compound represented by following Formula [146]

[146]

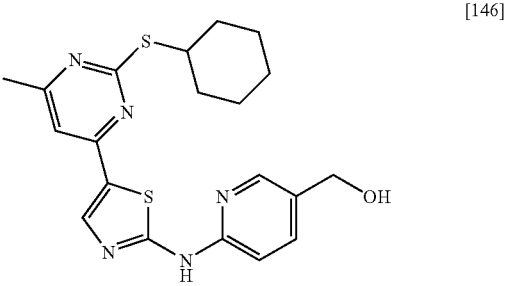

The target compound [146] was obtained from the compound of [125-4] obtained in Example 125, according to the methods of Examples 91-104. The target compound was confirmed by LC-MS.

mass: 414 (M+1)+.

Example 147

Synthesis of compound represented by following Formula [147]

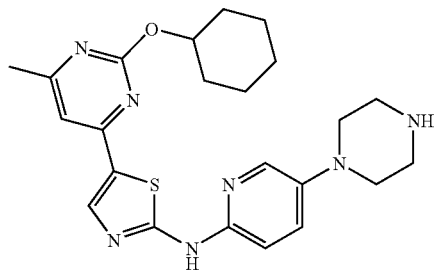

[147]

(1) 76 mg of a Compound [147-1] was obtained from 160 mg of the Compound [121-3-1] obtained in Example 121-(3), according to the methods of Example 1-(15) and (16).

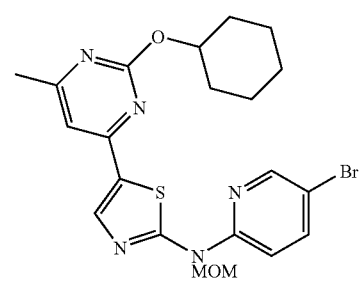

[147-1]

The spectral data of the compound represented by the above Formula [147-1] is presented below.

$^1$H-NMR (CDCl$_3$) δ: 8.48 (1H, s), 8.05 (1H, s), 7.82-7.78 (1H, m), 7.06-7.00 (1H, m), 6.98 (1H, m), 5.80 (2H, s), 5.10-5.00 (1H, m), 3.25 (3H, s), 2.20 (3H, s), 2.18-2.10 (2H, m), 1.92-1.82 (2H, m), 1.65-1.20 (6H, m).

mass: 490, 492 (M+1)$^+$.

(2) 76 mg of the Compound [147-1] and N-Boc piperazine were dissolved in toluene, then sodium t-butoxide, palladium acetate and 2,2'-bis(diphenylphosphino)-1,1'-binaphthyl were added to the solution, and the mixture was heated to 100° C. in a nitrogen atmosphere. The obtained reaction solution was stirred overnight at the same temperature and concentrated, and then the concentrate was purified by silica gel column chromatography to obtain 26 mg of a coupling product [147-2].

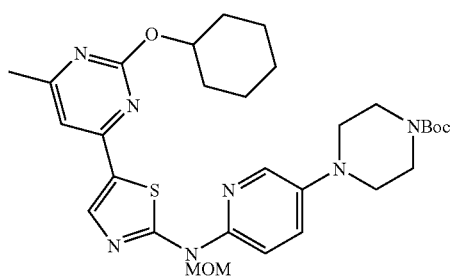

[147-2]

The spectral data of the compound represented by the above Formula [147-2] is presented below.

$^1$H-NMR (CDCl$_3$) δ: 8.16-8.14 (1H, m), 8.04 (1H, s), 7.40-7.36 (1H, m), 7.32-7.28 (1H, m), 6.92 (1H, s), 5.75 (2H, s), 5.10-5.00 (1H, m), 3.68-3.62 (4H, m), 3.48 (3H, s), 3.20-3.14 (4H, m), 2.04 (3H, s), 2.20-2.10 (2H, M), 1.90-1.80 (2H, m), 1.70-1.1.28 (15H, m).

mass: 596 (M+1)$^+$.

(3) To the Compound [147-2], a 4 N dioxane solution of hydrogen chloride was added, and the mixture was stirred at room temperature for 2 hours. The solvent of the reaction solution was concentrated, and then the residue was solidified from methanol and ether to obtain the target compound [147] as a hydrochloride salt.

The spectral data of the compound represented by the above Formula [147] is presented below.

$^1$H-NMR (DMSO-d$_6$) δ: 11.5 (1H, brs), 8.88 (2H, brs), 8.25 (1H, s), 8.10 (1H, s), 7.54 (1H, dd, J=2.9, 9.3 Hz), 7.34 (1H, s), 7.07 (1H, d, J=9.3 Hz), 5.05-4.93 (1H, m), 3.38-3.30 (4H, m), 3.28-3.20 (4H, m), 2.36 (3H, s), 2.03-1.95 (2H, m), 1.80-1.70 (2H, m), 1.60-1.25 (6H, m).

mass: 452 (M+1)$^+$.

Example 148

Synthesis of compound represented by following Formula [148]

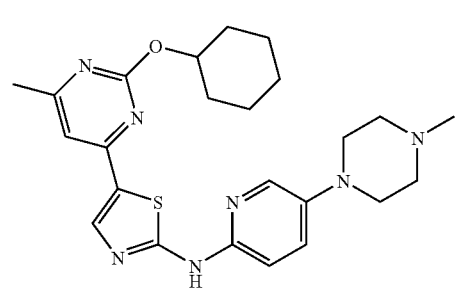

[148]

12 mg of the Compound [147] obtained in Example 147 was dissolved in 1 mL of methanol and 0.5 mL of chloroform, and formalin was added to the solution. To this mixture, a methanol solution of zinc chloride and sodium borocyanohydride was added, and the mixture was stirred at room temperature for 1 hour. After adding a saturated aqueous solution of sodium hydrogen carbonate, the mixture was extracted with chloroform, dried, filtered, and concentrated. The reaction mixture was purified by preparative thin layer chromatography, and a 4 N dioxane solution of hydrogen chloride was added thereto. The reaction solution was concentrated, and then the residue was solidified from methanol and ether to obtain 4 mg of the target compound [148] as a hydrochloride salt.

The spectral data of the compound represented by the above Formula [148] is presented below.

$^1$H-NMR (DMSO-d$_6$) δ: 11.50 (1H, brs), 10.20 (1H, brs), 8.26 (1H, s), 8.11 (1H, d, J=2.9 Hz), 7.55 (1H, dd, J=2.9, 8.7 Hz), 7.35 (1H, s), 7.07 (1H, d, J=8.7 Hz), 5.30-4.30 (1H, m), 3.80-3.70 (2H, m), 3.55-3.45 (2H, m), 3.22-3.10 (2H, m), 3.10-3.00 (2H, m), 2.82 (3H, d, J=4.9 Hz), 2.36 (3H, s), 2.10-1.91 (2H, m), 1.80-1.70 (2H, m), 1.60-1.30 (6H, m).

mass: 466 (M+1)$^+$.

Example 149

Synthesis of compound represented by following Formula [149]

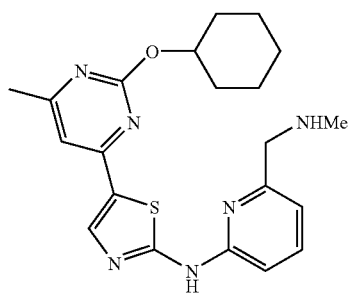

[149]

(1) 200 mL of acetic anhydride was added to 39.9 g of 2-amino-6-methylpyridine at room temperature, and the mixture was stirred at 70° C. for 2 hours. The obtained reaction solution was concentrated, neutralized with an aqueous solution of sodium hydrogen carbonate, and extracted with ethyl acetate. The organic phase was washed with saturated brine. Subsequently, the organic phase was dried over anhydrous sodium sulfate and filtered, and the filtrate was concentrated to obtain 60.6 g of an acetamide product [149-1] as follows.

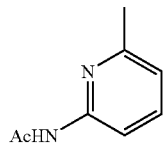

[149-1]

The spectral data of the compound represented by the above Formula [149-1] is presented below.

$^1$H-NMR (CDCl$_3$) δ: 8.10 (1H, brs), 7.97 (1H, d, J=8.0 Hz), 7.57 (1H, t, J=8.0 Hz), 6.88 (1H, d, J=8.0 Hz), 2.43 (3H, s), 2.17 (3H, s).

mass: 151 (M+1)$^+$.

(2) 60.6 g of the acetamide product [149-1] obtained in (1) above was dissolved in 600 mL of water at 75° C., and 175 g of potassium permanganate was added to the solution at the same temperature over 3 hours. The obtained reaction solution was filtered through Celite, and then the filtrate was concentrated. The obtained reaction mixture was neutralized with concentrated hydrochloric acid, and then concentrated to obtain a carboxylic acid product [149-2] as follows.

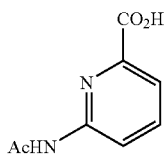

[149-2]

The compound represented by the above Formula [149-2] was confirmed by LC-MS.

mass: 181 (M+1)$^+$.

(3) The carboxylic acid product [149-2] obtained in (2) above was dissolved in a 10% methanol solution of hydrogen chloride, and the solution was heated under reflux overnight. The obtained reaction solution was concentrated, then neutralized with an aqueous solution of sodium hydrogen carbonate, and extracted with ethyl acetate. The organic phase was washed with saturated brine. Subsequently, the organic phase was dried over anhydrous sodium sulfate and filtered, and then the filtrate was concentrated. A white solid generated by adding hexane to the obtained reaction mixture was filtered and dried to obtain 16.5 g of an ester product [149-3] as follows.

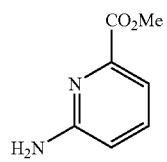

[149-3]

The spectral data of the compound represented by the above Formula [149-3] is presented below.

$^1$H-NMR (CDCl$_3$) δ: 7.48-7.60 (2H, m), 6.68 (1H, d, J=8.0 Hz), 4.72 (2H, brs), 3.96 (3H, s).

mass: 153 (M+1)$^+$.

(4) 5.19 g of the ester product [149-3] obtained in (3) above was dissolved in 100 mL of tetrahydrofuran, then 1.55 g of lithium aluminum hydride was added to the solution in an ice bath, and the mixture was stirred at the same temperature for 1 hour. Sodium sulfate decahydrate was added to the obtained reaction solution, and then the mixture was stirred overnight at room temperature. After filtering the mixture through Celite, the filtrate was concentrated to obtain 2.78 g of an alcohol product [149-4] as follows.

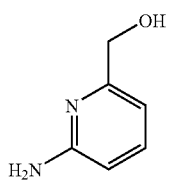

[149-4]

The spectral data of the compound represented by the above Formula [149-4] is presented below.

$^1$H-NMR (CDCl$_3$) δ: 7.42 (1H, t, J=7.6 Hz), 6.60 (1H, d, J=7.6 Hz), 6.41 (1H, d, J=7.6 Hz), 4.59 (2H, s), 4.52 (2H, brs).

mass: 125 (M+1)$^+$.

(5) 2.99 g of a thiourea product [149-5] was obtained from 2.78 g of the Compound [149-4] obtained in (4) above, according to the methods of Example 1-(7) and (8).

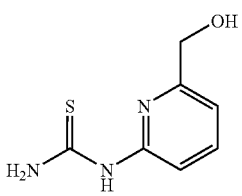

[149-5]

The spectral data of the compound represented by the above Formula [149-5] is presented below.

$^1$H-NMR (DMSO-d$_6$) δ: 10.58 (1H, brs), 10.48 (1H, brs), 8.84 (1H, brs), 7.74 (1H, t, J=8.1 Hz), 7.06 (1H, d, J=8.1 Hz), 7.01 (1H, d, J=8.1 Hz), 5.47 (1H, t, J=5.9 Hz), 4.47 (1H, d, J=5.9 Hz).

mass: 184 (M+1)$^+$.

(6) A Compound [149-6] was obtained from the Compound [149-5] obtained in (5) above, according to the methods of Example 1-(11), (12) and (13), Example 122-(3), and Example 1-(15).

[149-6]

The compound represented by the above Formula [149-6] was confirmed by LC-MS.

mass: 520 (M+1)$^+$.

(7) A Compound [149-7] was obtained from the Compound [149-6], according to the methods of Example 1-(16) and 1-(17).

[149-7]

The spectral data of the compound represented by the above Formula [149-7] is presented below.

$^1$H-NMR (CDCl$_3$) δ: 7.81 (1H, s), 7.62 (1H, t, J=7.6 Hz), 7.04 (1H, d, J=7.6 Hz), 6.87 (1H, d, J=7.6 Hz), 6.28 (1H, s), 5.53 (2H, s), 5.01-5.14 (1H, m), 4.83 (2H, s), 3.49 (1H, brs), 3.47 (3H, s), 2.43 (3H, s), 2.01-2.15 (2H, m), 1.78-1.90 (2H, m), 1.20-1.72 (6H, m).

mass: 442 (M+1)$^+$.

(8) The target compound [149] was obtained as a hydrochloride salt, from the Compound [149-7] and methylamine, according to the methods of Example 1-(18) and (19).

The spectral data of the compound represented by the above Formula [149] is presented below.

$^1$H-NMR (DMSO-d$_6$) δ: 11.93 (1H, brs), 9.46 (2H, brs), 8.40 (1H, s), 7.86 (1H, t, J=8.1 Hz), 7.50 (1H, s), 7.24 (1H, d, J=8.1 Hz), 7.17 (1H, d, J=8.1 Hz), 4.96-5.10 (1H, m), 4.28 (2H, s), 2.68 (3H, s), 2.39 (3H, s), 1.95-2.10 (2H, m), 1.64-1.82 (2H, m), 1.20-1.62 (6H, m).

mass: 411 (M+1)$^+$.

Example 150

Synthesis of compound represented by following Formula [150]

[150]

The target compound [150] was obtained as a hydrochloride salt, from the Compound [149-7] obtained in Example 149-(7) and dimethylamine, according to the method of Example 149-(8).

The spectral data of the compound represented by the above Formula [150] is presented below.

$^1$H-NMR (DMSO-d$_6$) δ: 11.96 (1H, brs), 11.08 (1H, brs), 8.40 (1H, s), 7.87 (1H, t, J=7.2 Hz), 7.49 (1H, s), 7.36 (1H, d, J=7.2 Hz), 7.21 (1H, d, J=7.2 Hz), 5.00-5.11 (1H, m), 4.40 (2H, s), 2.82 (6H, s), 2.39 (3H, s), 1.96-2.08 (2H, m), 1.68-1.82 (2H, m), 1.24-1.62 (6H, m).

mass: 425 (M+1)$^+$.

Example 151

Synthesis of compound represented by following Formula [151]

[151]

The target compound [151] was obtained by adding a 4 N dioxane solution of hydrogen chloride to the Compound [149-7] obtained in Example 149-(7), stirring the mixture at room temperature for 17 hours, and then removing the solvent.

The spectral data of the compound represented by the above Formula [151] is presented below.

$^1$H-NMR (DMSO-d$_6$) δ: 11.95 (1H, brs), 8.43 (1H, s), 7.78 (1H, t, J=8.1 Hz), 7.51 (1H, s), 7.13 (1H, d, J=8.1 Hz), 7.02 (1H, d, J=8.1 Hz), 4.75-5.26 (1H, m), 4.64 (2H, s), 2.40 (3H, s), 2.00-2.14 (2H, m), 1.72-1.86 (2H, m), 1.20-1.66 (6H, m).

mass: 396 (M−1)$^+$.

Example 152

Synthesis of compound represented by following Formula [152]

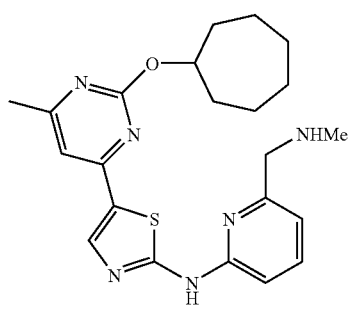

[152]

4.4 mg of a trifluoroacetate salt of the target compound [152] was obtained as a yellow solid, from 59 mg of the Compound [149-6] obtained in Example 149-(6), 77 μL of cycloheptanol, and methylamine, according to the methods of Example 149-(7) and (8).

The spectral data of the compound represented by the above Formula [152] is presented below.

$^1$H-NMR (DMSO-d$_6$) δ: 11.81 (1H, brs), 9.05 (2H, brs), 8.33 (1H, s), 7.85 (1H, brdd, J=8.4, 6.8 Hz), 7.40 (1H, s), 7.13 (1H, brdd, J=9.2, 7.6 Hz), 5.18 (1H, brs), 4.31 (2H, s), 2.73 (3H, s), 2.37 (3H, s), 2.08-1.94 (2H, m), 1.82-1.40 (10H, m).

mass: 425 (M+1)$^+$.

Example 153

Synthesis of compound represented by following Formula [153]

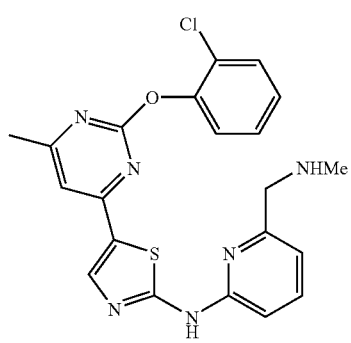

[153]

The target compound [153] was obtained as a hydrochloride salt, from the Compound [149-6] obtained in Example 149-(6), 2-chlorophenol and methylamine, according to the methods of Example 27-(1), and Example 149-(7) and (8).

The spectral data of the compound represented by the above Formula [153] is presented below.

$^1$H-NMR (DMSO-d$_6$) δ: 11.86 (1H, brs), 9.42 (2H, brs), 8.35 (1H, s), 7.13-7.87 (8H, m), 4.16-4.19 (2H, m), 2.61-2.64 (3H, m), 2.36 (3H, s).

mass: 439 (M+1)$^+$.

Example 154

Synthesis of compound represented by following Formula [154]

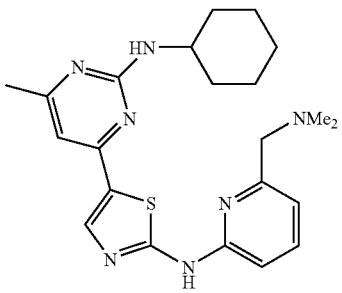

[154]

36 mg of a trifluoroacetate salt of the target compound [154] was obtained as a pale yellow solid, from 54 mg of the Compound [149-6] obtained in Example 149-(6) and 73 μL of cyclohexylamine, according to the methods of Example 47-(1), and Example 149-(7) and (8).

The spectral data of the compound represented by the above Formula [154] is presented below.

$^1$H-NMR (DMSO-d$_6$) δ: 12.2 (1H, brs), 10.4 (1H, brs), 8.66 (1H, brs), 8.55 (1H, brs), 7.92 (1H, dd, J=8.0, 7.6 Hz), 7.32-7.20 (3H, m), 4.40 (2H, s), 4.05-3.85 (1H, m), 2.89 (6H, s), 2.37 (3H, s), 2.00-1.88 (2H, m), 1.82-1.72 (2H, m), 1.66-1.56 (1H, m), 1.48-1.16 (5H, m).

mass: 424 (M+1)$^+$.

Example 155

Synthesis of compound represented by following Formula [155]

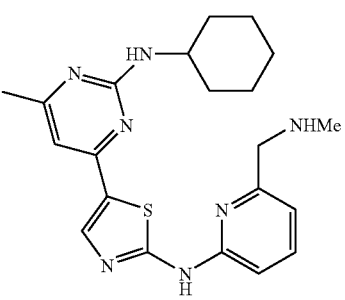

[155]

13.2 mg of a trifluoroacetate salt of the target compound [155] was obtained as a yellow solid, from 54 mg of the Compound [149-6] obtained in Example 149-(6) and 73 μL of cyclohexylamine, according to the methods of Example 47-(1) and Example 149-(7) and (8).

The spectral data of the compound represented by the above Formula [155] is presented below.

$^1$H-NMR (DMSO-d$_6$) δ: 9.13 (2H, brs), 8.47 (1H, brs), 7.88 (1H, dd, J=8.0, 7.6 Hz), 7.26-7.06 (3H, m), 4.29 (2H, brs), 3.95-3.75 (1H, m), 2.66 (3H, s), 2.34 (3H, s), 2.02-1.88 (2H, m), 1.82-1.70 (2H, m), 1.66-1.56 (1H, m), 1.46-1.12 (5H, m).

mass: 410 (M+1)$^+$.

Example 156

Synthesis of compound represented by following Formula [156]

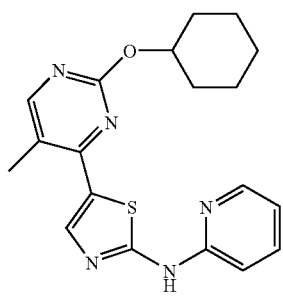
[156]

(1) 50 mL of diisopropylamine was dissolved in 200 mL of THF and cooled to −78° C., and then 207 mL of a 1.59 M hexane solution of n-butyllithium was added dropwise to the solution. After stirring in an ice bath for 1 hour, the obtained reaction solution was cooled to −78° C., and 28 mL of methyl propionate was diluted in 50 mL of THF and added dropwise to the reaction solution. After stirring at the same temperature for 1 hour, 31 mL of ethyl formate was diluted in 50 mL of THF and added dropwise to the reaction mixture. After stirring for 1 hour, water was added to the reaction mixture, and the resulting mixture was heated to room temperature. The mixture was washed with diethyl ether, and 60 mL of 6 N hydrochloric acid was added to the aqueous phase in an ice bath. The aqueous phase was extracted with dichloromethane, dried over sodium sulfate, filtered, and then concentrated to obtain Compound [156-1] as a crude product. The Compound [156-1] was used in the subsequent reaction without further purification.

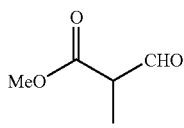
[156-1]

(2) 15 g of thiourea was dissolved in 100 mL of ethanol, then 14 mL of methyl iodide was added dropwise to the solution, and the mixture was heated under reflux. After stirring for 30 minutes, the mixture was concentrated and washed with a mixed solvent of diethyl ether and methanol, to obtain a Compound [156-2] as a white powder.

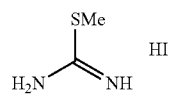
[156-2]

The spectral data of the compound represented by the above Formula [156-2] is presented below.

$^1$H-NMR (DMSO-d$_6$) δ: 8.82 (4H, brs), 2.58 (3H, s).

(3) 25 g of Compound [156-2] was dissolved in 50 mL of a 5 N aqueous solution of sodium hydroxide and 25 mL of water, and the Compound [156-1] obtained in (1) was diluted in 50 mL of ethanol and added to the solution. The mixture was heated under reflux and stirred overnight. 50 mL of acetic acid was added to the mixture in an ice bath, and a white crystal generated thereby was filtered to obtain 15 g of a Compound [156-3].

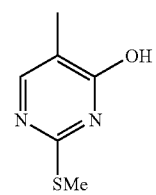
[156-3]

The spectral data of the compound represented by the above Formula [156-3] is presented below.

$^1$H-NMR (DMSO-d$_6$) δ: 7.65 (1H, s), 2.40 (3H, s), 1.80 (3H, s).

mass: 157 (M+1)$^+$.

(4) 15 g of the Compound [156-3] was dissolved in 50 mL of phosphorus oxychloride, and the solution was stirred at 120° C. for 2 hours. The reaction solution was immersed in broken ice, extracted with chloroform, filtered, concentrated, and purified by silica gel column chromatography to obtain 13 g of the target compound [156-4].

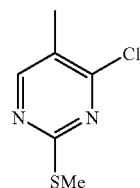
[156-4]

The spectral data of the compound represented by the above Formula [156-4] is presented below.

mass: 175 (M+1)$^+$.

(5) Protected products of aminothiazole [156-5-1] and [156-5-2] were obtained from the Compound [156-4] obtained in (4) above and the thiourea [121-1] obtained in Example 121-(1), according to the methods of Example 1-(10) and (11), and Example 121-(2) and (3).

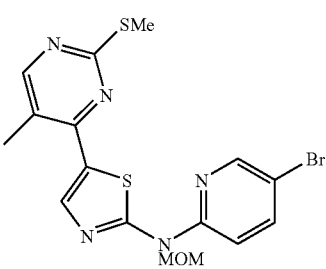
[156-5-1]

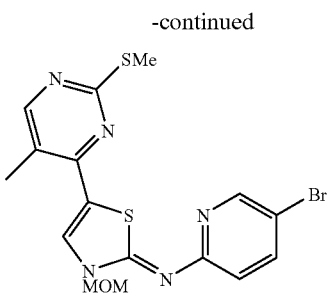

[156-5-2]

The spectral data of the compound represented by the above Formula [156-5-1] is presented below.

¹H-NMR (CDCl₃) δ: 8.55 (1H, s), 8.29 (1H, s), 8.02 (1H, s), 7.82-7.80 (1H, m), 7.30-7.26 (1H, m), 5.80 (2H, s), 3.50 (3H, s), 2.62 (3H, s), 2.42 (3H, s).

mass: 438, 440 (M+1)⁺.

The spectral data of the compound represented by the above Formula [156-5-2] is presented below.

¹H-NMR (CDCl₃) δ: 8.55 (1H, s), 8.26 (1H, s), 7.70-7.66 (1H, m), 7.60 (1H, s), 7.04-7.00 (1H, m), 5.58 (2H, s), 3.50 (3H, s), 2.62 (3H, s), 2.40 (3H, s).

mass: 438, 440 (M+1)⁺.

(6) A Compound [156-6] was obtained from the Compound [156-5-1] according to the methods of Example 1-(15) and (16).

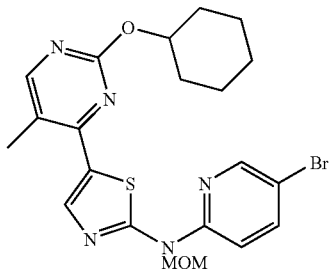

[156-6]

(7) The Compound [156-6] was dissolved in a mixed solvent of THF and methanol, then palladium carbon was added to the solution, and the mixture was stirred overnight in a hydrogen atmosphere at room temperature. After filtering and concentrating, the mixture was purified by preparative thin layer chromatography to obtain a debromination product [156-7].

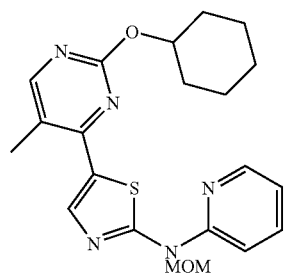

[156-7]

The spectral data of the compound represented by the above Formula [156-7] is presented below.

¹H-NMR (CDCl₃) δ: 8.30-8.20 (1H, m), 8.25 (1H, s), 8.05 (1H, s), 7.80-7.70 (1H, m), 7.36-7.30 (1H, m), 7.10-7.04 (1H, m), 5.80 (2H, s), 5.02-4.92 (1H, m), 3.50 (3H, s), 2.42 (3H, s), 2.20-2.10 (2H, m), 1.90-1.80 (2H, m), 1.75-1.58 (2H, m), 1.58-1.40 (2H, m), 1.20-1.10 (2H, m).

(8) The Compound [156-7] was dissolved in a mixed solvent of chloroform and methanol, then a 4 N dioxane solution of hydrogen chloride was added to the solution, and the mixture was stirred at room temperature. The solvent was removed under reduced pressure, and the residue was solidified from methanol and ether to obtain the target compound [156].

The spectral data of the compound represented by the above Formula [156] is presented below.

¹H-NMR (DMSO-d₆) δ: 11.6 (1H, s), 8.50-8.46 (1H, m), 8.32 (1H, s), 8.07 (1H, s), 7.78-7.72 (1H, m), 7.12-7.10 (1H, m), 7.00-6.95 (1H, m), 4.92-4.83 (1H, m), 2.38 (3H, s), 2.09-2.00 (2H, m), 1.82-1.72 (2H, m), 1.63-1.20 (6H, m).

mass: 368 (M+1)⁺.

Example 157

Synthesis of compound represented by following Formula [157]

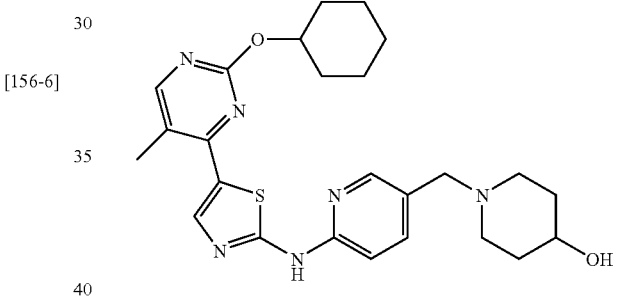

[157]

(1) A benzyl alcohol product [157-1] was obtained from the Compound [156-4] obtained in Example 156 and the Compound [121-1] obtained in Example 121, according to the methods of Example 1-(12), (14), (15), (16), and Example 125-(1), (2) and (3).

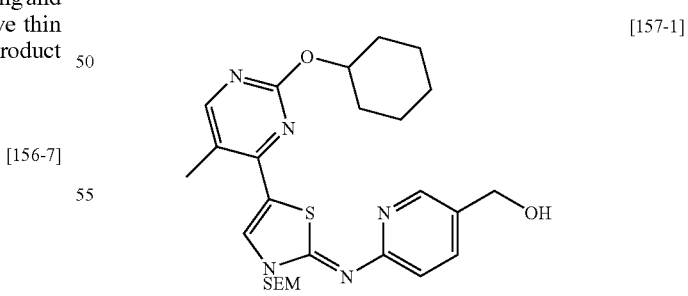

[157-1]

The spectral data of the compound represented by the above Formula [157-1] is presented below.

¹H-NMR (CDCl₃) δ: 8.43 (1H, s), 8.25 (1H, s), 7.66 (1H, d, J=8.0 Hz), 7.62 (1H, s), 7.14 (1H, d, J=8.0 Hz), 5.60 (2H, s), 5.08-4.97 (1H, m), 4.70 (2H, s), 3.78-3.71 (2H, m), 2.40 (3H, s), 2.20-1.30 (10H, m), 1.04-0.98 (2H, m), 0.01 (9H, s).

mass: 528 (M+1)⁺.

(2) The target compound [157] was obtained from the Compound [157-1] obtained in (1) above and 4-hydroxypiperidine, according to the methods of Example 1-(18) and (19).

The spectral data of the compound represented by the above Formula [157] is presented below.

$^1$H-NMR (CDCl$_3$) δ: 8.25 (1H, s), 8.21 (1H, s), 7.93 (1H, s), 7.65 (1H, d, J=8.4 Hz), 6.91 (1H, d, J=8.4 Hz), 5.05-4.95 (1H, m), 3.71 (1H, brs), 3.50 (2H, s), 2.85-2.70 (2H, m), 2.43 (3H, s), 2.28-1.12 (16H, m).

mass: 481 (M+1)$^+$.

Examples 158-163

Synthesis of compound represented by following General Formula [158-1] (wherein R$_a$ and R$_b$, which may be identical or different, are each a hydrogen atom, a lower alkyl group, a C$_3$-C$_8$ cycloalkyl group, or an aliphatic heterocyclic group, or R$_a$ and R$_b$ may together form an aliphatic heterocyclic ring, and the lower alkyl group, aliphatic heterocyclic group and cycloalkyl group may be substituted):

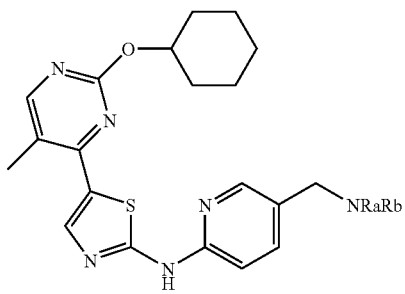

[158-1]

The target compounds [158] to [163] (respectively corresponding to Examples 158 to 163) were obtained as hydrochloride salts, from the Compound [157-1] obtained in Example 157 and morpholine (in the case of Example 158), diethylamine (in the case of Example 159), dimethylamine (in the case of Example 160), piperidine (in the case of Example 161), N-methylpiperazine (in the case of Example 162), and N-ethylpiperazine (in the case of Example 163), respectively, according to the methods of Examples 8-22. The target compounds were confirmed by LC-MS.

TABLE 30

| Examples 158 to 161 | Structure | Molecular formula | Mass (M + 1)$^+$ |
|---|---|---|---|
| 158 | 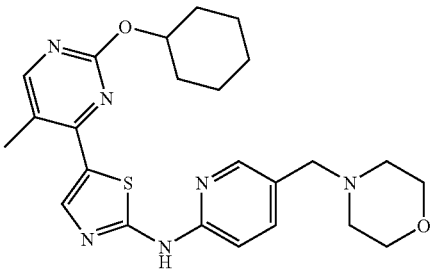 | C24H30N6O2S | 467 |
| 159 | 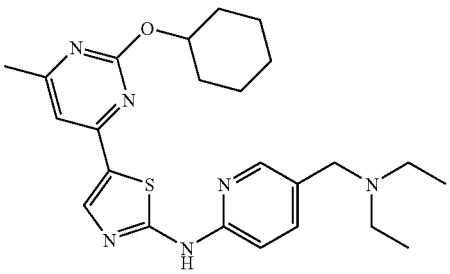 | C24H33N7S | 453 |
| 160 | 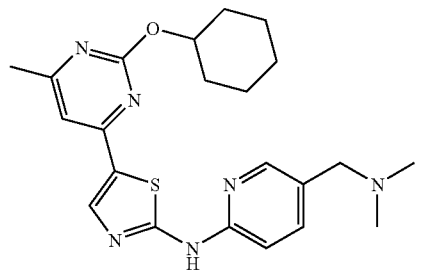 | C22H28N6OS | 425 |

TABLE 30-continued

| Examples 158 to 161 | Structure | Molecular formula | Mass (M + 1)+ |
|---|---|---|---|
| 161 | 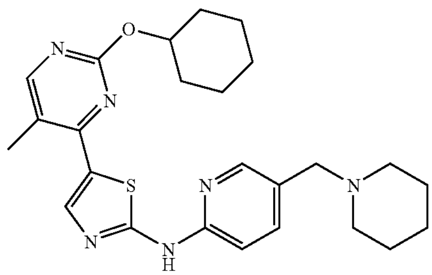 | C25H32N6OS | 465 |

TABLE 31

| Examples 162 to 163 | Structure | Molecular formula | Mass (M + 1)+ |
|---|---|---|---|
| 162 | 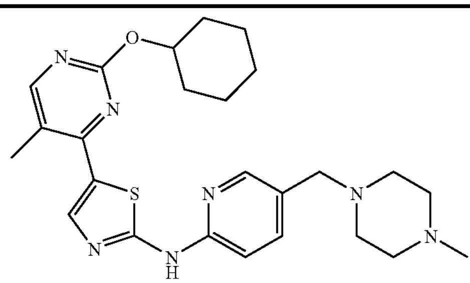 | C25H33N7OS | 480 |
| 163 | 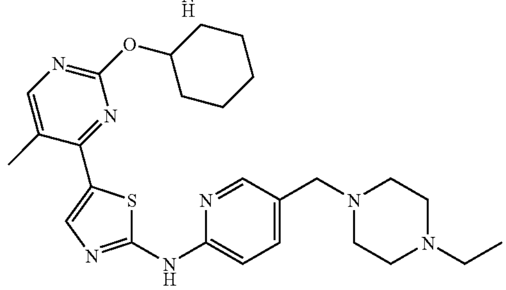 | C26H35N7OS | 494 |

Example 164

Synthesis of compound represented by following Formula [164]

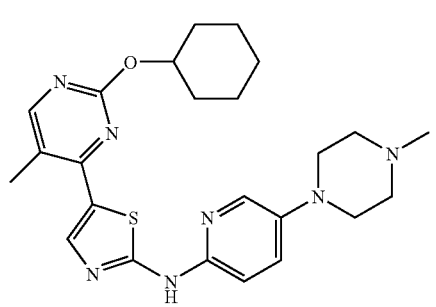

[164]

The target compound [164] was obtained as a hydrochloride salt, from the Compound [156-6] obtained in Example 156, according to the methods of Examples 147 and 148.

The spectral data of the compound represented by the above Formula [164] is presented below.

$^1$H-NMR (DMSO-d$_6$) δ: 11.5 (1H, brs), 10.2 (1H, brs), 8.29 (1H, s), 8.14 (1H, d, J=2.2 Hz), 8.02 (1H, s), 7.54 (1H, dd, J=2.2, 8.8 Hz), 7.05 (1H, d, J=8.8 Hz), 4.95-4.85 (1H, m), 3.85-3.80 (2H, m), 3.52-3.42 (2H, m), 3.20-3.00 (4H, m), 2.80 (3H, d, J=4.4 Hz), 2.35 (3H, s), 2.20-1.95 (2H, m), 1.78-1.68 (2H, m), 1.60-1.20 (6H, m).

mass: 466 (M+1)+.

Example 165

Synthesis of compound represented by following Formula [165]

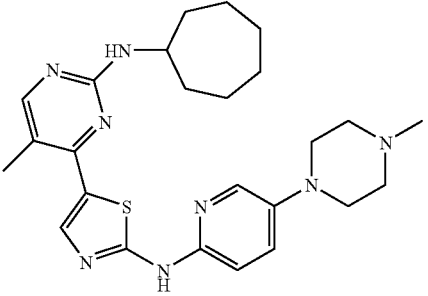

[165]

(1) A Compound [165-1] was obtained from the Compound [156-5-1] obtained in Example 156-(5), according to the methods of Example 1-(15) and Example 47-(1).

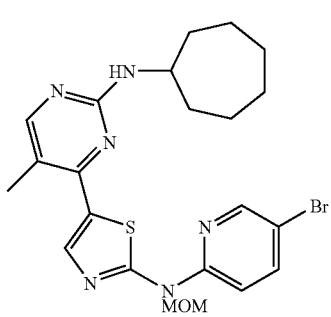

[165-1]

The compound represented by the above Formula [165-1] was confirmed by MS.

mass: 503 (M+1)$^+$.

(2) The target compound [165] was obtained as a yellow solid, from the Compound [165-1] obtained in (1) above, according to the methods of Examples 147 and 148.

The spectral data of the compound represented by the above Formula [165] is presented below.

$^1$H-NMR (DMSO-d$_6$) δ: 10.6 (1H, brs), 8.26 (1H, brs), 8.08 (1H, s), 7.98-7.93 (1H, m), 7.60 (1H, dd, J=9.2, 3.5 Hz), 7.12 (1H, d, J=9.2 Hz), 3.98-3.86 (1H, m), 3.80-3.72 (2H, m), 3.56-3.04 (6H, m), 2.82 (3H, d, J=4.4 Hz), 2.36 (3H, s), 2.00-1.20 (12H, m).

mass: 479 (M+1)$^+$.

Example 166

Synthesis of compound represented by following Formula [166]

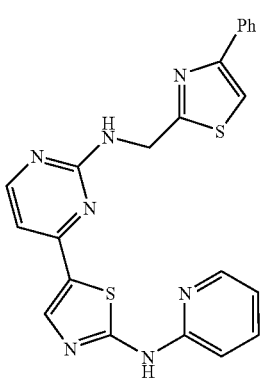

[166]

The target compound [166] was obtained from the Compounds [121-1] and [120-2] obtained in Example 121, according to the methods of Example 1-(12), (14) and (15), and Example 47.

The spectral data of the compound represented by the above Formula [166] is presented below.

$^1$H-NMR (DMSO-d$_6$) δ: 12.03 (1H, brs), 9.04 (1H, brs), 8.59 (1H, brs), 8.30-8.22 (2H, m), 8.01 (1H, s), 7.95-7.93 (2H, m), 7.79-7.75 (1H, m), 7.40-7.28 (3H, m), 7.15 (1H, d, J=8.1 Hz), 7.01-6.98 (1H, m), 4.96 (2H, s).

mass: 444 (M+1)$^+$.

Example 167

Synthesis of compound represented by following Formula [167]

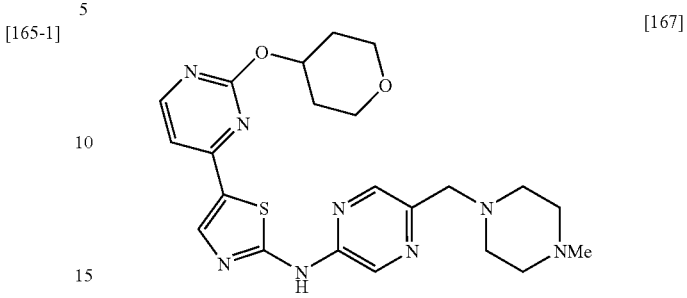

[167]

(1) A Compound [167-1] was obtained from the Compound [1-8] obtained in Example 1-(8) and the Compound [121-2] obtained in Example 121-(2), according to the methods of Example 1-(12), (13), (14), (15), (16) and (17).

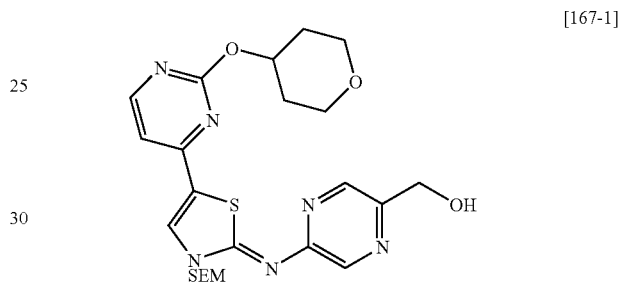

[167-1]

The compound represented by the above Formula [167-1] was confirmed by LC-MS.

mass: 517 (M+1)$^+$.

(2) The target compound [167] was obtained from the Compound [167-1] obtained in (1) above, according to the methods of Example 1-(18) and (19).

The spectral data of the compound represented by the above Formula [167] is presented below.

$^1$H-NMR (DMSO-d$_6$) δ: 8.64 (1H, s), 8.56 (1H, s), 8.50 (1H, d, J=5.4 Hz), 8.46 (1H, s), 7.58 (1H, d, J=5.4 Hz), 5.08-5.20 (1H, m), 4.46 (2H, s), 3.35-4.35 (12H, m), 2.80 (3H, s), 1.98-2.12 (2H, m), 1.64-1.78 (2H, m).

mass: 469 (M+1)$^+$.

Example 168

Synthesis of compound represented by following Formula [168]

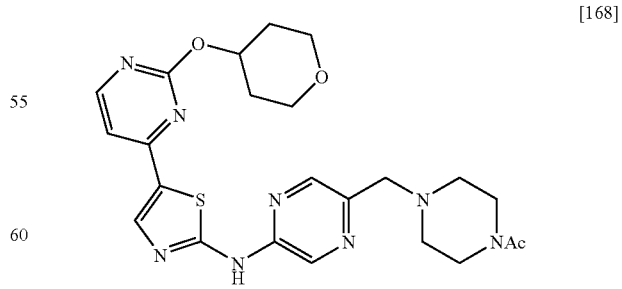

[168]

The target compound [168] was obtained from the Compound [167-1] obtained in Example 167-(1) and N-acetylpiperazine, according to the methods of Example 1-(18) and (19).

The spectral data of the compound represented by the above Formula [168] is presented below.

$^1$H-NMR (DMSO-d$_6$) δ: 11.28 (1H, brs), 8.64 (1H, s), 8.56 (1H, s), 8.50 (1H, d, J=5.4 Hz), 8.46 (1H, s), 7.58 (1H, d, J=5.4 Hz), 5.08-5.21 (1H, m), 4.44 (2H, s), 2.90-4.30 (12H, m), 1.98-2.50 (2H, m), 2.02 (3H, s), 1.60-1.78 (2H, m).

mass: 497 (M+1)$^+$.

Example 169

Synthesis of compound represented by following Formula [169]

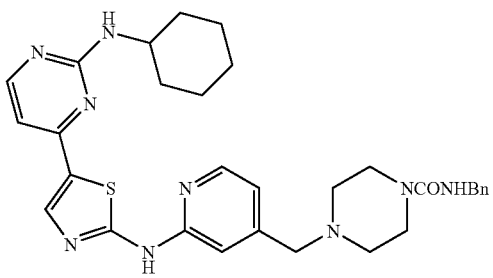

[169]

(1) A Compound [169-1] was obtained from the Compound [120-2] obtained in Example 121 and the Compound [122-5] obtained in Example 122, according to the methods of Example 1-(12), 1-(13), 1-(14), 1-(15), Example 47, and Example 1-(17).

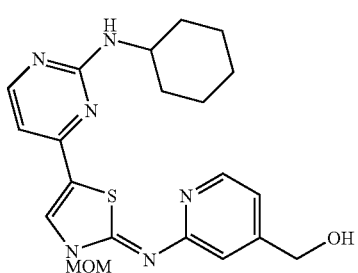

[169-1]

The spectral data of the compound represented by the above Formula [169-1] is presented below.

$^1$H-NMR (CDCl$_3$) δ: 8.45 (1H, d, J=5.2 Hz), 8.19 (1H, d, J=5.2 Hz), 7.67 (1H, s), 7.10 (1H, s), 6.91-6.90 (1H, m), 6.61 (1H, d, J=5.3 Hz), 5.55 (2H, s), 5.05 (1H, d, J=8.0 Hz), 4.73 (2H, s), 3.93-3.82 (1H, m), 3.45 (3H, s), 2.13-1.09 (11OH, m).

(2) A Compound [169-2] was obtained from the Compound [169-1] obtained in (1) above and N-Boc piperazine, according to the methods of Example 1-(18) and (19).

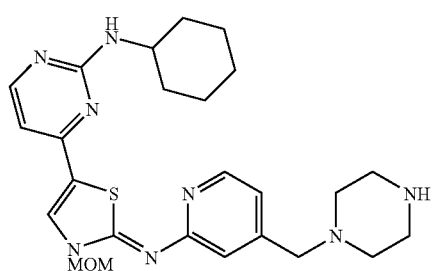

[169-2]

The spectral data of the compound represented by the above Formula [169-2] is presented below.

$^1$H-NMR (CDCl$_3$) δ: 8.43 (1H, d, J=5.2 Hz), 8.21 (1H, d, J=5.2 Hz), 7.66 (1H, s), 7.10 (1H, s), 6.93 (1H, d, J=5.2 Hz), 6.91 (1H, d, J=5.2 Hz), 5.54 (2H, s), 5.05 (1H, d, J=7.6 Hz), 3.93-3.82 (1H, m), 3.49 (2H, s), 3.47 (3H, s), 2.93-2.89 (4H, m), 2.50-2.38 (4H, m), 2.12-1.09 (10H, m).

(3) The Compound [169-2] obtained in (2) above was dissolved in chloroform, and was reacted with benzylisocyanate in the presence of triethylamine. The reaction solution was poured onto a saturated solution sodium hydrogen carbonate, extracted with chloroform, dried, and concentrated, and the residue was purified by preparative thin layer chromatography to obtain a Compound [169-3].

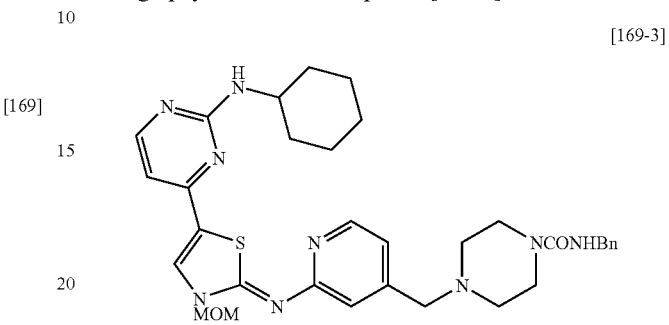

[169-3]

The spectral data of the compound represented by the above Formula [169-3] is presented below.

$^1$H-NMR (CDCl$_3$) δ: 8.43 (1H, d, J=5.2 Hz), 8.21 (1H, d, J=5.2 Hz), 7.66 (1H, s), 7.35-7.28 (5H, m), 7.09 (1H, s), 6.92 (1H, dd, J=1.6, 5.2 Hz), 6.61 (1H, d, J=5.2 Hz), 5.54 (2H, s), 5.04 (1H, d, J=7.6 Hz), 4.68 (1H, t, J=5.6 Hz), 4.43 (2H, d, J=5.6 Hz), 3.92-3.83 (1H, m), 3.51 (2H, s), 3.46 (3H, s), 3.41-3.40 (4H, m), 2.47-2.45 (4H, m), 2.10-1.19 (10H, m).

(4) The Compound [169-3] obtained in (3) above was dissolved in methanol, then a 4 N dioxane solution of hydrogen chloride was added to the solution, and the mixture was stirred at room temperature for several hours. The reaction solution was concentrated, and the residue was solidified from methanol and ether to obtain the target compound [169] as a hydrochloride salt.

The spectral data of the compound represented by the above Formula [169] is presented below.

$^1$H-NMR (DMSO-d$_6$) δ: 8.58 (1H, brs), 8.44 (1H, brs), 8.18 (1H, brs), 7.38-7.13 (8H, m), 4.43-4.30 (2H, m), 4.26-4.22 (2H, m), 4.17-4.02 (2H, m), 3.72-2.91 (7H, m), 2.03-1.92 (2H, m), 1.86-1.70 (2H, m), 1.68-1.57 (1H, m), 1.45-1.09 (5H, m).

mass: 584 (M+1)$^+$.

Example 170

Synthesis of compound represented by following Formula [170]

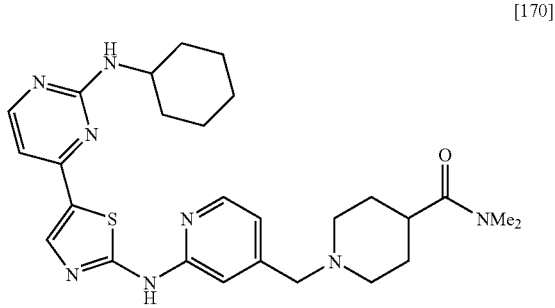

[170]

The target compound [170] was obtained from the Compound [169-1] obtained in Example 169 and piperidine-4-carboxylic acid dimethylamide, according to the methods of Example 1-(18) and (19).

The spectral data of the compound represented by the above Formula [170] is presented below.

¹H-NMR (CDCl₃) δ: 8.35 (1H, d, J=5.2 Hz), 8.21 (1H, d, J=5.7 Hz), 8.01 (1H, s), 6.99-6.91 (2H, m), 6.79 (1H, d, J=5.2 Hz), 5.13 (1H, brs), 3.94-3.84 (1H, m), 3.51 (2H, s), 3.05 (3H, s), 2.95 (3H, s), 3.00-2.89 (2H, m), 2.58-2.46 (1H, m), 2.14-2.00 (4H, m), 1.95-1.85 (2H, m), 1.84-1.53 (5H, m), 1.52-1.40 (2H, m), 1.33-1.18 (3H, m).

mass: 521 (M+1)⁺.

Example 171

Synthesis of compound represented by following Formula [171]

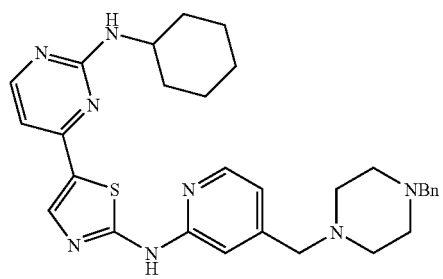

[171]

The target compound [171] was obtained from the Compound [169-1] obtained in Example 169 and N-benzylpiperazine, according to the methods of Example 1-(18) and (19).

The spectral data of the compound represented by the above Formula [171] is presented below.

¹H-NMR (DMSO-d₆) δ: 8.60 (1H, br), 8.33 (1H, br), 8.14 (1H, br), 7.55 (1H, br), 7.41-7.30 (5H, m), 7.16-7.12 (2H, m), 4.30 (2H, br), 3.95-3.43 (3H, m), 3.40-3.25 (4H, m), 3.20-2.90 (4H, m), 2.00-1.83 (2H, m), 1.82-1.58 (2H, m), 1.68-1.57 (1H, m), 1.47-1.10 (5H, m).

mass: 541 (M+1)⁺.

Example 172

Synthesis of compound represented by following Formula [172]

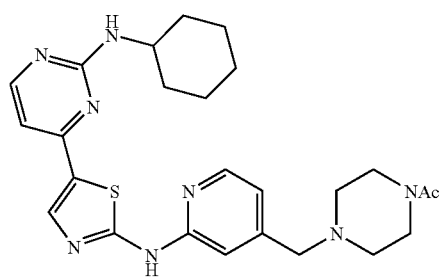

[172]

The target compound [172] was obtained from the Compound [169-1] obtained in Example 169 and N-acetylpiperazine, according to the methods of Example 1-(18) and (19).

The spectral data of the compound represented by the above Formula [172] is presented below.

¹H-NMR (DMSO-d₆) δ: 8.61 (1H, br), 8.53 (1H, s), 8.22 (1H, br), 7.99-7.97 (1H, m), 7.30 (1H, br), 7.23 (1H, d, J=8.4 Hz), 4.50-4.30 (3H, m), 4.03-4.00 (1H, m), 3.87-3.20 (3H, m), 3.17-2.84 (4H, m), 2.06 (3H, s), 2.00-1.83 (2H, m), 1.82-1.58 (2H, m), 1.68-1.57 (1H, m), 1.47-1.10 (5H, m).

mass: 493 (M+1)⁺.

INDUSTRIAL APPLICABILITY

The compound of the present invention has an excellent selected inhibitory action against Cdk4 and/or Cdk6 and thus is useful as a highly safe anititumor agent in the field of medicine.

The invention claimed is:
1. A compound represented by Formula [I]:

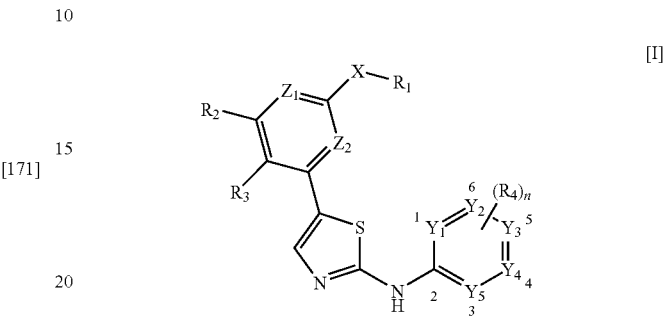

[I]

wherein
X is O, S, NH or CH₂;
Y₁, Y₂, Y₃, Y₄ and Y₅, which may be identical or different, are each CH or N; however, at least one of Y₁, Y₂, Y₃, Y₄ and Y₅ is N;
Z₁ and Z₂, which may be identical or different, are each CH or N;
n is an integer from 1 to 3;
R₁ is a C₃-C₈ cycloalkyl group, a C₆-C₁₀ aryl group, an aliphatic heterocyclic group or an aromatic heterocyclic group selected from "Substituent Group α₁", or a bicyclic aliphatic saturated hydrocarbon group selected from "Substituent Group α₂", wherein the cycloalkyl group, aryl group, aliphatic heterocyclic group or aromatic heterocyclic group, or bicyclic aliphatic saturated hydrocarbon group may be substituted with one or more of identical or different substituents selected from the following 1) to 3):
1) a lower alkyl group,
2) a substituent selected from "Substituent Group β", and
3) a lower alkyl group substituted with a substituent selected from "Substituent Group β";
R₂ and R₃, which may be identical or different, are each a hydrogen atom, a lower alkyl group, a lower alkenyl group, a C₃-C₈ cycloalkyl group, a C₆-C₁₀ aryl group, an aromatic heterocyclic group selected from "Substituent Group α₃", or a substituent selected from "Substituent Group β", wherein the lower alkyl group, lower alkenyl group, cycloalkyl group, aryl group or aromatic heterocyclic group may be substituted with one or more of identical or different substituents selected from "Substituent Group β";
R₄ is a hydrogen atom, a lower alkyl group, a C₃-C₆ cycloalkyl group, a substituent selected from "Substituent Group β", or —W₁—W₂, wherein:
W₁ is any one selected from the following:

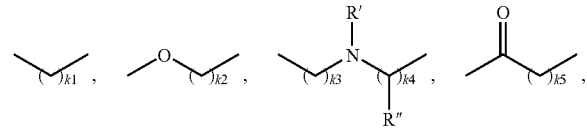

-continued

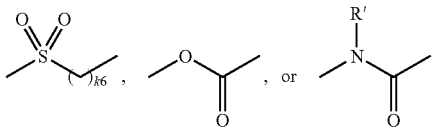

wherein $k_1$ is an integer from 0 to 5; $k_2$, $k_4$, $k_5$ and $k_6$, which may be identical or different, are each an integer from 0 to 4; $k_3$ is an integer of 0 or 1; and R' and R", which may be identical or different, are each a hydrogen atom or a lower alkyl group, $W_2$ is a hydrogen atom, a lower alkyl group, a $C_3$-$C_8$ cycloalkyl group, a substituent selected from "Substituent Group β", a $C_6$-$C_{10}$ aryl group, an aliphatic heterocyclic group selected from "Substituent Group $γ_1$", or an aromatic heterocyclic group selected from "Substituent Group $γ_2$", wherein the lower alkyl group, cycloalkyl group, aryl group, aliphatic heterocyclic group or aromatic heterocyclic group may be substituted with one or more of identical or different substituents selected from the following 1) to 6):

1) a lower alkyl group,
2) a $C_3$-$C_6$ cycloalkyl group,
3) a substituent selected from "Substituent Group β",
4) a lower alkyl group substituted with a substituent selected from "Substituent Group β",
5) a substituent selected from "Substituent Group δ", and
6) a lower alkyl group substituted with a substituent selected from "Substituent Group δ", and if $W_2$ is a lower alkyl group, any of the carbon atoms in the alkyl group may form a spiro-heterocyclic ring; and
if $W_1$ is

and $k_1$ is 0, $W_2$ is not a substituent selected from "Substituent Group β";

the "Substituent Group $α_1$", "Substituent Group $α_2$", "Substituent Group $α_3$", "Substituent Group β", "Substituent Group $γ_1$", "Substituent Group $γ_2$" and "Substituent Group δ" being defined as follows:

"Substituent Group $α_1$":

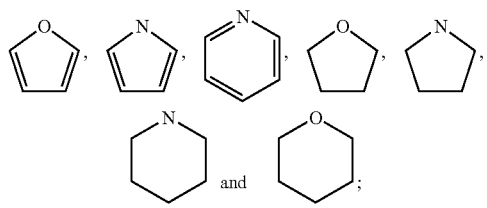

"Substituent Group $α_2$":

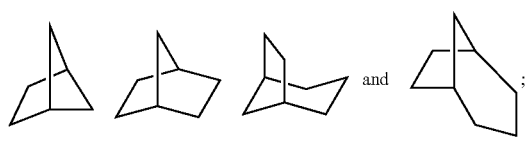

-continued
"Substituent Group $α_3$":

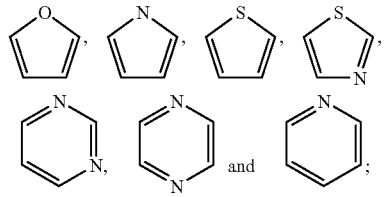

"Substituent Group β":
A halogen atom, OH, OR, $CF_3$, CN, $NH_2$, NHR, $NR_aR_b$, NHCOR, $NR_aCOR_b$, $NHCO_2R$, $NR_aCO_2R_b$, NHCONHR, $NHSO_2R$, $CONH_2$, CONHR, $CONR_aR_b$, COR, $COCF_3$, $CO_2R$, OCOR, $OCO_2R$, $OCONR_aR_b$, $SO_3R$, $SO_2NH_2$, $SO_2NHR$, and $SO_2NR_aR_b$, wherein R, $R_a$ and $R_b$, which may be identical or different, are each a lower alkyl group;

"Substituent Group $γ_1$":

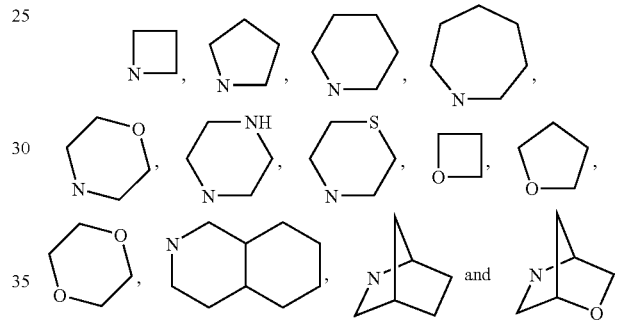

wherein the two hydrogen atoms binding to the same carbon atom constituting an aliphatic heterocyclic group may together form an oxo group;

"Substituent Group $γ_2$":

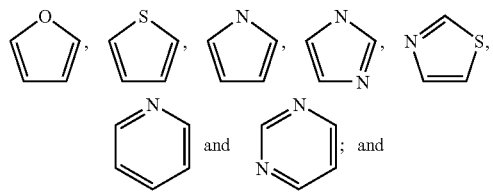

"Substituent Group δ":

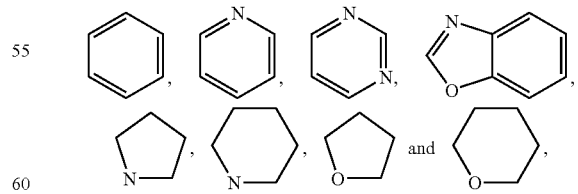

or a pharmaceutically acceptable salt thereof.

2. The compound according to claim 1, or a pharmaceutically acceptable salt thereof, wherein $Y_1$ is N; $Y_2$, $Y_3$ and $Y_5$ are each CH;
$Y_4$ is CH or N; and $Z_1$ and $Z_2$ are each N.

3. The compound according to claim 2, or a pharmaceutically acceptable salt thereof, wherein X is O, S or NH; and $R_1$ is a $C_5$-$C_6$ cycloalkyl group, a phenyl group, or an aliphatic heterocyclic group selected from the "Substituent Group $\alpha_1$", wherein the "Substituent Group $\alpha_1$" is:

[structures of piperidine and tetrahydropyran] and .

4. The compound according to claim 3, or a pharmaceutically acceptable salt thereof, wherein $R_2$ and $R_3$, which may be identical or different, are each a hydrogen atom or a methyl group, provided that at least one of $R_2$ and $R_3$ is a methyl group.

5. The compound according to claim 4, or a pharmaceutically acceptable salt thereof, wherein the substitution position of $R_4$ is the 4-position, 5-position or 6-position, and n is 1.

6. The compound according to claim 5, or a pharmaceutically acceptable salt thereof, wherein the "Substituent Group $\beta$" is a halogen atom, OH, $CF_3$, $NH_2$, NHR, $NR_aR_b$, NHCOR, CONHR, $CONR_aR_b$, COR and $CO_2R$, wherein R, $R_a$ and $R_b$, which may be identical or different, are each a lower alkyl group.

7. The compound according to claim 6, or a pharmaceutically acceptable salt thereof, wherein the "Substituent Group $\gamma_1$" is:

[structures of pyrrolidine, piperidine, morpholine, piperazine, tetrahydrofuran, dioxane, and decahydroisoquinoline]

wherein two hydrogen atoms binding to the same carbon atom which constitutes the aliphatic heterocyclic group may together form an oxo group, and the "Substituent Group $\gamma_2$" is:

[structures of thiophene, thiazole, and pyrimidine]

8. The compound according to claim 7, or a pharmaceutically acceptable salt thereof, wherein $R_4$ is a hydrogen atom, a substituent selected from the "Substituent Group $\beta$", or —$W_1$—$W_2$, wherein:

$W_1$ is any one selected from the following:

[structures]

wherein $k_1$ is 0 or 1; $k_3$ is 1; $k_4$ is 0, 1 or 2; and R' and R", which may be identical or different, are each a hydrogen atom or a methyl group; and $W_2$ is a lower alkyl group, a $C_3$-$C_6$ cycloalkyl group, a substituent selected from the "Substituent Group $\beta$", an aliphatic heterocyclic group selected from the "Substituent Group $\gamma_1$", or an aromatic heterocyclic group selected from the "Substituent Group $\gamma_2$".

9. The compound according to claim 2, or a pharmaceutically acceptable salt thereof, wherein X is O, S or NH;

$R_1$ is a cyclohexyl group, a cyclopentyl group, or a 2-chlorophenyl group;

one of $R_2$ and $R_3$ is a hydrogen atom, while the other is a methyl group;

$R_4$ is —$W_1$—$W_2$ substituted at the 4-position, 5-position or 6-position wherein $W_1$ is

[structure] ;

$k_1$ is 0 or 1; and $W_2$ is 4-methyl-1-piperazinyl group, 4-acetyl-1-piperazinyl group, methylamino group, dimethylamino group, 1-pyrrolidinyl group, 1-piperidinyl group, 4-hydroxy-1-piperidinyl group, 3-hydroxy-1-pyrrolidinyl group, 3-dimethylamino-1-pyrrolidinyl group, 2-hydroxymethyl-1-pyrrolidinyl group, (2-hydroxyethyl)methylamino group, ethylamino group, isopropylamino group, or hydroxyethylamino group.

10. The compound according to claim 1, or a pharmaceutically acceptable salt thereof, which is 5-[2-(cyclohexyloxy)-6-methyl-4-pyrimidinyl]-2-[5-(4-methyl-1-piperazinyl)methyl-2-pyrazinyl] amino-1,3-thiazole, 5-[2-(cyclohexyloxy)-6-methyl-4-pyrimidinyl]-2-[5-(3-dimethylamino-1-pyrrolidinyl)methyl-2-pyrazinyl] amino-1,3-thiazole, 5-[2-(cyclohexylamino)-6-methyl-4-pyrimidinyl]-2-[5-(ethylamino)methyl-2-pyrazinyl] amino-1,3-thiazole, 5-[2-(cyclohexylamino)-6-methyl-4-pyrimidinyl]-2-[5-(4-methyl-1-piperazinyl)methyl-2-pyrazinyl]amino-1,3-thiazole, 5-[2-(cyclohexylthio)-6-methyl-4-pyrimidinyl]-2-[5-(1-pyrrolidinyl)methyl-2-pyrazinyl] amino-1,3-thiazole, 5-[2-(cyclohexylthio)-6-methyl-4-pyrimidinyl]-2-[5-(3-dimethylamino-1-pyrrolidinyl)methyl-2-pyrazinyl] amino-1,3-thiazole, 5-[2-(cyclohexylthio)-6-methyl-4-pyrimidinyl]-2-[5-(isopropylamino)methyl-2-pyrazinyl] amino-1,3-thiazole, 5-[2-(cyclohexylthio)-6-methyl-4-pyrimidinyl]-2-[5-(2-hydroxyethylamino)methyl-2-pyrazinyl] amino-1,3-thiazole, 5-[2-(2-chlorophenylthio)-6-methyl-4-pyrimidinyl]-2-[5-(ethylamino)methyl-2-pyrazinyl] amino-1,3-thiazole, 5-[2-(2-chlorophenylthio)-6-methyl-4-pyrimidinyl]-2-[5-(isopropylamino)methyl-2-pyrazinyl] amino-1,3-thiazole, 5-[2-(2-chlorophenylthio)-6-methyl-4-pyrimidinyl]-2-[5-(4-methyl-1-piperazinyl)methyl-2-pyrazinyl]amino-1,3-thiazole, (2S)-5-[2-(2-chlorophenylthio)-6-methyl-4-pyrimidinyl]-2-[5-(2-hydroxymethyl-1-pyrrolidinyl)methyl-2-pyrazinyl] amino-1,3-thiazole, 5-[2-(2-chlorophenylthio)-6-methyl-4-pyrimidinyl]-2-[5-(1-pyrrolidinyl)methyl-2-pyrazinyl] amino-1,3-thiazole, 5-[2-(2-chlorophenylthio)-6-methyl-4-pyrimidinyl]-2-{5-[(2-hydroxyethyl)methylamino]methyl-2-pyrazinyl}amino-1,3-thiazole, (3R)-5-[2-(2-chlorophenylthio)-6-methyl-4-pyrimidinyl]-2-[5-(3-hydroxy-1-pyrrolidinyl)methyl-2-pyrazinyl] amino-1,3-thiazole, 5-[2-(cyclohexyloxy)-6-methyl-4-pyrimidinyl]-2-[5-(4-acetyl-1-piperazinyl)methyl-2-pyridyl] amino-1,3-thiazole, or (2S)-5-[2-(cyclohexylamino)-6-methyl-4-pyrimidinyl]-2-[5-(2-hydroxymethyl-1-pyrrolidinyl)methyl-2-pyridyl] amino-1,3-thiazole.

11. A pharmaceutical composition comprising at least one species of the compound according to claim 1 as an active ingredient, together with a pharmaceutically acceptable carrier or diluent.

\* \* \* \* \*